(12) United States Patent
Yamamoto et al.

(10) Patent No.: US 8,278,329 B2
(45) Date of Patent: *Oct. 2, 2012

(54) DIARYLALKENE DERIVATIVES AND NOVEL DIARYLALKANE DERIVATIVES

(75) Inventors: Takashi Yamamoto, Kawasaki (JP); Seiji Niwa, Kawasaki (JP); Kayo Otani, Kawasaki (JP); Seiji Ohno, Kawasaki (JP); Hajime Koganei, Kawasaki (JP); Satoshi Iwayama, Kawasaki (JP); Akira Takahara, Kawasaki (JP); Yukitsugu Ono, Kawasaki (JP); Tomoko Takeda, Kawasaki (JP); Shinichi Fujita, Kawasaki (JP); Keiko Moki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1265 days.

This patent is subject to a terminal disclaimer.

(21) Appl. No.: 11/924,997

(22) Filed: Oct. 26, 2007

(65) Prior Publication Data

US 2008/0058311 A1    Mar. 6, 2008

Related U.S. Application Data

(60) Division of application No. 10/787,175, filed on Feb. 27, 2004, now Pat. No. 7,462,630, which is a continuation of application No. PCT/JP02/08809, filed on Aug. 30, 2002.

(30) Foreign Application Priority Data

Aug. 31, 2001  (JP) ................................. 2001-263718
Jan. 23, 2002  (JP) .................................... 2002-14387
Apr. 12, 2002  (JP) ................................. 2002-111067

(51) Int. Cl.
*A61K 31/445* (2006.01)
*C07D 211/18* (2006.01)

(52) U.S. Cl. ......... 514/325; 514/212; 540/607; 546/203
(58) Field of Classification Search .................. 514/325, 514/212; 546/203; 540/607
See application file for complete search history.

(56) References Cited

U.S. PATENT DOCUMENTS

| 4,297,346 A | 10/1981 | Rips et al. ........................ 514/19 |
| 5,714,501 A * | 2/1998 | Timmerman et al. ......... 514/325 |
| 2005/0009814 A1 | 1/2005 | Iwayama et al. ........... 514/225.8 |

FOREIGN PATENT DOCUMENTS

| EP | 0 682 015 A1 | 11/1995 |
| EP | 0 710 661 A1 | 5/1996 |
| EP | 0 739 881 A2 | 10/1996 |
| JP | 8-3135 | 1/1996 |
| JP | 8-3155 | 1/1996 |
| JP | 8-119940 | 5/1996 |
| JP | 8-291142 | 11/1996 |
| WO | WO 95/11238 | 4/1995 |
| WO | WO 99/00376 | 1/1999 |
| WO | 99/37296 | 7/1999 |
| WO | 99/55688 | 11/1999 |
| WO | WO 00/01375 | 1/2000 |
| WO | WO 02/22588 | 3/2002 |

OTHER PUBLICATIONS

Stefani et al. "The effects of gabapentin . . . " Epilepsy Res. v.43 p. 239-248 (2001).*
Timmerman et al. "Preparation of piperidine . . . " CA126:18791 (1996).*
Verbiscar et al. "Carbamate ester . . . " J. Med. Chem. v.13, p. 1176-79 (1970).*
Greene "Protective groups . . . " p. 218-251 (1982).*
R.S. Kamel, et al., *Clinical Chemistry*, vol. 25, No. 12, pp. 1997-2002 (1979).

(Continued)

*Primary Examiner* — Celia Chang
(74) *Attorney, Agent, or Firm* — Oblon, Spivak, McClelland, Maier & Neustadt, L.L.P.

(57) ABSTRACT

The invention relates to a compound represented by the following general formula (1) or its analogue, which selectively inhibit N-type calcium channels or its analogue, and to a method for treating pain etc. comprising the compound represented by the following general formula (1) or its analogue to a patient in need of such treatment:

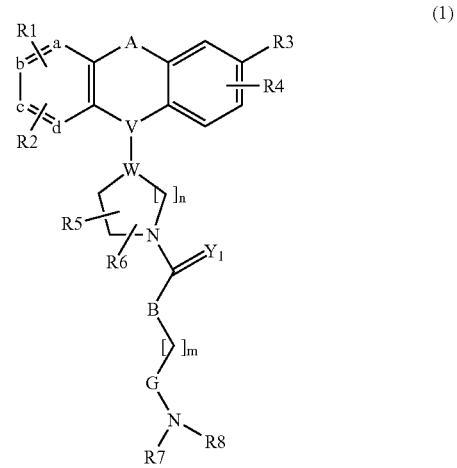

wherein, A represents CH=CH, etc., a, b, c and d represents CH etc., R1, R2, R3, R4, R5 and R6 represents H etc., V—W represents C=C, etc., n represents 0 to 3, Y1 represents O etc., B represents —(CH2)vCHR21 wherein v is 0 to 3, R21 represents H, a lower alkyl group or the like, etc., G represents —CO—, a covalent bond, etc., m is 0 to 6, R7 and R8 represents H, a lower alkyl group, —COR18a, —COOR20 wherein R18a and R20 each represents a lower alkyl group or the like, etc.

23 Claims, 2 Drawing Sheets

OTHER PUBLICATIONS

Timmerman et al. "Preparation of piperidine . . . " CA 126:18791 (1996).

Vega-Hernandez et al. "Down regulation of N-type . . . " Cell and Mol. Neurobiology v.22(2) (2002) p. 185-190.

Sutton et al. "Gabapentin inhibits . . . " Br. J. Pharm. v.135 (2002) p. 257-265.

Japanese Office Action issued May 14, 2012, in corresponding Japanese Patent Application No. 2009-112124 with English Translation (6 pp.).

* cited by examiner

DIARYLALKENE DERIVATIVES AND NOVEL DIARYLALKANE DERIVATIVES

CROSS-REFERENCE TO RELATED APPLICATIONS

The present application is a divisional of U.S. Ser. No. 10/787,175, filed on Feb. 27, 2004, which is a continuation of International Application No. PCT/JP02/08809, filed on Aug. 30, 2002, which claims priority to JP 2001-263718, filed on Aug. 31, 2001, to JP 2002-14387, filed on Jan. 23, 2002, and to JP 2002-111067 filed on Apr. 12, 2002. The contents of the aforementioned applications are incorporated herein by reference.

BACKGROUND OF THE INVENTION

The present invention relates to novel diarylalkene derivatives and the use of the diarylalkene derivatives as medicines. The present invention also relates to novel diarylalkane derivatives and the use of the diarylalkane derivatives as medicines. It was suggested that N-type calcium channel is concerned with various diseases, for example, pain, brain injury caused by ischemia at the acute stage after the onset of cerebral infarction or cerebral hemorrhage (including subarachnoidal hemorrhage) or the like; progressive neurodegenerative diseases such as Alzheimer's disease, AIDS related dementia Parkinson's disease, dementia due to cerebrovascular disorder and ALS; neuropathy caused by head injury; various diseases associated with psychogenic stress such as bronchial asthma, unstable angina and irritable colitis; emotional disorder and withdrawal symptoms after addiction to drugs such as ethanol addiction withdrawal symptoms. The present invention relates to compounds antagonistic to the N-type calcium channel and, therefore usable as therapeutic agents for these diseases.

Calcium channels are now classified into subtypes of L, N, P, Q, R and T. Each subtype of calcium channels is organ-specifically distributed. It is known that particularly N-type calcium channel is widely distributed in central nerves, peripheral nerves and adrenomedullary cells and participates in neuronal cell death, regulation of blood catecholamine level and control of senses such as perception.

Omega conotoxin GVIA and omega conotoxin MVIIA are known as peptides selectively inhibiting N-type calcium channel. It was confirmed in animal tests that omega conotoxin MVIIA relieves a pain induced by formalin, hot plate and peripheral neuropathy (J. Pharmacol. Exp. Ther. 269, 1117-1123, 1994; J. Pharmacol. Exp. Ther. 274, 666-672, 1995). Accordingly, omega conotoxin MVIIA is considered to be clinically effective against pains. It was confirmed that omega conotoxin GVIA and omega conotoxin MVIIA inhibit the release of excitatory neurotransmitters in the sliced brain preparation. It was also confirmed in animal experiments that they inhibit the progress of neuronal cell death associated with cerebrovascular disorders. It is generally considered that compounds antagonistic to the N-type calcium channel are clinically effective in the treatment of brain injury caused by ischemia at the acute stage after the onset of cerebral infarction or cerebral hemorrhage (including subarachnoidal hemorrhage); progressive neurodegenerative diseases such as Alzheimer's disease, AIDS related dementia, Parkinson's disease, dementia due to cerebrovascular disorder and ALS; and neuropathy caused by head injury. In addition, because omega conotoxin GVIA inhibits the release of catecholamine from cultured sympathetic ganglion cells, the contraction of the isolated blood vessel by electric stimulation of the perivascular nerve and catecholamine secretion from canine adrenal medulla, it is considered that compounds antagonistic to N-type calcium channel are clinically effective against various diseases related to psychogenic stress such as bronchial asthma, unstable angina and irritable colitis [Neuropharmacol., 32, 1141 (1993)].

Some peptidergic and non-peptidergic compounds which selectively affect N-type calcium channels have been ever disclosed (see, for example, WO 9313128, WO 9849144, WO 9901438 and WO 9932446). However, none of them was actually used as a medicine. Some of the compounds which affect N-type calcium channels are also effective against various types of calcium channels of other than N-type (Br. J. Pharmacol., 122, 37-42, 1997). For example, compounds having an antagonistic effect on L-type calcium channels, which are very closely related to hypotensive effect, could not be used for assumed diseases for which N-type antagonists will be used (such as cerebral stroke, neuralgia, terminal cancer pain and pain caused by spinal injury). Under these circumstances, the development of a highly active antagonist selective toward N-type calcium channels has been eagerly demanded. In addition, an improvement in QOL (quality of life) of patients is demanded and the development of oral medicines is considered to be necessary.

However, well-known N-type calcium channel antagonists are yet insufficient for solving this problem, since some of them are peptides that cannot be absorbed from the gastrointestinal tracts or some are decomposed in the gastrointestinal tracts because of their chemical instability.

On the other hand, various diarylalkene derivatives and diarylalkane derivatives have been reported (WO 8803138, WO 9510516, WO 9630363, WO 95631478, U.S. Pat. No. 5,994,364 and Japanese Patent Kokai No. Hei 8-291142/1996). However, no literature disclosed that the compounds reported hereinbefore and also diarylalkene derivatives and diarylalkane derivatives analogous to them have a selective antagonistic effect on N-type calcium channel.

Piperidine derivatives having structures similar to those of the compounds of the present invention are reported in Japanese Patent Kokai No. Hei 8-3135/1996. However, it is also described therein that they are antithrombocytic agents which powerfully inhibit serotonin receptor 2, that because of the antagonistic effect on serotonin, they are effective in the treatment of ischemic diseases, migraine, etc. and that because of the antithrombocytic effect, they are effective in the treatment of a pain caused by various ischemic diseases and chronic arterial occlusive disease. However, it is to be noted that the compounds of the present invention are different from the piperidine derivatives disclosed in Japanese Patent Kokai No. Hei 8-3135/1996 because they scarcely have the antagonistic effect on serotonin.

Further, piperidine derivatives having structures similar to those of the compounds of the present invention and effective in the treatment of diseases such as asthma, allergic rhinitis, allergic dermatitis and hives are reported in Japanese Patent Kokai No. Hei 8-291142/1996. However, they are antihistaminic agents or antileukotrienes and essentially different, in the mechanism of the effects, from the N-type calcium channel antagonists directly effective on the neurons to exert the effects on the above-described diseases.

DISCLOSURE OF THE INVENTION

The object of the present invention is to provide new compounds having a selective antagonistic effect on N-type calcium channels.

Another object of the present invention is to provide antagonists to N-type calcium channels.

Still another object of the present invention is to provide a method for treating any diseases of pain, brain injury caused by ischemia at the acute stage after the onset of cerebral infarction or cerebral hemorrhage, Alzheimer's disease, AIDS related dementia, Parkinson's disease, progressive neurodegenerative diseases, neuropathy caused by head injury, bronchial asthma, unstable angina, irritable colitis and withdrawal symptoms after addiction to drugs.

After synthesizing various novel diarylalkene derivatives and diarylalkane derivatives and examining the N-type calcium channel antagonistic effect (determined by fluorescent dye method) and L-type calcium channel antagonistic effect (relaxation response against the KCl-induced contraction of isolated rat thoracic aorta) for the purpose of solving the above-described problems, the inventors have found that specified diarylalkene derivatives and diarylalkane derivatives have an excellent effect of selectively antagonizing N-type calcium channels. The inventors have also found that those compounds have a remarkable therapeutic effect on animal pain models. The present invention has been completed on the basis of these findings. The compounds of the present invention are orally absorbed and have lasting efficacy and thus, they are usable as therapeutic agents for the above-described diseases.

Namely, the present invention provides diarylalkene derivatives or diarylalkane derivatives of the following general formula (1), (2), (3) or (4), or pharmaceutically acceptable salts thereof, and N-type calcium channel antagonists and a pharmaceutical composition comprising one of them as an active ingredient:

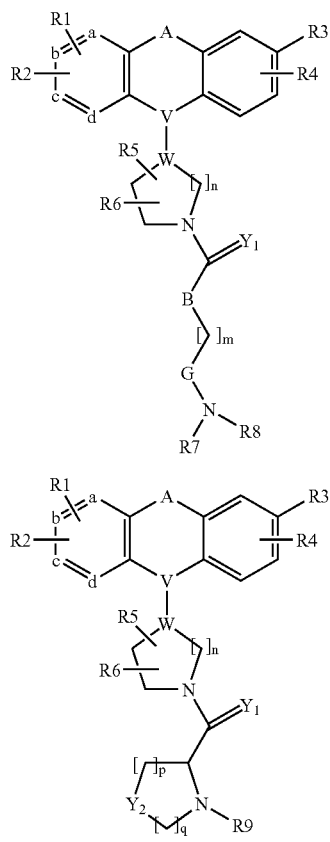

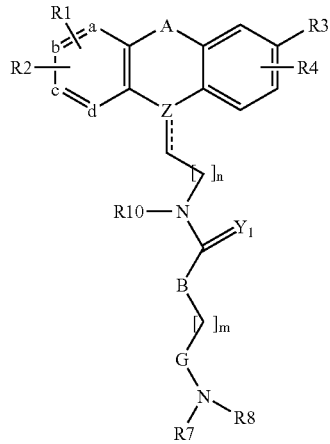

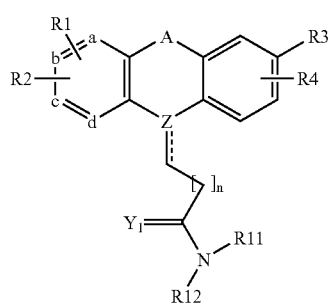

wherein A represents —CH=CH—, —CH$_2$—CH$_2$—, —S—, —CH$_2$—S—, —S—CH$_2$—, —O—, —CH$_2$—O—, —O—CH$_2$—, —N(R$^{17}$)—CH$_2$—, —CH$_2$—N(R$^{17}$)—, —CH=CH—CH$_2$—, —CH$_2$—CH=CH—, —CH$_2$—CH$_2$—CH$_2$—, —N(R$^{17}$)—(CO)—, —(CO)—N(R$^{17}$)—, —(CO)—, —(SO)— or —C(R$^{18}$R$^{19}$)— wherein R$^{17}$ represents H, a lower alkyl or an aryl, and R$^{18}$ and R$^{19}$ are each independently selected from the group consisting of H, a lower alkyl, an aryl and —C(O)OR$^{15}$ wherein R$^{15}$ represents a lower alkyl or an aryl;

a, b, c and d are each independently selected from the group consisting of CR$^1$ and CR$^2$;

or one of a, b, c and d is N;

R$^1$, R$^2$ and R$^4$ each independently represent H, a halogen, —CF$_3$, —OR$^{14}$, —COR$^{14}$, —SR$^{14}$, —S(O)$_t$R$^{15}$, —N(R$^{14}$)$_2$, —NO$_2$, —OC(O)R$^{14}$, —CO$_2$R$^{14}$, —OCO$_2$R$^{14}$, —CN, —NR$^{14}$COOR$^{15}$, —SR$^{15}$C(O)OR$^{15}$ or —SR$^{15}$N(R$^{16}$)$_2$ wherein R$^{14}$ represents H, a lower alkyl, an aryl or an aryl-lower alkyl group, R$^{15}$ represents a lower alkyl or an aryl group, R$^{16}$ is independently selected from the group consisting of H and —C(O)OR$^{15}$, and t represents 1 or 2;

R$^3$ represents H;

V—W represents C=C, CH—CH, CH—N or N—CH;

Z is selected from the group consisting of C, CH and N (with the proviso that when Z is C, the bond represented by a dotted line represents a double bond and when Z is CH or N, the bond represented by the dotted line represents a single bond;

n represents 0 to 3;

R$^5$ and R$^6$ each independently represent H, a halogen, —CF$_3$, a lower alkyl or an aryl;

or R$^5$ and R$^6$ together form =O or =S;

Y$_1$ represents O or S;

B represents $NR^{17a}$, $-NR^{17a}(CH_2)_vCHR^{21}-$, $-(CH_2)_vCHR^{21}-$ wherein v represents 0 to 3, $R^{17a}$ represents H, a lower alkyl or an aryl, $R^{21}$ represents H, a lower alkyl, an aryl, a hydroxyl-lower alkyl, $-CH_2SH$, $-CH_2CH_2SCH_3$, $-CH_2(CO)NH_2$, $-CH_2CH_2(CO)NH_2$, $-(CH_2)_v-COOR^{29}-(CH_2)_v-NR^{29}R^{30}$ wherein $R^{29}$ and $R^{30}$ each independently represent hydrogen atom or a lower alkyl group, and w represents 0 to 4, $-(CH_2)_3NHC(NH_2)=NH$, benzyl, 4-hydroxybenzyl, 3-indoylmethyl or 5-imidazoylmethyl;

G represents $-(CO)-$, $-(SO)-$, $-(SO_2)-$ or a covalent bond;

m represents 0 to 6;

$Y_2$ represents C or S;

p and q are each independently selected from the group consisting of 1, 2 and 3;

$R^7$ and $R^8$ each represent H, a lower alkyl, an aryl, $-(CO)R^{18a}$, $-(CS)R^{18a}$, $(CO)NR^{18a}R^{19a}$, $-(CS)NR^{18a}R^{19a}$ wherein $R^{18a}$ represents H, a lower alkyl, an aryl or a cycloalkyl group which may have a hetero atom in the ring, $R^{19a}$ represents H, a lower alkyl or an aryl; or $R^{18a}$ and $R^{19a}$ together form a cycloalkyl which may have a halogen, $-CF_3$, a lower alkyl or an aryl as a substituent, $-(CO)OR^{20}-(CS)OR^{20}$ or wherein $R^{20}$ represents an alkyl group having 1 to 12 carbon atoms, an aryl group or a cycloalkyl group which may have a hetero atom in the ring, or a group of the following general formula (5):

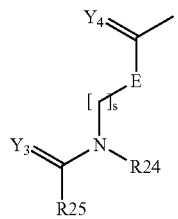

(5)

wherein $Y^4$ and $Y^3$ each represent O or S; s represents 0 to 6;

E represents $NR^{22}$ or $CHR^{23}$ wherein $R^{22}$ represents H, a lower alkyl or aryl; and $R^{23}$ represents H, a lower alkyl, an aryl, a hydroxyl-lower alkyl, $-CH_2SH$, $-CH_2CH_2SCH_3$, $-CH_2(CO)NH_2$, $-CH_2CH_2(CO)NH_2$, $-CH_2COOH$, $CH_2CH_2COOH$, $-(CH_2)_4NH_2$, $-(CH_2)_3NHC(NH_2)=NH$, benzyl, 4-hydroxybenzyl, 3-indoylmethyl or 5-imidazoylmethyl;

$R^{24}$ represents H, a lower alkyl or an aryl;

$R^{25}$ represents H, a lower alkyl, an aryl, $-OR^{18a}$, $-(CO)R^{18a}$, $-(CS)R^{18a}$, $-(CO)NR^{18a}R^{19a}$, $-(CS)NR^{18a}R^{19a}$, $-(CO)OR^{20}$ or $-(CS)OR^{20}$ wherein $R^{18a}$, $R^{19a}$ and $R^{20}$ are as defined above, $R^9$ represents H, a lower alkyl, an aryl, $-(CO)R^{18a}$, $-(CS)R^{18a}$, $-(CO)NR^{18a}R^{19a}$, $-(CS)NR^{18a}R^{19a}$, $-(CO)OR^{20}$ or $-(CS)OR^{20}$ wherein $R^{18a}$, $R^{19a}$ and $R^{20}$ are as defined above;

$R^{10}$ represents H, a lower alkyl or an aryl;

$R^{11}$ represents H, a lower alkyl or an aryl;

$R^{12}$ represents H, a lower alkyl, an aryl, $-(CO)R^{18a}$, $-(CS)R^{18a}$, $-(CO)NR^{18a}R^{19a}$, $-(CS)NR^{18a}R^{19a}$, $-(CO)OR^{20}$ or $-(CS)OR^{20}$ wherein $R^{18a}$, $R^{19a}$ and $R^{20}$ are as defined above, or a substituent represented by the following general formula (6):

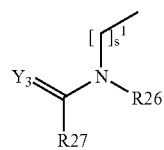

(6)

wherein $s^1$ represents 1 to 6;

$Y^3$ represents O or S, $R^{26}$ represents H, a lower alkyl or an aryl;

$R^{27}$ represents H, a lower alkyl, an aryl, $-OR^{18a}$, $-(CO)R^{18a}$, $-(CS)R^{18a}$, $-(CO)NR^{18a}R^{19a}$, $-(CS)NR^{18a}R^{19a}$, $-(CO)OR^{20}$ or $-(CS)OR^{20}$ wherein $R^{18a}$, $R^{19a}$ and $R^{20}$ are as defined above;

or $R^{11}$ and $R^{12}$ form a substituent represented by the following general formula (7) together with the nitrogen atom:

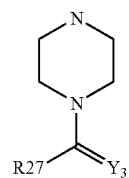

(7)

wherein $Y^3$ represents O or S, and $R^{27}$ is as defined above.

The present invention also provides a method for treating any diseases of pain, brain injury caused by ischemia at the acute stage after the onset of cerebral infarction or cerebral hemorrhage, Alzheimer's disease, AIDS related dementia, Parkinson's disease, progressive neurodegenerative diseases, neuropathy caused by head injury, bronchial asthma, unstable angina, irritable colitis and withdrawal symptoms after addiction to drugs, comprising administrating the above-described diarylalkene derivative or diarylalkane derivative of formula (1), (2), (3) or (4) wherein $R^3$ represents the same group as that defined in $R^4$, and $R^{20}$ represents an alkyl group having 1 to 12 carbon atoms, an aryl group, a cycloalkyl group which may have a hetero atom in the ring or an aryl-lower alkyl group, or a pharmaceutically acceptable salt thereof to a patient in need of such treatment, as the active ingredient. The present invention also provides a method for antagonizing N-type calcium channels comprising administering to a patient in need of such antagonistic action of the above-described derivatives as the active ingredient.

BEST MODE FOR CARRYING OUT THE INVENTION

Figure 1:
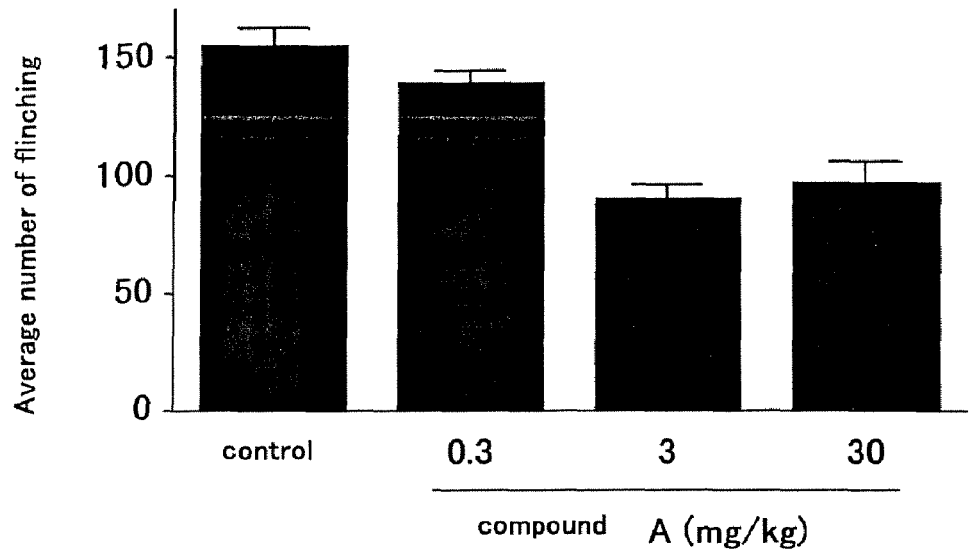
FIG. 1 shows the analgesic effect of compound A in the formalin test.

The term "lower" herein indicates that the group has 1 to 6 carbon atoms. Alkyl groups themselves and also alkyl groups in arylalkyl groups and hydroxyalkyl groups may be either linear or branched. Examples of these alkyl groups are methyl group, ethyl group, propyl group, isopropyl group, butyl group, pentyl group, hexyl group, and secondary and tertiary butyl groups. In them, those having 1 to 4 carbon atoms are preferred. The aryl-lower alkyl groups include, for example, phenyl-lower alkyl groups and naphthyl-lower alkyl groups wherein the aryl part is unsubstituted or substituted with one or two lower alkyl groups, lower alkoxyl groups, halogens, nitro groups or cyano groups. The groups are preferably benzyl and phenylethyl groups. The hetero atoms include nitrogen, oxygen, sulfur, etc. The halogen atoms include fluorine, chlorine, bromine and iodine. In the present specification, the aryl groups are both substituted and unsubstituted aryl groups. They include substituted and unsubstituted phenyl group and naphthyl group. They are preferably phenyl group and monosubstituted or disubstituted phenyl groups, and the substituents are preferably lower alkyl groups, lower alkoxyl groups, halogens, nitro group and cyano group. The cycloalkyl groups include, for example, cyclopentyl group, cyclohexyl group, 1-methylcyclopentyl group and cycloheptyl group. The cycloalkyl groups which may have a hetero atom in the ring include tetrahydropyranyl group, piperidinyl group, pyrrolidinyl group, piperazinyl group, tetrahydrofuranyl group, homopiperidinyl group and morpholinyl group in addition to those described above.

[1]

In the above general formulae (1), (2), (3) and (4), groups represented by A are preferably —CH=CH—, —CH$_2$—CH$_2$—, —S—, —CH$_2$—S— and —S—CH$_2$—. They are particularly preferably —CH=CH—.

Each of a, b, c and d is independently preferably CH.

Each of $R^1$ to $R^4$ is preferably hydrogen atom.

The group represented by V—W is preferably selected from the group consisting of C=C, CH—CH and N—CH. It is particularly preferably C=C.

The group represented by Z is preferably selected from the group consisting of C, CH and N (with the proviso that when Z is C, the bond represented by a dotted line represents a double bond and when Z is CH or N, the bond represented by the dotted line represents a single bond). Z is particularly preferably C.

n preferably represents 1 or 2. It is particularly preferably 2.

Preferably, $R^5$ and $R^6$ are each hydrogen atom or they together form =O.

$Y^1$ preferably represents oxygen atom.

$R^{17a}$ in $NR^{17a}$ and —$NR^{17a}(CH_2)_v CHR^{21}$— represented by B is preferably hydrogen atom, and $R^{21}$ in —$NR^{17a}(CH_2)_v CHR^{21}$— and —$(CH_2)_v CHR^{21}$— is preferably hydrogen atom or hydroxymethyl group. B is particularly preferably —$(CH_2)_v CHR^{21}$—. "v" is preferably 0 to 3, particularly 2 or 3.

The group represented by G is preferably —(CO)— or a covalent bond.

m represents 0 to 6, preferably 0 to 3.

Preferably p and q each independently represent 1, and $Y^2$ represents carbon atom or sulfur atom.

$R^7$ and $R^8$ are preferably hydrogen atom, a lower alkyl, an aryl, $(CO)R^{18a}$, —$(CO)NR^{18a}R^{19a}$ or —$(CO)OR^{20}$. $R^{11a}$ is preferably a lower alkyl, particularly preferably methyl group, ethyl group, isopropyl group or secondary or tertiary butyl group. $R^{19a}$ is preferably hydrogen atom or a lower alkyl group. It is also preferred that $R^{11a}$ and $R^{19a}$ together form a cycloalkyl group. $R^{20}$ is preferably a lower alkyl group, particularly preferably methyl group, ethyl group, isopropyl group or secondary or tertiary butyl group.

Further, $R^7$ and $R^8$ are preferably a group represented by the above general formula (5) wherein s is preferably 0 to 2, E is preferably $CHR^{23}$ wherein $R^{23}$ preferably represents H, and $Y^3$ and $Y^4$ each represent O; $R^{24}$ preferably represents H, and $R^{25}$ preferably represents —$OR^{18a}$ or —$(CO)OR^{20}$;

$R^9$ preferably represents —$(CO)OR^{20}$;

$R^{10}$ preferably represents H;

$R^{11}$ preferably represents H;

$R^{12}$ preferably represents a substituent represented by the above general formula (6) wherein $s^1$ preferably represents 2 or 3; $Y^3$ preferably represents O;

$R^{26}$ preferably represents H; and $R^{27}$ preferably represents —$OR^{18a}$ or —$(CO)OR^{20}$;

or $R^{11}$ and $R^{12}$ preferably represent a substituent represented by the above general formula (7) together with nitrogen atom, wherein $Y^3$ preferably represents O and $R^{27}$ preferably represents —$OR^{18a}$ or —$(CO)OR^{20}$.

[2]

Preferred diarylalkene derivatives, diarylalkane derivatives and pharmaceutically acceptable salts of them are also those of the above general formulae (1), (2), (3) and (4) wherein the group represented by V—W is preferably C=C, CH—CH or N—CH;

Z is selected from the group consisting of C, CH and N (with the proviso that when Z is C, the bond represented by a dotted line represents a double bond and when Z is CH or N, the bond represented by the dotted line represents a single bond);

B represents $NR^{17a}$, $CHR^{21}$ and $CH_2CHR^{21}$ wherein $R^{17a}$ represents H, a lower alkyl or an aryl, $R^{21}$ represents H, a lower alkyl, an aryl, a hydroxyl-lower alkyl, —$CH_2SH$, —$CH_2CH_2SCH_3$, —$CH_2(CO)NH_2$, —$CH_2CH_2(CO)NH_2$, —$CH_2COOH$, —$CH_2CH_2COOH$, —$(CH_2)_4NH_2$, —$(CH_2)_3NHC(NH_2)$=NH, benzyl, 4-hydroxybenzyl, 3-indoylmethyl or 5-imidazoylmethyl;

$R^{18a}$ represents H, a lower alkyl or an aryl, and $R^{19a}$ represents H, a lower alkyl or aryl; or $R^{18a}$ and $R^{19a}$ together form a cycloalkyl group which may have a halogen, —$CF_3$, a lower alkyl or an aryl as a substituent, and $R^{25}$ and $R^{27}$ each represent H, a lower alkyl, an aryl, —$(CO)R^{18a}$, —$(CS)R^{18a}$, —$(CO)NR^{18a}R^{19a}$, —$(CS)NR^{18a}R^{19a}$, —$(CO)OR^{20}$ or —$(CS)OR^{20}$.

[3]

Preferred diarylalkene derivatives, diarylalkane derivatives and pharmaceutically acceptable salts of them are also those of the above general formulae (1), (2), (3) and (4) wherein:

A represents —CH=CH—, —$CH_2$—$CH_2$—, —S—, —$CH_2$—S— or —S—$CH_2$—;

a, b, c and d each represent CH;

$R^3$ and $R^4$ each represent hydrogen atom;

$R^5$ and $R^6$ each represent hydrogen atom;

or $R^5$ and $R^6$ together form =O;

n represents 1 or 2;

$Y^1$ represents O;

B represents $NR^{17a}$, $CHR^{21}$— or, $CH_2CHR^{21}$ wherein $R^{21}$ represents H, a lower alkyl, an aryl or —$CH_2OH$;

G represents —(CO)— or a covalent bond;

m represents 0 to 6;

p and q are each 1;

$R^7$ and $R^8$ each independently represent H, a lower alkyl, an aryl, —$(CO)R^{18a}$ wherein $R^{18a}$ represents H, a lower alkyl or an aryl, —$(CO)NR^{18a}R^{19a}$ wherein $R^{19a}$ represents H, a lower alkyl or an aryl; or $R^{18a}$ and $R^{19a}$ together form a cycloalkyl which may have a halogen, —$CF_3$, a lower alkyl or an aryl as a substituent, —$(CO)OR^{20}$ wherein $R^{20}$ represents an alkyl group having 1 to 12 carbon atoms, an aryl group or a cycloalkyl group which may contain a hetero atom in the ring, or a group of the following general formula (8):

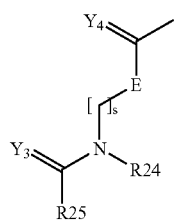

(8)

[wherein $Y^4$ and $Y^3$ each represent O;
represents 1 or 2;
E represents $CHR^{23}$ wherein $R^{23}$ represents H,
$R^{24}$ represents H;
$R^{25}$ represents —(CO)$OR^{20}$;]
$R^9$ represents —(CO)$OR^{20}$;
$R^{10}$ represents H;
$R^{11}$ represents H;
$R^{12}$ represents a substituent represented by the following general formula (9);

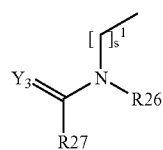

(9)

wherein $s^1$ represents 2 or 3;
$Y^3$ represents O;
$R^{26}$ represents H;
and $R^{27}$ represents —(CO)$OR^{20}$,
or $R^{11}$ and $R^{12}$ form a substituent represented by the following general formula (10) together with the nitrogen atom:

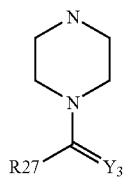

(10)

Preferred diarylalkene derivatives, diarylalkane derivatives and pharmaceutically acceptable salts of them are also those of the general formula (1) wherein A represents —CH=CH— or —CH$_2$—CH$_2$—,
a, b, c and d each represent CH;
$R^1$ and $R^2$ each represent H;
$R^3$ and $R^4$ each represent H;
V—W represents C=C;
n represents 2;
$R^5$ and $R^6$ each represent H; and
$Y^1$ represents O.

[5]
Preferred diarylalkene derivatives, diarylalkane derivatives and pharmaceutically acceptable salts of them are also those of the above general formulae (1), (2), (3) and (4) wherein:
V—W represents C=C, CH—CH or N—CH;
Z is selected from the group consisting of C, CH and N (with the proviso that when Z is C, the bond represented by a dotted line represents a double bond and when Z is CH or N, the bond represented by the dotted line represents a single bond);
B represents —(CH$_2$)$_v$—CHR$^{21}$ wherein v represents 2 or 3,
$R^{21}$ represents H, a lower alkyl, an aryl, a hydroxyl-lower alkyl, —CH$_2$SH, —CH$_2$CH$_2$SCH$_3$, —CH$_2$(CO)NH$_2$, —CH$_2$CH$_2$(CO)NH$_2$, benzyl, 4-hydroxybenzyl, 3-indoylmethyl or 5-imidazoylmethyl;
$R^{18a}$ represents H, a lower alkyl or an aryl, and $R^{19a}$ represents H, a lower alkyl or aryl; or $R^{18a}$ and $R^{19a}$ together form a cycloalkyl group which may have a halogen, —CF$_3$, a lower alkyl or an aryl as a substituent.

[6]
Preferred diarylalkene derivatives, diarylalkane derivatives and pharmaceutically acceptable salts of them are also those of the general formula (1) wherein:
A represents —CH=CH— or —CH$_2$—CH$_2$—,
a, b, c and d each represent CH;
$R^1$, $R^2$, $R^3$, $R^4$, $R^5$ and $R^6$ each represent H;
V—W represents C=C;
m represents 0, n represents 2;
$Y^1$ represents O, G represents a covalent bond, and
$R^7$ and $R^8$ each independently represent H, a lower alkyl, —(CO)$R^{18a}$ wherein $R^{18a}$ represents H, a lower alkyl or an aryl, —(CO)$OR^{20}$ wherein $R^{20}$ represents an alkyl group having 1 to 12 carbon atoms or an aryl.

In the present invention, particularly preferred diarylalkene derivatives, diarylalkane derivatives and pharmaceutically acceptable salts of them in those compounds are those of the general formula (1) wherein:
A represents —CH=CH— or —CH$_2$—CH$_2$—;
a, b, c and d each represent CH;
$R^1$, $R^2$, $R^3$, $R^4$, $R^5$ and $R^6$ each represent H;
V—W represents C=C;
Z represents C, and the bond represented by a dotted line represents a double bond;
n represents 2; and
$Y^1$ represents O.

In the compounds of the general formulae (1) to (4) in the present invention, preferred compounds are those of general formula (1) and more preferred compounds are those having the above-described preferred groups.

[7]
In the compounds of the present invention, diarylalkene derivatives, and diarylalkane derivatives of the following general formula (11) and pharmaceutically acceptable salts thereof are further preferred:

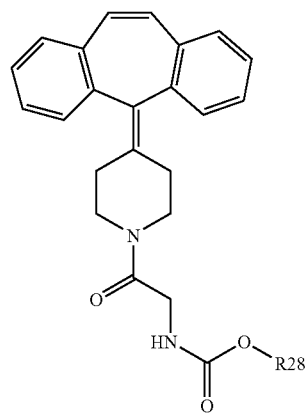

(11)

wherein R$^{28}$ represents an alkyl group having 1 to 12 carbon atoms, a cycloalkyl group having 3 to 12 carbon atoms or a cycloalkyl group which may have a hetero atom in the ring. R$^{28}$ is preferably a branched alkyl group, particularly a branched alkyl group having 3 to 8 carbon atoms.

[8]

In the present invention, diarylalkene derivatives and diarylalkane derivatives of the following general formula (1-A) and pharmaceutically acceptable salts of them are also preferred:

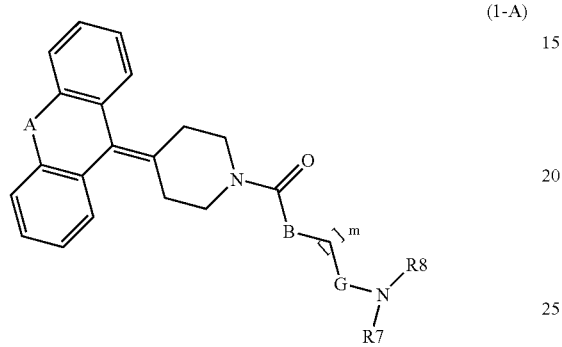

(1-A)

wherein A represents —CH=CH—, —CH$_2$—CH$_2$— or —S—;

B represents —(CH$_2$)$_v$—CHR$^{21}$— wherein v represents 0 to 3, R$^{21}$ represents H, a lower alkyl, an aryl, a hydroxyl-lower alkyl, —(CH$_2$)$_v$—COOR$^{29}$ or —(CH$_2$)$_w$—NR$^{29}$R$^{30}$ wherein R$^{29}$ and R$^{30}$ each independently represent hydrogen atom or a lower alkyl group and w represents 0 to 4;

G represents —(CO)— or a covalent bond;

m represents 0 to 6; and

R$^7$ and R$^8$ each independently represent H, a lower alkyl, an aryl, —(CO)R$^{18a}$ wherein R$^{18a}$ represents H, a lower alkyl, an aryl or a cycloalkyl group which may contain a hetero atom in the ring, or —(CO)OR$^{20}$ wherein R$^{20}$ represents an alkyl group having 1 to 12 carbon atoms, an aryl or a cycloalkyl group which may have a hetero atom in the ring.

[9] [10]

In the present invention, diarylalkene derivatives and diarylalkane derivatives of the following general formulae and pharmaceutically acceptable salts of them are also preferred:

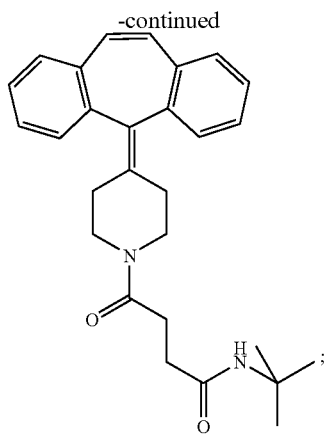

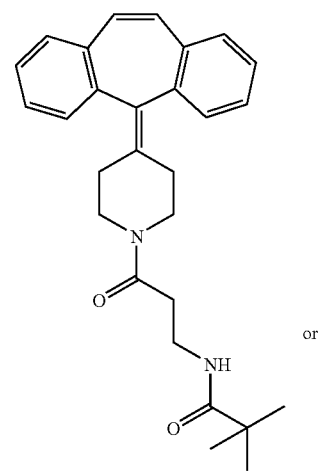

or

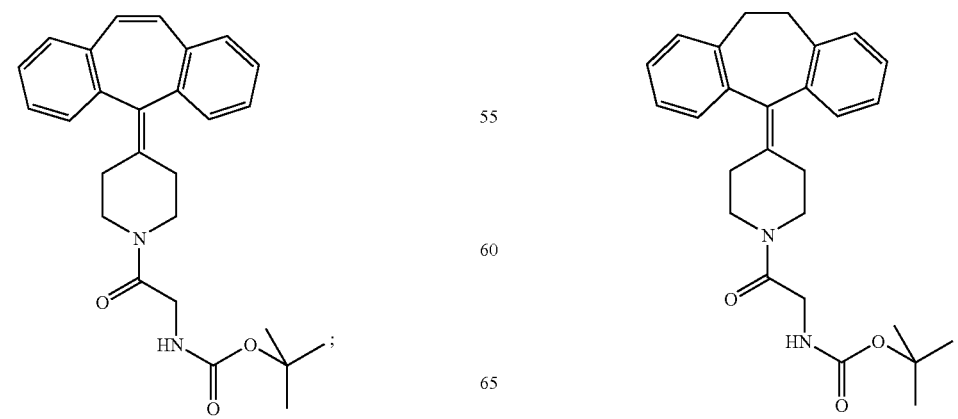

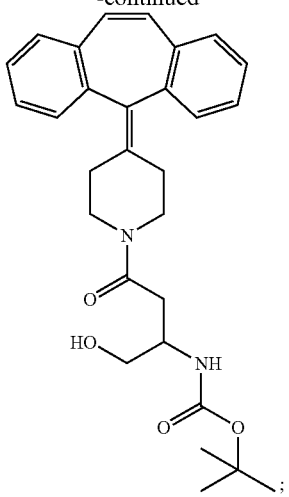
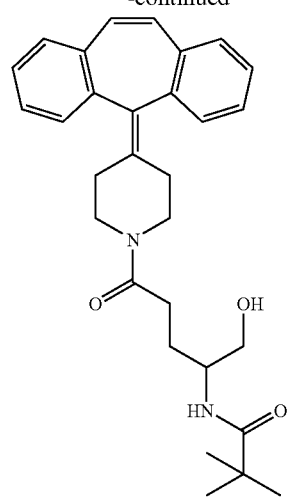
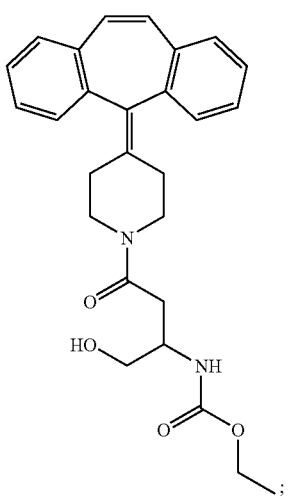
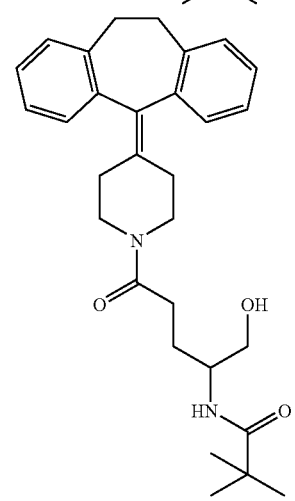
The compounds of the following formulae, analogues of them and pharmaceutically acceptable salts of them are particularly preferred.
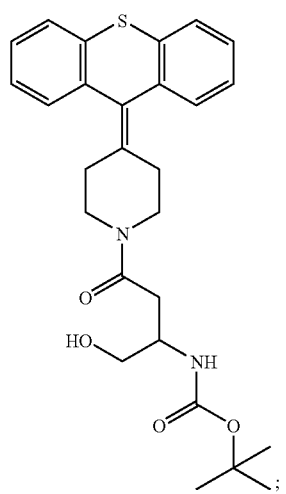
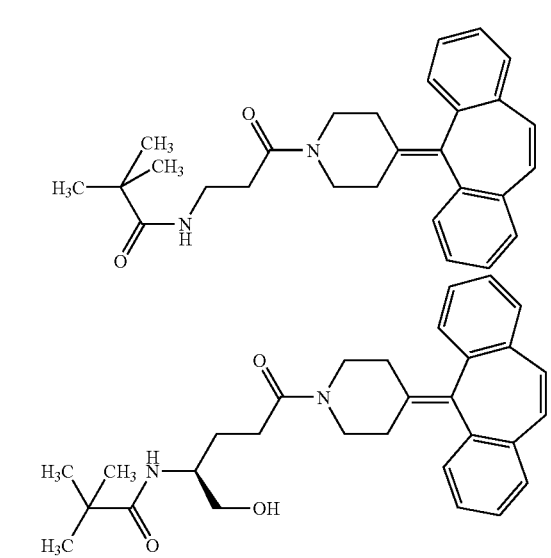

The diarylalkene derivatives and diarylalkane derivatives (1), (2), (3) and (4) of the present invention can be produced by processes described below.

For example, diarylalkene derivatives and diarylalkane derivatives (1-1) and (3-1) of the general formulae (1) and (3) wherein $Y_1$ represents oxygen atom, B represents —$(CH_2)_v$—$CHR^{21}$ and $R^5$ and $R^6$ do not together form oxygen atom or sulfur atom and also diarylalkene derivatives and diarylalkane derivatives (2-1) of the general formula (2) wherein $Y_1$ represents oxygen atom, and $R^5$ and $R^6$ do not together form oxygen atom or sulfur atom can be produced as follows:

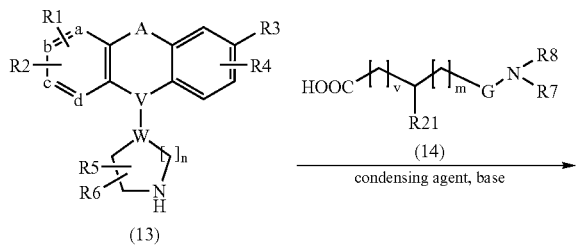

(13)

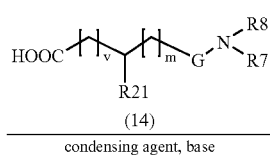

(14)
condensing agent, base

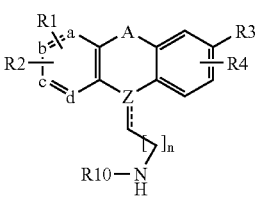

(16)

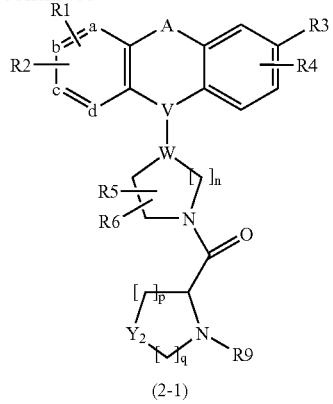

(2-1)

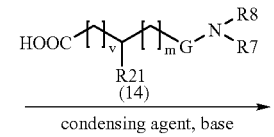

(14)
condensing agent, base

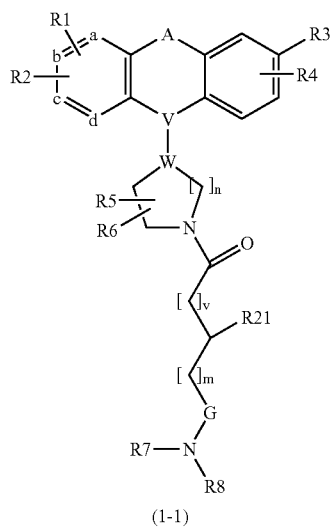

(1-1)

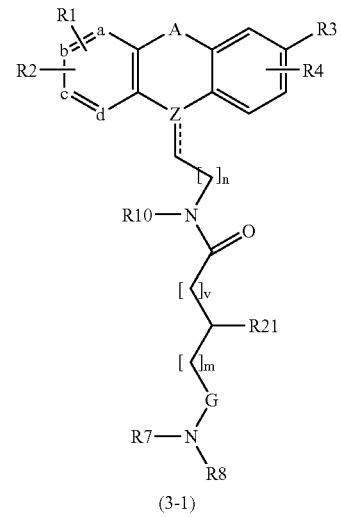

(3-1)

The intended diarylalkene derivatives and diarylalkane derivatives can be obtained by condensing an amine (13) or (16) with a carboxylic acid (14) or (15) in the presence of a base such as triethylamine and a condensing agent such as 1-ethyl-3-(3'-dimethylaminopropyl)carbodiimide or 1,3-dicyclohexylcarbodiimide. 3-(10,11-Dihydro-5H-dibenzo[a,d][7]-annulen-5-ylidene)pyrrolidinie was synthesized according to [Patent: FR1522934]. Compounds (1-1) and (1-3) wherein $R^{21}$ is a hydroxyalkyl group can be obtained by, for example, condensing a compound (14) having an ester corresponding to $R^{21}$ or a compound (14) having protected hydroxyl group and then reducing the ester with a reducing agent such as lithium borohydride or removing the protecting

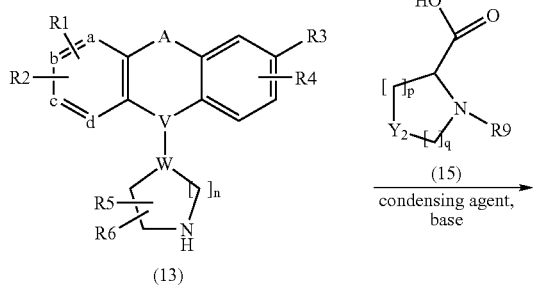

(13)

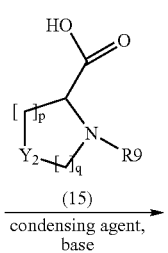

(15)
condensing agent, base group. Compounds (1-1) and (1-3) having carboxyl group in R²¹ can also be obtained by condensing a compound (14) having a corresponding ester as R²¹ and then hydrolyzing the ester with a base such as sodium hydroxide. Compounds (1-1) and (1-3) having a primary or secondary amino group in R²¹ can be obtained by condensing a compound (14) having an amino group protected with, for example, tert-butoxycarbonyl group and then removing the protecting group with an acid or the like.

Diarylalkene derivatives and diarylalkane derivatives (1-2), (1-2'), (3-2) and (3-2') of the general formulae (1) and (3) wherein $Y_1$ represents oxygen atom, B represents $NR^{17a}$ or $-NR^{17a}(CH_2)_vCHR^{21}-$ and $R^5$ and $R^6$ do not together form oxygen atom or sulfur atom can be produced as follows:

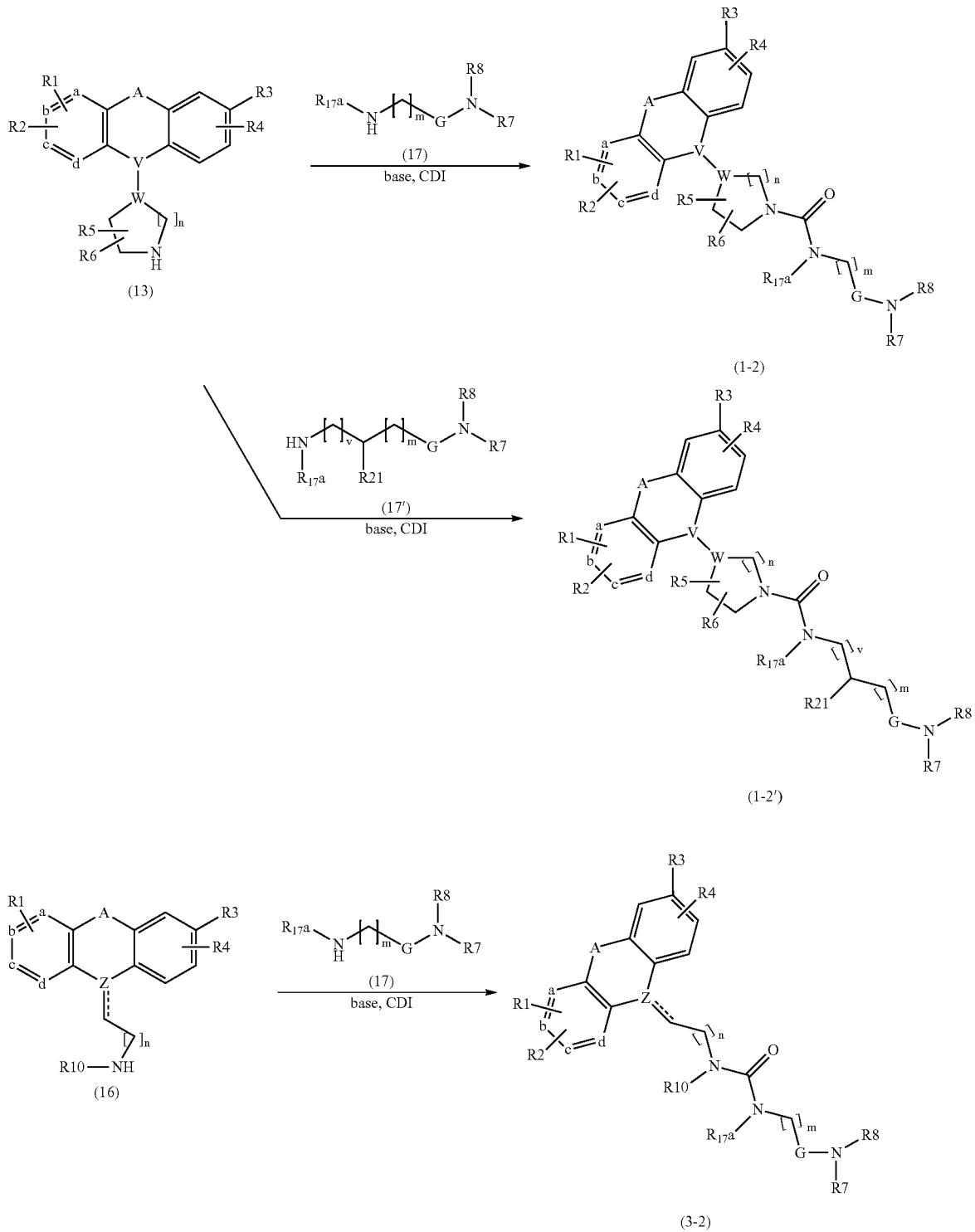

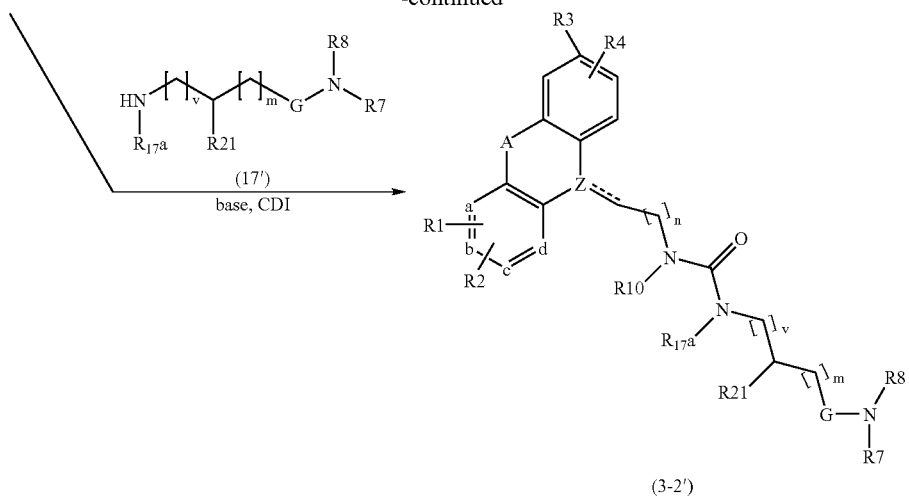

(3-2')

The intended diarylalkene derivatives and diarylalkane derivatives can be obtained by reacting an amine (13) or (16) and an amine (17) or (17') with 1,1'-carbonylbis-1H-imidazole (CDI) in the presence of a base such as triethylamine. Compounds (1-2') and (3-2') wherein $R^{21}$ is a hydroxyalkyl group can be obtained by condensing a compound (17') having a corresponding ester as $R^{21}$ or a compound (17') having protected hydroxyl group and then reducing the ester with a reducing agent such as lithium borohydride or removing the protecting group.

When compounds (1-3) and (3-3) have t-butoxycarbonyl group (Boc group) as shown below, they can be converted into amines (1-4) and (3-4) by using an acid such as trifluoroacetic acid or hydrochloric acid. Also, they can be acylated with an acylating agent such as an acid chloride, an acid anhydride, a chloroformic ester or carbamoyl chloride in the presence of a base such as triethylamine to obtain diarylalkene derivatives and diarylalkane derivatives of formulae (I-5) and (3-5):

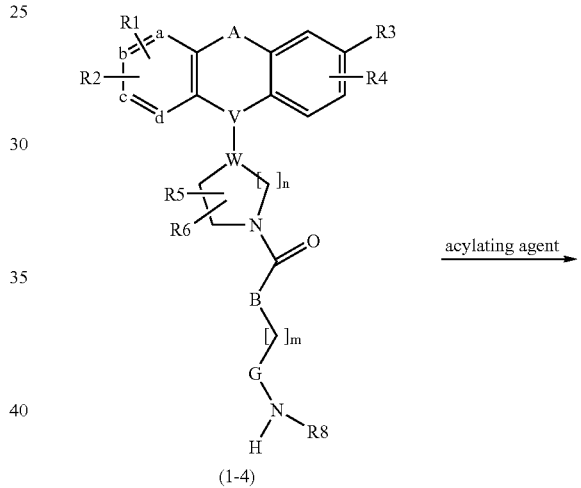

(1-4)

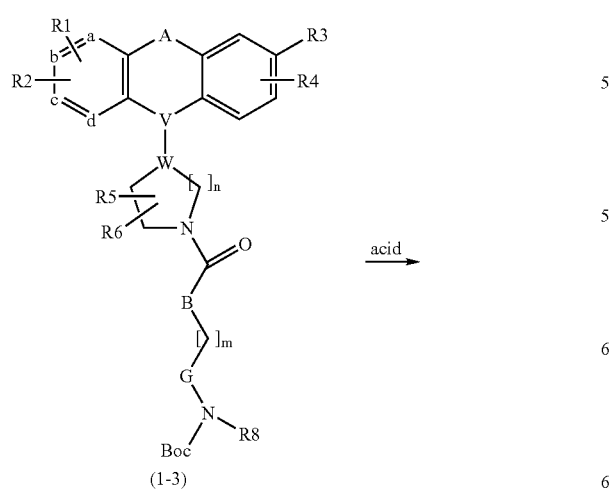

(1-3)

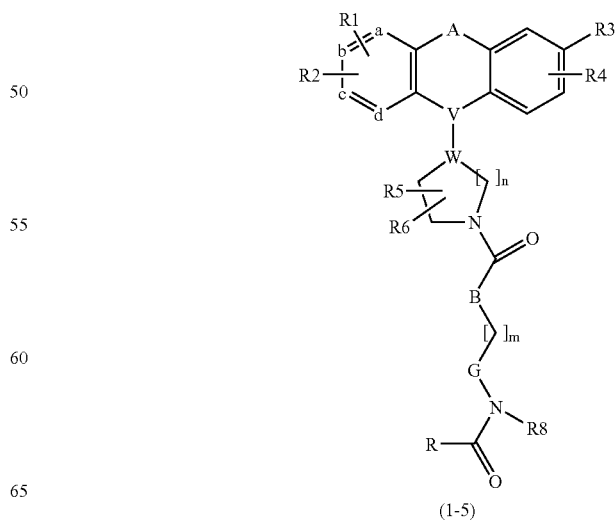

(1-5)

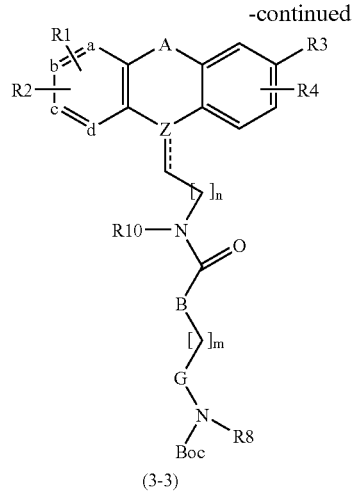

(3-3)

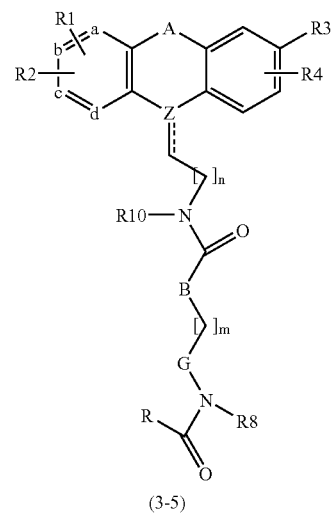

(3-5)

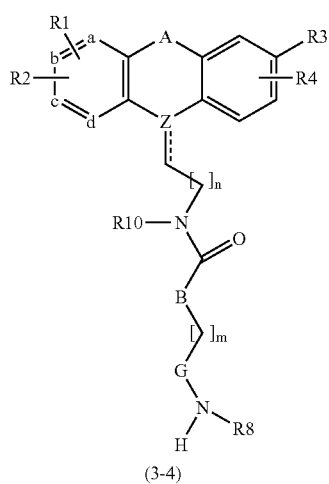

(3-4)

Diarylalkane derivatives (1-6) of the general formula (1) wherein $Y_1$ represents oxygen atom, B represents —$(CH_2)_v$—$CHR^{21}$—, V=W represents N—C, n represents 2 and $R^5$ and $R^6$ do not together form oxygen atom or sulfur atom can be produced as shown in the following reaction scheme wherein X represents a halogen such as I, Br or Cl, or a sulfonyloxyl group such as methanesulfonyloxyl group, trifluoromethanesulfonyloxyl group or p-toluenesulfonyloxyl group:

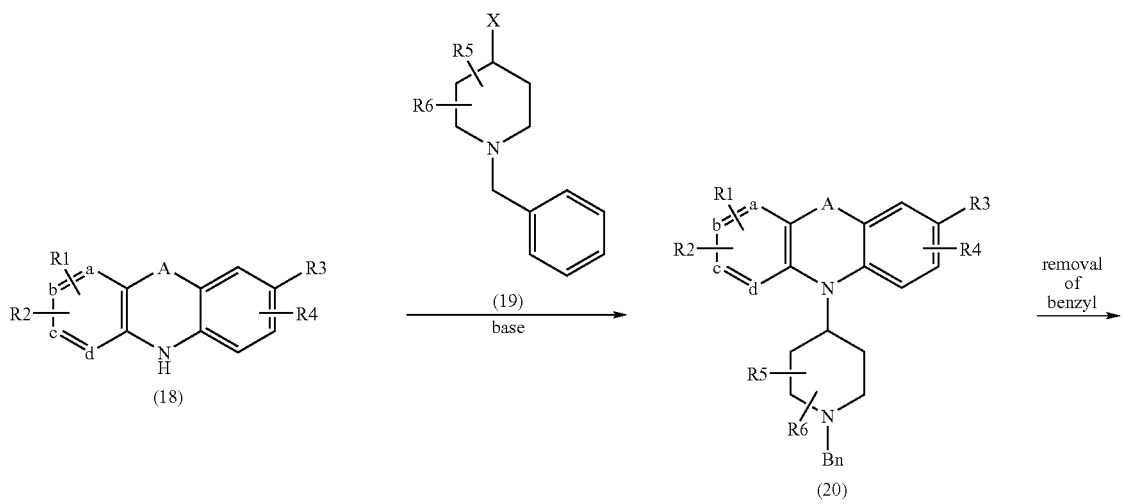

-continued

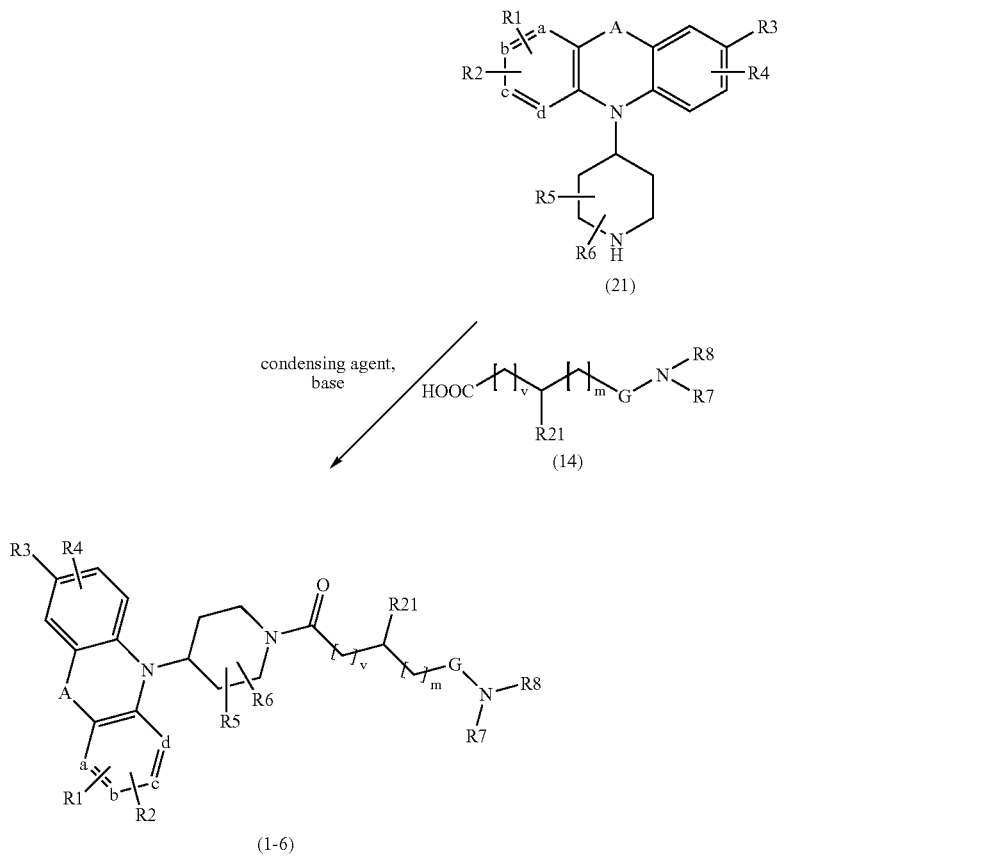

Tertiary aniline derivatives such as those represented by formula (20) can be obtained by reacting an aniline derivative (18) with a sulfonic acid ester or a halide (19) in the presence of a base such as sodium hydride or lithium diisopropylamide. Secondary amines (21) can be obtained by removing benzyl from the compounds (20) in the presence of a catalyst such as palladium carbon, palladium hydroxide carbon or Raney nickel. By condensing the secondary amines (21) with a carboxylic acid (14) in the presence of a base such as triethylamine and a condensing agent such as 1-ethyl-3-(3'-dimethylaminopropyl)carbodiimide or 1,3-dicyclohexylcarbodiimide, the intended diarylalkene derivatives and diarylalkane derivatives can be obtained. The compounds (1-6) wherein $R^{21}$ represents a hydroxyalkyl group can be produced by condensing a compound (14) having an ester corresponding to $R^{21}$ or a compound (14) having protected hydroxyl group and then reducing the ester with a reducing agent such as lithium borohydride or removing the protecting group.

When $Y_1$ in (4) is oxygen atom, the intended diarylalkene derivatives and diarylalkane derivatives (4-1) can be obtained by, for example, condensing a carboxylic acid (22) with an amine (23) in the presence of a base such as triethylamine and a condensing agent such as 1-ethyl-3-(3'-dimethylaminopropyl)carbodiimide or 1,3-dicyclohexylcarbodiimide.

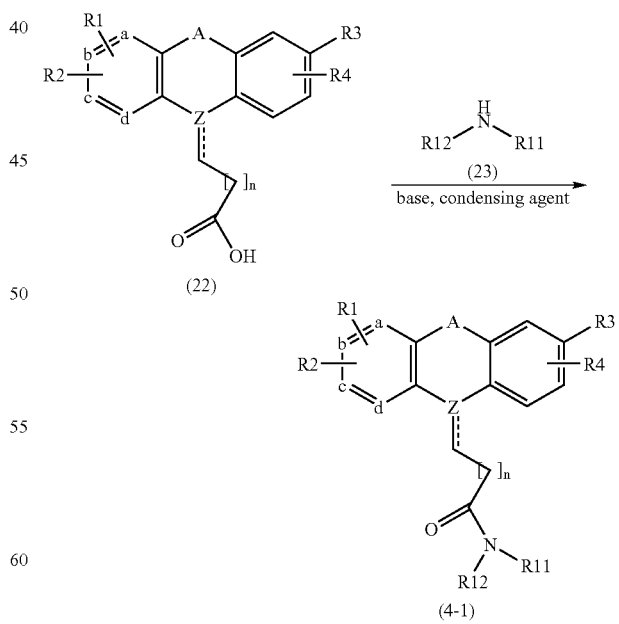

In the compounds (22), those (24) wherein Z is C and n is 0 can be synthesized by, for example, the following reaction scheme:

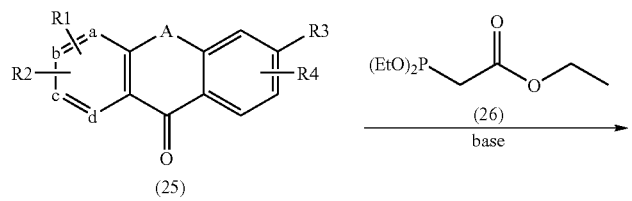 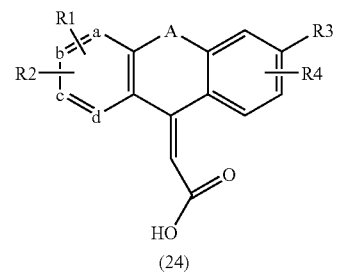

The intended compounds (24) can be obtained by, for example, condensing a ketone (25) with ethyl diethylphosphonoacetate (26) in the presence of a base such as sodium hydride or lithium diisopropylamide.

When the compounds of general formulae (1), (2), (3) and (4) of the present invention can form salts thereof, the salts are pharmaceutically acceptable salts such as ammonium salts, salts thereof with alkali metals, e.g. sodium and potassium, salts thereof with alkaline earth metals, e.g. calcium and magnesium, salts thereof with aluminum or zinc, salts thereof with organic amines, e.g. morpholine, piperidine and dicyclohexylamine, salts thereof with basic amino acids, e.g. arginine and lysine, salts thereof with inorganic acids, e.g. hydrochloric acid, sulfuric acid and phosphoric acid, and salts thereof with organic acids, e.g. oxalic acid, maleic acid, tartaric acid, acetic acid, lactic acid, fumaric acid, citric acid, methanesulfonic acid, p-toluenesulfonic acid and benzenesulfonic acid.

The compounds of the present invention also include solvates such as hydrates and alcohol adducts of the compounds represented by the general formula (1), (2), (3) or (4).

When the compounds of the present invention contain asymmetric carbon atom, it is possible that the compounds are optical isomers. The compounds of the present invention include the optical isomers thereof. When the compounds have diastereomers, those diastereomers and also diastereomer mixtures are also included. When the compounds may have tautomers, those tautomers are also included. Further, geometrical isomers of the compounds are also included.

The compounds of the general formulae (1), (2), (3) and (4) and salts thereof are administered as they are or in the form of various medicinal compositions thereof to the patients. The dosage forms of the medicinal compositions are, for example, tablets, powders, pills, granules, capsules, suppositories, solutions, sugar-coated tablets and depots. They can be prepared with ordinary preparation assistants by an ordinary method. For example, the tablets are prepared by mixing the diarylalkene derivative or diarylalkane derivative, the active ingredient of the present invention, with any of known adjuvants such as inert diluents, e.g. lactose, calcium carbonate and calcium phosphate; binders, e.g. acacia, corn starch and gelatin; extending agents, e.g. alginic acid, corn starch and pre-gelatinized starch; sweetening agents, e.g. sucrose, lactose and saccharin; corrigents, e.g. peppermint, gaultheria leaves oil and cherry; and lubricants, e.g. magnesium stearate, talc and carboxymethyl cellulose.

The N-type calcium channel antagonist containing one of the compounds of the above general formulae (1), (2), (3) and (4) or one of salts thereof as active ingredient is usable as a therapeutic agent for various diseases, for example, pain [such as neuropathic pain (e.g. diabetic neuropathy, postherpetic neuralgia, trigeminal neuralgia and complex regional pain syndrome), migraine, visceral pain, cancer pain, post-operative pain, back pain, HIV-related pain, arthritic pain and pain caused by spinal injury or diabetes]; brain injury caused by ischemia at the acute stage after the onset of cerebral infarction or cerebral hemorrhage (including subarachnoidal hemorrhage); progressive neurodegenerative diseases such as Alzheimer's disease, AIDS related dementia, Parkinson's disease, dementia due to cerebrovascular disorder and ALS; neuropathy caused by head injury; various diseases associated with psychogenic stress such as bronchial asthma, unstable angina and irritable colitis; emotional disorder and withdrawal symptoms after addiction to drugs such as ethanol addiction withdrawal symptoms. In particular, the above-described antagonists are useful as therapeutic agents for pain.

The dose of the compounds or salts thereof used for the above-described purpose varies depending on the intended therapeutic effect, administration method, period of the treatment, and age and body weight of the patient. The dose is usually 1 μg to 5 g a day for adults in the oral administration, and 0.01 μg to 1 g a day for adults in the parenteral administration.

EXAMPLES

The following Examples will further illustrate the present invention, which by no means limit the invention.

Example 1

Synthesis of t-butyl 2-[4-(5H-dibenzo[a,d][7]annulen-5-ylidene)-1-piperidinyl]-2-oxoethylcarbamate 3.00 g (10.9 mmol) of 4-(5H-dibenzo[a,d][7]annulen-5-ylidene)-1-piperidine, 2.29 g (13.2 mmol) of N-t-butoxycarbonylglycine, 3.14 g (16.4 mmol) of 1-ethyl-3-(3'-dimethylaminopropyl)carbodiimide hydrochloride and 122 mg (1.00 mmol) of 4-dimethylaminopyridine were dissolved in 50 ml of dichloromethane. 2.20 g (3.04 mmol) of triethylamine was added to the obtained solution, and they were stirred overnight. Saturated aqueous sodium hydrogencarbonate solution was added to the obtained mixture. After extracting with dichloromethane 3 times, the organic layer was washed with saturated aqueous sodium chloride solution. After drying over anhydrous sodium sulfate, the solvent was evaporated under reduced pressure, and the residue was purified by the silica gel chromatography (hexane:ethyl acetate=4:1 to 2:1) to obtain the title compound.

Yield: 4.29 g (10.2 mmol), 94%

MS (ESI, m/z) 431 (M+H)$^+$ $^1$H-NMR (CDCl$_3$): 1.44 (9H, s), 2.15-2.35 (4H, m), 3.02 (2H, m), 3.42 (1H, m), 3.81-4.01 (3H, m), 5.51 (1H, br s), 6.92 (2H, s), 7.15-7.38 (8H, m).

Example 2

Synthesis of 2-[4-(5H-dibenzo[a,d][7]annulen-5-ylidene)-1-piperidinyl]-2-oxo-ethanamine hydrochloride:

1.40 g (3.25 mmol) of t-butyl 2-[4-(5H-dibenzo[a,d][7]annulen-5-ylidene)-1-piperidinyl]-2-oxoethylcarbamate was dissolved in 20 ml of 1,4-dioxane. 12 ml of 4 N hydrochloric acid/1,4-dioxane solution was added to the obtained solution, and they were stirred overnight. After the neutralization with 4 N aqueous sodium hydroxide solution, the solvent was evaporated under reduced pressure. Saturated aqueous sodium chloride solution was added to the reaction mixture. After the extraction with ethyl acetate 3 times, the extract was dried over anhydrous sodium sulfate and then the solvent was evaporated under reduced pressure. 10 ml of a solution of ethyl acetate:hexane (1:2) and then 2 ml of 4 N hydrochloric acid/1,4-dioxane solution were added to the residue. The resultant precipitates were taken by the filtration, washed with a solution of ethyl acetate:hexane (1:2) and air-dried. After further drying under reduced pressure, the title compound was obtained.

Yield: 1.15 g (3.06 mmol), 94%
MS (ESI, m/z) 415 (M+H+DMSO-$d_6$)$^+$
$^1$H-NMR (CDCl$_3$) (free): 2.12-2.36 (4H, m), 2.36 (2H, s), 2.76-3.12 (2H, m), 3.13-3.50 (3H, m), 3.88-4.00 (1H, m), 6.92 (2H, s), 7.12-7.38 (8H, m).

Example 3

Synthesis of Ethyl 2-[4-(5H-dibenzo[a,d][7]annulen-5-ylidene)-1-piperidinyl]-2-oxoethylcarbamate 375 mg (1.00 mmol) of 2-[4-(5H-dibenzo[a,d][7]annulen-5-ylidene)-1-piperidinyl-2-oxoethanamine hydrochloride was dissolved in 3 ml of dichloromethane. 303 mg (3.00 mmol) of triethylamine was added to the obtained solution. Then a solution of 130 mg (1.20 mmol) of ethyl chloroformate in 3 ml of dichloromethane was slowly added to the reaction mixture. After stirring overnight, saturated aqueous sodium hydrogencarbonate solution was added thereto. After extracting with ethyl acetate twice followed by drying under anhydrous sodium sulfate, the solvent was evaporated under reduced pressure. The residue was roughly purified by the silica gel chromatography (dichloromethane:methanol=98:2) and then purified by the silica gel chromatography (hexane:ethyl acetate=1:2) to obtain the title compound.

Yield: 213 mg (0.528 mmol), 53%
MS (ESI, m/z) 403 (M+H)$^+$
$^1$H-NMR (CDCl$_3$): 1.24 (3H, t), 2.12-2.36 (4H, m), 2.97-3.10 (2H, m), 3.38-3.50 (2H, m), 3.86-4.02 (3H, m), 4.13 (2H, q), 5.65 (1H, br s), 6.92 (2H, s), 7.14-7.20 (2H, m), 7.23-7.38 (6H, m).

Example 4

Synthesis of t-butyl (1S)-1-{[4-(5H-dibenzo[a,d]annulen-5-ylidene)-1-piperidinyl]carbonyl}-3-methylbutylcarbamate 100 mg (0.366 mmol) of 4-(5H-dibenzo[a,d]annulen-5-ylidene)-1-piperidine, 109 mg (0.439 mmol) of N-t-butoxycarbonyl-(L)-leucine, 105 mg (0.549 mmol) of 1-ethyl-3-(3'-dimethylaminopropyl)carbodiimide hydrochloride and 5 mg (0.04 mmol) of 4-dimethylaminopyridine were dissolved in 2 ml of dichloromethane. 74 mg (0.73 mmol) of triethylamine was added to the obtained solution, and they were stirred overnight. Saturated aqueous sodium hydrogencarbonate solution was added to the obtained mixture. After extracting with ethyl acetate 3 times, the organic layer was washed with saturated aqueous sodium chloride solution. After drying over anhydrous sodium sulfate, the solvent was evaporated under reduced pressure, and the residue was purified by the silica gel chromatography (hexane:ethyl acetate=84:16 to 75:25) to obtain the title compound.

Yield: 29.5 mg (0.065 mmol), 17%
MS (ESI, m/z) 487 (M+H)$^+$
$^1$H-NMR (CDCl$_3$): 0.84-0.99 (6H, m), 1.23-1.31 (2H, m), 1.41 (9H, d), 1.70 (1H, m), 2.10-2.40 (4H, m), 2.90-3.20 (2H, m), 3.61 (1H, m), 3.94 (1H, m), 4.62 (1H, m), 5.28 (1H, d), 6.92 (2H, d), 7.14-7.38 (8H, m).

Example 5

Synthesis of (1R)—N-{2-[4-(5H-dibenzo[a,d][7]annulen-5-ylidene)-1-piperidinyl]-2-oxoethyl}-2,2-dimethylcyclopropane carboxyamide 200 mg (0.542 mmol) of 2-[4-(5H-dibenzo[a,d][7]annulen-5-ylidene)-1-piperidinyl]-2-oxoethanamine hydrochloride was dissolved in 1.5 ml of dichloromethane. 137 mg (1.36 mmol) of triethylamine was added to the obtained solution. Then a solution of 86.1 mg (0.650 mmol) of (S)-2,2-dimethylcyclopropanecarboxylic acid chloride in 0.5 ml of dichloromethane was slowly added to the obtained mixture. After stirring for 1 hour, the obtained mixture was roughly purified by the silica gel chromatography (dichloromethane:methanol=98:2) and then purified by the silica gel chromatography (Chromatorex™ NH, Fuji Silysia Chemical LTD., hexane:ethyl acetate=92:8 to 1:4) to obtain the title compound.

Yield: 154 mg (0.362 mmol), 67%
MS (ESI, m/z) 427 (M+H)$^+$
$^1$H-NMR (CDCl$_3$): 0.73 (1H, m), 1.04-1.19 (7H, m), 1.36 (1H, m), 2.12-2.36 (4H, m), 2.96-3.12 (2H, m), 3.40-3.52 (1H, m), 3.80-4.16 (3H, m), 6.65 (1H, bs), 6.92 (2H, s), 7.13-7.20 (2H, m), 7.21-7.40 (6H, m).

Example 6

Synthesis of (1R)—N-{2-[4-(10,11-dihydro-5H-dibenzo[a,d][7]annulen-5-ylidene)-1-piperidinyl]-2-oxoethyl}-2,2-dimethylcyclopropane carboxyamide 72.8 mg of palladium carbon (10% w/v) was added to 72.8 mg (0.171 mmol) of (1R)—N-{2-[4-(5H-dibenzo[a,d][7]annulen-5-ylidene)-1-piperidinyl]-2-oxoethyl}-2,2-dimethyl-cyclopropanecarboxyamide in 10 ml of ethanol, and they were stirred at 4.0 MPa in hydrogen gas atmosphere overnight. After the filtration, the solvent was evaporated under reduced pressure to obtain the title compound.

Yield: 67.1 mg (0.157 mmol), 92%
MS (ESI, m/z) 429 (M+H)$^+$
$^1$H-NMR (CDCl$_3$): 0.75 (1H, dd), 1.05-1.41 (7H, m), 1.37 (1H, dd), 2.30-2.51 (4H, m), 2.35-2.82 (2H, m), 3.09-3.24 (2H, m), 3.31-3.46 (2H, m), 3.48-3.60 (1H, m), 4.00-4.19 (3H, m), 6.68 (1H, br s), 7.00-7.04 (2H, m), 7.04-7.18 (6H, m).

Example 8

Synthesis of N-{2-[4-(5H-dibenzo[a,d][7]annulen-5-ylidene)-1-piperidinyl]-2-oxoethyl}-2,2-dimethylpropanamide 100 mg (0.271 mmol) of 2-[4-(5H-dibenzo[a,d][7]annulen-5-ylidene)-1-piperidinyl]-2-oxoethanamine hydrochloride was dissolved in 1 ml of dichloromethane. 82.3 mg (0.813 mmol) of triethylamine was added to the obtained solution. A solution of 39.2 mg (0.325 mmol) of pivaloyl chloride in 0.5 ml of dichloromethane was slowly added to the obtained mixture. After stirring for 30 minutes, the obtained product was purified by the silica gel chromatography (hexane:ethyl acetate=9:1 to 3:1).

Yield: 62.9 mg (0.152 mmol) (56%)
MS (ESI, m/z) 415 $(M+H)^+$
$^1$H-NMR (CDCl$_3$): 1.21 (9H, s), 2.14-2.35 (4H, m), 2.98-3.12 (2H, m), 3.40-3.53 (1H, m), 3.88-4.09 (3H, m), 6.83 (1H, br s), 6.92 (2H, s), 7.12-7.22 (2H, m), 7.22-7.40 (6H, m).

Example 9

Synthesis of N-(t-butyl)-4-[4-(5H-dibenzo[a,d][7]annulen-5-ylidene)-1-piperidinyl]-4-oxobutanamide 100 mg (0.268 mmol) of 4-[4-(5H-dibenzo[a,d][7]annulen-5-ylidene)-1-piperidinyl]-4-oxobutanoic acid, 23.5 mg (0.321 mmol) of t-butylamine, 3 mg (0.03 mmol) of 4-dimethylaminopyridine and 77.1 mg (0.402 mmol) of 1-ethyl-3-(3'-dim ethylaminopropyl)carbodiimide hydrochloride were dissolved in 1 ml of dichloromethane. 35.2 mg (0.348 mmol) of triethylamine was added to the obtained solution, and they were stirred overnight. The obtained product was purified by the silica gel chromatography (hexane:ethyl acetate=2:1 to 4:6) to obtain the title compound.

Yield: 33.3 mg (0.078 mmol), 29%
MS (ESI, m/z) 429 $(M+H)^+$
$^1$H-NMR (CDCl$_3$): 1.32 (9H, s), 2.08-2.36 (4H, m), 2.41 (2H, t), 2.50-2.71 (2H, m), 2.24-2.96 (2H, m), 3.58 (1H, m), 3.93 (1H, m), 5.77 (1H, br s), 6.92 (2H, s), 7.14-7.38 (8H, m).

Example 10

Synthesis of N-{2-[4-(5H-dibenzo[a,d][7]annulen-5-ylidene)-1-piperidinyl]-2-oxoethyl}-2-methyl-1-propanamine hydrochloride 128.5 mg (0.264 mmol) of t-butyl 2-[4-(5H-dibenzo[a,d][7]annulen-5-ylidene)-1-piperidinyl]-2-oxoethyl(isobutyl) carbamate was dissolved in 1 ml of 1,4-dioxane. 0.5 ml of 4 N hydrochloric acid/1,4-dioxane solution was added to the obtained solution, and they were stirred overnight. Saturated aqueous sodium hydrogencarbonate solution was added to the reaction mixture. After the extraction with ethyl acetate 3 times, the extract was dried over anhydrous sodium sulfate and then the solvent was evaporated under reduced pressure. The residue was purified by the silica gel chromatography (hexane:ethyl acetate=89:11 to 65:35). The solvent was evaporated under reduced pressure, and the residue was dissolved in 2 ml of diethyl ether. 4 N hydrochloric acid/ethyl acetate solution was added to the obtained solution. The precipitates thus formed were taken by the filtration and then washed with diethyl ether. After drying under reduced pressure, the title compound was obtained.

Yield: 102.6 mg (0.242 mmol) 92%
MS (ESI, m/z) 387 $(M+H)^+$
$^1$H-NMR (CDCl$_3$): 1.08 (6H, d), 2.10-2.40 (5 h, m), 2.70-3.10 (4H, m), 3.41 (1H, br s), 3.69-4.10 (3H, m), 6.92 (2H, s), 7.10-7.21 (2H, m), 7.23-7.39 (6H, m), 9.03 (1H, br s), 9.68 (1H, br s).

Example 11

Synthesis of N-{3-[4-(5H-dibenzo[a,d][7]annulen-5-ylidene)-1-piperidinyl]-3-oxopropyl}-2,2-dimethylpropanamide:

Step 1

Synthesis of N-(2,2-dimethylpropanoyl)-β-alanine 558 mg (4.03 mmol) of methy 3-aminopropionate was dissolved in 20 ml of 1 N aqueous sodium hydroxide solution. 362 mg (3.00 mmol) of pivaloyl chloride was immediately added to the obtained solution, and they were stirred for 4 hours. 15 ml of 2 N aqueous hydrochloric acid was added to the reaction mixture. After extracting with ethyl acetate 3 times followed by drying under anhydrous sodium sulfate, the solvent was evaporated under reduced pressure to obtain the title compound.

Yield: 173 mg (0.929 mmol), 23%
$^1$H-NMR (CDCl$_3$): 1.18 (9H, s), 2.60 (2H, t), 3.51 (2H, q), 6.34 (1H, br s).

Step 2

Synthesis of N-{3-[4-(5H-dibenzo[a,d][7]annulen-5-ylidene)-1-piperidinyl]-3-oxopropyl}-2,2-dimethylpropanamide 275 mg (1.01 mmol) of [4-(5H-dibenzo[a,d][7]annulen-5-ylidene)-1-piperidine, 90.0 mg (0.480 mmol) of N-(2,2-dimethylpropanoyl)-β-alanine, 193 mg (1.01 mmol) of 1-ethyl-3-(3'-dimethylaminopropyl)carbodiimide hydrochloride and 6 mg (0.05 mmol) of 4-dimethylaminopyridine were dissolved in 3 ml of dichloromethane. 152 mg (1.50 mmol) of triethylamine was added to the obtained solution. After stirring for 3 hours, the obtained mixture was roughly purified by the silica gel chromatography (Chromatorex™ NH, Fuji Silysia Chemical LTD., hexane:ethyl acetate=89:11 to 7:3) and then purified by the silica gel chromatography (hexane:ethyl acetate=2:3 to 1:4) to obtain the title compound.

Yield: 147 mg (0.343 mmol), 72%
MS (ESI, m/z) 429 $(M+H)^+$
$^1$H-NMR (CDCl$_3$): 1.16 (9H, s), 2.11-2.36 (4H, m), 2.48 (2H, q), 2.94-3.12 (2H, m), 3.52 (3H, q), 3.84-4.00 (1H, m), 6.62 (1H, t), 6.92 (2H, s), 7.13-7.20 (2H, m), 7.22-7.38 (6H, m).

Example 12

Synthesis of N-{2-[4-(5H-dibenzo[a,d][7]annulen-5-ylidene)-1-piperidinyl]-2-oxoethyl}-3,3-dimethylbutanamide 80.0 mg (0.217 mmol) of 2-[4-(5H-dibenzo[a,d][7]annulen-5-ylidene)-1-piperidinyl]-2-oxoethanamine hydrochloride was dissolved in 1 ml of dichloromethane. 75.9 mg (0.750 mmol) of triethylamine was added to the obtained solution. Then a solution of 35.1 mg (0.260 mmol) of 3,3-dimethylbutanoyl chloride in 0.5 ml of dichloromethane was slowly added to the obtained mixture. After stirring for 30 minutes, the product was purified by the silica gel chromatography (hexane:ethyl acetate=93:7 to 3:1) to obtain the title compound.

Yield: 80.1 mg (0.187 mmol), 86%

MS (ESI, m/z) 429 (M+H)$^+$ $^1$H-NMR (CDCl$_3$): 1.03 (9H, s), 2.12 (2H, s), 2.15-2.39 (4H, m), 2.96-3.11 (2H, m), 3.40-3.54 (1H, m), 3.88-4.13 (3H, m), 6.49 (1H, br s), 6.92 (2H, s), 7.14-7.21 (2H, m), 7.21-7.41 (6H, m).

Example 13

Synthesis of isopropyl 2-[4-(5H-dibenzo[a,d][7]annulen-5-ylidene)-1-piperidinyl]-2-oxoethylcarbamate 80.0 mg (0.217 mmol) of 2-[4-(5H-dibenzo[a,d][7]annulen-5-ylidene)-1-piperidinyl]-2-oxoethanamine hydrochloride was dissolved in 1 ml of dichloromethane. 75.9 mg (0.750 mmol) of triethylamine was added to the obtained solution. Then a solution of 31.9 mg (0.260 mmol) of isopropyl chloroformate in 0.5 ml of dichloromethane was slowly added to the obtained mixture. After stirring for 30 minutes, the obtained product was purified by the silica gel chromatography (hexane:ethyl acetate=93:7 to 3:1) to obtain the title compound.

Yield: 38.6 mg (0.093 mmol), 43%

MS (ESI, m/z) 417 (M+H)$^+$ $^1$H-NMR (CDCl$_3$): 1.23 (6H, d), 2.12-2.48 (4H, m), 2.92-3.11 (2H, m), 3.36-3.53 (1H, m), 3.83-4.09 (3H, m), 4.90 (1H, m), 5.59 (1H, br s), 6.92 (2H, s), 7.14-7.20 (2H, m), 7.23-7.38 (6H, m).

Example 14

Synthesis of N-{3-[4-(5H-dibenzo[a,d][7]annulen-5-ylidene)-1-piperidinyl]-3-oxopropyl}-2,2-dimethyl-1-propanamine hydrochloride 5 ml of 4 N hydrochloric acid/1,4-dioxane solution was added to 184.1 mg (0.357 mmol) of t-butyl 3-[4-(5H-dibenzo[a,d][7]annulen-5-ylidene)-1-piperidinyl]-3-oxopropyl(neopentyl)carbamate, and they were stirred for 1 hour. The solvent was evaporated under reduced pressure. 5 ml of diethyl ether was added to the residue, and then 1 ml of 4 N hydrochloric acid/ethyl acetate solution was added thereto. The precipitates thus formed were taken by the filtration, washed with diethyl ether and dried under reduced pressure to obtain the title compound.

Yield: 149 mg (0.357 mmol), 100%

MS (ESI, m/z) 415 (M+H)$^+$ $^1$H-NMR (CDCl$_3$): 1.24 (9H, s), 2.14-2.43 (4H, m), 2.52 (2H, s), 2.62-3.37 (6H, m), 3.52 (1H, m), 3.95 (1H, m), 6.92 (2H, s), 7.12-7.24 (2H, m), 7.26-7.40 (6H, m), 9.05 (1H, br s), 9.55 (1H, br s).

Example 15

Synthesis of N-((1S)-1-{[4-(5H-dibenzo[a,d]annulen-5-ylidene)-1-piperidinyl]-carbonyl}-3-methylbutyl)-1-azepanecarboxyamide 100 mg (0.366 mmol) of 4-(5H-dibenzo[a,d][7]annulen-5-ylidene)-1-piperidine, 124 mg (0.439 mmol) of N-t-azepanecarboxyamido-(L)-leucine, 105 g (0.549 mmol) of 1-ethyl-3-(3'-dimethylaminopropyl)carbodiimide hydrochloride and 5 mg (0.04 mmol) of 4-dimethylaminopyridine were dissolved in 2 ml of dichloromethane. 74 mg (0.73 mmol) of triethylamine was added to the obtained solution, and they were stirred overnight. Saturated aqueous sodium hydrogencarbonate solution was added to the obtained mixture. After extracting with ethyl acetate 3 times, the organic layer was washed with saturated aqueous sodium chloride solution. After drying over anhydrous sodium sulfate, the solvent was evaporated under reduced pressure, and the residue was roughly purified by the silica gel chromatography (hexane:ethyl acetate=4:1 to 65:35) and then purified by the silica gel chromatography (hexane:ethyl acetate=3:1) to obtain the title compound.

Yield: 98.9 mg (0.194 mmol), 53%

MS (ESI, m/z) 512 (M+H)$^+$ $^1$H-NMR (CDCl$_3$): 0.54-1.02 (6H, m), 1.23-1.82 (11H, m), 2.10-2.25 (4H, m), 3.00 (1H, m), 3.16 (1H, m), 3.39 (4H, m), 3.65 (1H, m), 3.3 (1H, m), 4.90 (1H, m), 5.21 (1H, m), 6.92 (2H, s), 7.15-7.39 (8H, m).

Example 16

Synthesis of t-butyl 2-[4-(10,11-dihydro-5H-dibenzo[a,d][7]annulen-5-ylidene)-1-piperidinyl]-2-oxoethyl carbamate 400 mg of palladium carbon (10% w/v) was added to 400 mg (0.930 mmol) of t-butyl 2-[4-(5H-dibenzo[a,d][7]annulen-5-ylidene)-1-piperidinyl]-2-oxoethylcarbamate in 5 ml of ethanol, and they were stirred at 3.9 MPa in hydrogen gas atmosphere overnight. After the filtration, the solvent was evaporated under reduced pressure to obtain the title compound.

Yield: 397 g (0.918 mmol), 99%

MS (ESI, m/z) 433 (M+H)$^+$ $^1$H-NMR (CDCl$_3$): 1.46 (9H, s), 2.29-2.50 (4H, m), 2.77-2.92 (2H, m), 3.08-3.21 (2H, m), 3.31-3.45 (2H, m), 3.45-3.56 (1H, m), 3.87-4.10 (3H, m), 5.56 (1H, br s), 7.00-7.07 (2H, m), 7.09-7.20 (6H, m).

Example 17

Synthesis of t-butyl 2-oxo-2-[4-(9H-thioxanthen-9-ylidene)-1-piperidinyl]ethylcarbamate 500 mg (1.79 mmol) of 4-(9H-thioxanthen-9-ylidene)-1-piperidine and 515 mg (2.69 mmol) of 1-ethyl-3-(3'-dimethylaminopropyl)carbodiimide hydrochloride were suspended in 5 ml of dichloromethane. 415 mg (2.15 mmol) of N-t-butoxycarbonylglycine, 362 mg (3.58 mmol) of triethylamine and 22 mg (0.18 mmol) of 4-dimethylaminopyridine were added to the obtained suspension, and they were stirred overnight. Saturated aqueous sodium hydrogencarbonate solution was added to the obtained mixture. After extracting with ethyl acetate twice and drying over anhydrous sodium sulfate, the solvent was evaporated under reduced pressure, and the residue was roughly purified by the silica gel chromatography (dichloromethane:methanol=98:2) and then purified by the thin-layer silica gel chromatography (dichloromethane:methanol=15:1) to obtain the title compound.

Yield: 43.1 mg (0.100 mmol), 5.6%

MS (ESI, m/z) 437 (M+H)$^+$ $^1$H-NMR (CDCl$_3$): 1.45 (9H, s), 2.50-2.64 (2H, m), 2.68-2.81 (2H, m), 2.92-3.14 (2H, m), 3.52-3.62 (1H, m), 3.85-4.10 (2H, m), 4.13-4.24 (1H, m), 5.53 (1H, br s), 7.16-7.32 (6H, m), 7.48-7.54 (2H, d).

Example 18

Synthesis of Ethyl 2-[4-(10,11-dihydro-5H-dibenzo[a,d][7]annulen-5-ylidene)-1-piperidinyl]-2-oxoethyl carbamate 100 mg of palladium carbon (10% w/v) was added to 105 mg (0.261 mmol) of ethyl 2-[4-(5H-dibenzo[a,d][7]annulen-5-ylidene)-1-piperidinyl]-2-oxoethylcarbamate in 3 ml of ethanol, and they were stirred at 3.6 MPa in hydrogen gas atmosphere overnight. After the filtration, the solvent was evaporated under reduced pressure to obtain the title compound.

Yield: 101.8 mg (0.252 mmol), 97%
MS (ESI, m/z) 405 (M+H)$^+$
$^1$H-NMR (CDCl$_3$): 1.26 (3H, t), 2.30-2.52 (4H, m), 2.75-2.92 (2H, m), 3.08-3.23 (2H, m), 3.30-3.45 (2H, m), 3.45-3.58 (1H, m), 3.90-4.20 (5 h, m), 5.68 (1H, br s), 6.98-7.07 (2H, m), 7.07-7.21 (6H, m).

Example 19

Synthesis of ethyl 2-oxo-2-[4-(9H-thioxanthen-9-ylidene)-1-piperidinyl]ethylcarbamate Step 1

Synthesis of 2-[4-(9H-thioxanthen-9-ylidene)-1-piperidinyl]-2-oxoethanamine hydrochloride 135 mg (0.297 mmol) of t-butyl 2-oxo-2-[4-(9H-thioxanthen-9-ylidene)-1-piperidinyl]ethylcarbamate was dissolved in 2 ml of dioxane. After adding 2 ml of 4 N hydrochloric acid/1,4-dioxane solution, they were stirred overnight. The obtained mixture was neutralized with saturated aqueous sodium hydrogencarbonate solution. After extracting with ethyl acetate twice and drying over anhydrous sodium sulfate, the solvent was evaporated under reduced pressure. 2 ml of dichloromethane and then 2 ml of 4 N hydrochloric acid/1,4-dioxane solution were added to the residue. The resultant precipitates were taken by the filtration, washed with dichloromethane and air-dried. After further drying under reduced pressure, the title compound was obtained.

Yield: 72.4 mg (0.195 mmol), 66%
$^1$H-NMR (DMSO-d$_6$): 2.40-2.54 (2H, m), 2.57-2.80 (2H, m), 3.20 (2H, m), 3.34-3.75 (1H, m), 3.80-3.96 (3H, m), 7.22-7.48 (6H, m), 7.57 (2H, d), 8.16 (3H, br s).

Step 2

Synthesis of ethyl 2-oxo-2-[4-(9H-thioxanthen-9-ylidene)-1-piperidinyl]ethylcarbamate 50 mg (0.134 mmol) of 2-[4-(9H-thioxanthen-9-ylidene)-1-piperidinyl]-2-oxoethanamine hydrochloride was dissolved in dichloroethane. 41 mg (0.405 mmol) of triethylamine was added to the obtained solution. A solution of 17.5 mg (0.161 mmol) of ethyl chloroformate in 0.5 ml of dichloromethane was added to the resultant mixture. After stirring for 15 minutes, the product was purified by the thin-layer silica gel chromatography (hexane:ethyl acetate=85:100) to obtain the title compound.

Yield: 36.7 mg (0.0897 mmol), 67%
MS (ESI, m/z) 409 (M+H)$^+$
$^1$H-NMR (CDCl$_3$): 1.26 (3H, t), 2.48-2.64 (2H, m), 2.68-2.82 (2H, m), 2.92-3.16 (2H, m), 3.51-3.64 (1H, m), 3.90-4.24 (5h, m), 5.67 (1H, br s), 7.22-7.33 (6H, m), 7.51 (2H, d).

Example 20

Synthesis of t-butyl 3-[4-(5H-dibenzo[a,d][7]annulen-5-ylidene)-1-piperidinyl]-3-oxopropylcarbamate 50 mg (0.183 mmol) of 4-(5H-dibenzo[a,d][7]annulen-5-ylidene) 1-piperidine was dissolved in 1 ml of dichloromethane. 41.5 mg (0.219 mmol) of N-t-butoxycarbonyl-3-aminopropionic acid, 2 mg (0.018 mmol) of 4-dimethylaminopyridine, 37 mg (0.366 mmol) of triethylamine and 52.6 mg (0.274 mmol) of 1-ethyl-3-(3'-dimethylaminopropyl)carbodiimide hydrochloride were added to the obtained solution, and they were stirred overnight. After the purification by the thin-layer silica gel chromatography (hexane:ethyl acetate=2:3), the title compound was obtained.

Yield: 72.3 mg (0.163 mmol), 89%
MS (ESI, m/z) 445 (M+H)$^+$
$^1$H-NMR (CDCl$_3$): 1, 49 (3H, s), 2.12-2.36 (4H, m), 3.86-3.36 (4H, m), 3.52-3.28 (1H, m), 3.85-4.08 (1H, m), 4.40-4.58 (1H, d), 4.69-4.83 (1H, d), 5.16 (1H, br s), 6.92 (2H, s), 7.13-7.22 (2H, m), 7.22-7.39 (6H, m).

Example 21

Synthesis of t-butyl (4S)-4-{[4-(5H-dibenzo[a,d][7]annulen-5-ylidene)-1-piperidinyl]carbonyl}-1,3-thiazolidine-3-carboxylate The reaction and the purification were conducted in the same manner as that of Example 20 except that N-t-butoxycarbonyl-3-aminopropionic acid was replaced with 3-(t-butoxycarbonyl)-1,3-thiazolidine-4-carboxyllc acid.

Yield: 70.8 mg (0.145 mmol), 79%
MS (ESI, m/z) 489 (M+H)$^+$
$^1$H-NMR (CDCl$_3$): 1.29-1.52 (9H, m), 2.10-2.50 (4H, m), 2.70-3.45 (4H, m), 3.51-3.76 (1H, m), 3.82-4.07 (1H, m), 4.47 (1H, d), 4.75 (1H, d), 4.82-5.23 (1H, m), 6.92 (2H, s), 7.17 (2H, d), 7.20-7.40 (6H, m).

Example 22

Synthesis of t-butyl (2R)-2-{[4-(5H-dibenzo[a,d][7]annulen-5-ylidene)-1-piperidinyl]carbonyl}-1-pyrrolidinecarboxylate 100 mg (0.366 mmol) of 4-(5H-dibenzo[a,d][7]annulen-5-ylidene)-1-piperidine, 94.0 mg (0.439 mmol) of N-t-butoxycarbonyl-(L)-proline, 4 mg (0.036 mmol) of 4-dimethylaminopyridine and 105.2 mg (0.548 mmol) of 1-ethyl-3-(3'-dimethylaminopropyl)carbodiimide hydrochloride were dissolved in 1 ml of dichloromethane. 74 mg (0.731 mmol) of triethylamine was added to the obtained solution, and they were stirred for 3 hours. After the purification by the silica gel chromatography (hexane:ethyl acetate=1:1), the title compound was obtained.

Yield: 155.8 mg (0.331 mmol), 91%
MS (ESI, m/z) 471 (M+H)$^+$
$^1$H-NMR (CDCl$_3$): 1.26-1.52 (9H, m), 1.60-2.53 (8H, m), 2.80-3.26 (2H, m), 3.28-3.71 (3H, m), 3.77-4.10 (1H, m), 4.46-4.72 (1H, m), 6.92 (2H, s), 7.11-7.40 (8H, m).

Example 23

Synthesis of t-butyl 2-[3-(10,11-dihydro-5H-dibenzo[a,d][7]annulen-5-ylidene)-1-pyrrolidinyl]-2-oxoethylcarbamate 94.0 mg (0.36 mmol) of 3-(10,11-dihydro-5H-dibenzo[a,d][7]-annulen-5-ylidene)-1-pyrrolidine, 83.7 ml (0.44 mmol)

of N-t-butoxycarbonylglycine, 103.8 mg (0.54 mmol) of 1-ethyl-3-(3'-dimethylaminopropyl)carbodiimide hydrochloride and 4.4 mg (0.04 mmol) of 4-dimethylaminopyridine were dissolved in 1 ml of dichloromethane. 72.8 mg (0.72 mmol) of triethylamine was added to the obtained solution. They were stirred overnight and then purified by the silica gel chromatography (hexane:ethyl acetate=88:12 to 5:1) to obtain the title compound.

Yield: 97.9 g (0.217 mmol), 72%
MS (ESI, m/z) 419 (M+H)$^+$
$^1$H-NMR (CDCl$_3$): 1.43 (9H, s), 2.48-2.67 (1H, m), 2.70-3.00 (3H, m), 3.20-3.39 (3H, m), 3.58-4.00 (4H, m), 4.30 (1H, t), 5.45 (1H, br s), 7.00-7.24 (8H, m).

Example 24

Synthesis of t-butyl 2-(4-dibenzo[b,e]thiepin-11 (6H)-ylidene-1-piperidinyl)-2-oxoethylcarbamate 88.0 mg (0.30 mmol) of 4-dibenzo[b,e]thiepin-11(6H)-ylidene-1-piperidine, 69.6 mg (0.36 mmol) of N-t-butoxycarbonylglycine, 86.3 g (0.45 mmol) of 1-ethyl-3-(3'-dimethylaminopropyl)carbodiimide hydrochloride and 3.7 mg (0.03 mmol) of 4-dimethylaminopyridine were dissolved in 1 ml of dichloromethane. 60.7 mg (0.60 mmol) of triethylamine was added to the obtained solution. They were stirred overnight and then purified by the silica gel chromatography (hexane:ethyl acetate=88:12 to 5:1) to obtain the title compound.

Yield: 115.8 g (0.257 mmol), 86%
MS (ESI, m/z) 451 (M+H)$^+$
$^1$H-NMR (CDCl$_3$): 1.45 (9H, s), 2.09-2.20 (2H, m), 2.38-2.61 (2H, m), 3.10-3.52 (4H, m), 3.34-4.08 (3H, m), 4.86 (1H, d), 5.52 (1H, br s), 6.96-7.16 (5h, m), 7.20-7.35 (3H, m).

Example 25

Synthesis of 2-[4-(5H-dibenzo[a,d][7]annulen-5-ylidene)-1-piperidinyl]-2-oxoethylformamide 150 mg (0.406 mmol) of 2-[4-(5H-dibenzo[a,d][7]annulen-5-ylidene)-1-piperidinyl]-2-oxoethanamine hydrochloride, 80.5 mg (0.406 mmol) of 2,2-dimethyl-1-iodopropane and 84.3 mg (0.610 mmol) of potassium carbonate were dissolved in 1 ml of N,N-dimethylformamide, and the obtained solution was stirred at 120° C. overnight. The product was purified by the silica gel chromatography (hexane:ethyl acetate=9:1 to 2:3) to obtain the title compound.

Yield: 18.8 mg (0.052 mmol), 13%
MS (ESI, m/z) 359 (M+H)$^+$
$^1$H-NMR (CDCl$_3$): 2.14-2.38 (4H, m), 2.96-3.12 (2H, m), 3.40-3.52 (1H, m), 3.88-4.18 (3H, m), 6.76 (1H, br s), 6.93 (2H, s), 7.10-7.42 (8H, m), 8.25 (1H, s).

Example 26

Synthesis of t-butyl 2-[4-(5H-dibenzo[a,d][7]annulen-5-ylidene)-1-piperidinyl]-2-oxoethyl(isobutyl)carbamate Step 1

Synthesis of N-(t-butoxycarbonyl)-N-isobutylglycine 366 mg (5.01 mmol) of isobutylamine and 1.52 g (15.0 mmol) of triethylamine were dissolved in 10 ml of water. 695 mg (5.00 mmol) of bromoacetic acid was added to the obtained solution, and they were stirred for 1 hour. A solution of 1.63 g (7.50 mmol) of di(t-butyl) dicarbonate in 5 ml of 1,4-dioxane was added to the resultant mixture, and they were stirred for additional 1 hour. 10 ml of 1 N aqueous sodium hydroxide solution was added to the reaction mixture. After extracting with dichloromethane twice, 11 ml of 1 N aqueous hydrochloric acid solution was added to the aqueous layer. After extracting with dichloromethane 3 times, the obtained organic layer was dried over anhydrous sodium sulfate and then the solvent was evaporated under reduced pressure to obtain the title compound.

Yield: 829.1 mg (3.58 mmol), 72%
$^1$H-NMR (CDCl$_3$): 0.89 (6H, d), 1.45 (9H, d), 1.83 (1H, m), 3.09 (2H, t), 3.93 (2H, d).

Step 2:

Synthesis of t-butyl 2-[4-(5H-dibenzo[a,d][7]annulen-5-ylidene)-1-piperidinyl]-2-oxoethyl(isobutyl)carbamate 178 mg (0.768 mmol) of N-(t-butoxycarbonyl)-N-isobutylglycine, 150 mg (0.549 mmol) of 4-(5H-dibenzo[a,d]annulen-5-ylidene)-1-piperidine, 210 mg (1.10 mmol) of 1-ethyl-3-(3'-dimethylaminopropyl)carbodiimide hydrochloride and 6 mg (0.05 mmol) of 4-dimethylaminopyridine were dissolved in 2 ml of dichloromethane. 139 mg (1.37 mmol) of triethylamine was added to the resultant solution and they were stirred for 1 hour. After the purification by the silica gel chromatography (hexane:ethyl acetate 95:5 to 4:1), the title compound was obtained.

Yield: 222.1 mg (0.456 mmol) (83%)
MS (ESI, m/z) 487 (M+H)$^+$
$^1$H-NMR (CDCl$_3$): 0.87 (6H, d), 1.44 (9H, d), 1.85 (1H, m), 2.10-2.48 (4H, m), 3.42-3.40 (4H, m), 3.49 (1H, br s), 3.72-4.34 (3H, m), 6.92 (2H, s), 7.12-7.38 (8H, m).

Example 27

Synthesis of t-butyl 2-[4-(5H-dibenzo[a,d][7]annulen-5-ylidene)-1-piperidinyl]-2-oxoethyl(methyl)carbamate 83.1 mg (0.439 mmol) of N-(t-butoxycarbonyl)-N-methylglycine, 100 mg (0.366 mmol) of 4-(5H-dibeno[a,d]annulen-5-ylidene)-1-piperidine, 105 mg (0.549 mmol) of 1-ethyl-3-(3'-dimethylaminopropyl)carbodiimide hydrochloride and 5 mg (0.04 mmol) of 4-dimethylaminopyridine were dissolved in 1.5 ml of dichloromethane. 74.0 mg (0.732 mmol) of triethylamine was added to the resultant solution and they were stirred for 1 hour. After the purification by the silica gel chromatography (hexane:ethyl acetate=89:11 to 65:35), the title compound was obtained.

Yield: 102 mg (0.229 mmol) (63%)
MS (ESI, m/z) 445 (M+H)$^+$
$^1$H-NMR (CDCl$_3$): 1.45 (9H, d), 2.12-2.37 (4H, m), 2.91 (3H, s), 2.95-3.12 (2H, m), 3.49 (1H, br s), 3.82-4.18 (3H, m), 6.93 (2H, s), 7.14-7.36 (8H, m).

Example 28

Synthesis of N-(t-butyl)-N'-{2-[4-(5H-dibenzo[a,d][7]annulen-5-ylidene)-1-piperidinyl]-2-oxoethyl}urea 89.2 mg (0.55 mmol) of 1,1'-carbonylbis-1H-imidazole and 25.3 mg (0.25 mmol) of triethylamine were dissolved in 2.5 ml of tetrahydrofuran.

A solution of 36.6 mg (0.50 mmol) of t-butylamine in 1 ml of tetrahydrofuran was slowly added to the resultant solution at 0° C. in argon stream. After stirring for 1 hour, a solution of 110.7 mg (0.30 mmol) of 2-[4-(5H-dibenzo[a,d][7]annulen-5-ylidene)-1-piperidinyl]-2-oxoethanamine hydrochloride and 30.3 mg (0.30 mmol) of triethylamine in 1 ml of tetrahydrofuran was slowly added thereto. After stirring for 2 hours, the solvent was evaporated and the product was purified by the silica gel chromatography (hexane:ethyl acetate=85:15 to 3:2) to obtain the title compound.

Yield: 70.7 mg (0.165 mmol), 66%

MS (ESI, m/z) 430 (M+H)$^+$ $^1$H-NMR (CDCl$_3$): 1.31 (9H, s), 2.10-2.35 (4H, m), 2.03-3.10 (2H, m), 3.40-3.52 (1H, m), 3.84-4.10 (3H, m), 4.56 (1H, br s), 5.30 (1H, s), 6.92 (2H, s), 7.14-7.24 (2H, m), 7.27-7.7.27 (6H, m).

Example 29

Synthesis of t-butyl 2-({2-[4-(5H-dibenzo[a,d][7]annulen-5-ylidene)-1-piperidinyl]-2-oxoethyl}amino)-2-oxoethylcarbamate 35.0 mg (0.095 mmol) of 2-[4-(5H-dibenzo[a,d][7]annulen-5-ylidene)-1-piperidinyl]-2-oxoethanamine hydrochloride, 19.7 mg (0.114 mmol) of N-t-butoxycarbonylglycine, 27.2 mg (0.142 mmol) of 1-ethyl-3-(3'-dimethylaminopropyl)carbodiimide hydrochloride and 1 mg (0.01 mmol) of 4-dimethylaminopyridine were dissolved in 1 ml of dichloromethane. 19.2 mg (0.190 mmol) of triethylamine was added to the obtained solution, and they were stirred for 1 hour. The product was purified by the silica gel chromatography (hexane:ethyl acetate=7:3 to 3:7) to obtain the title compound.

Yield: 31.8 mg (0.065 mmol), 69%

MS (ESI, m/z) 488 (M+H)$^+$ $^1$H-NMR (CDCl$_3$): 1.45 (9H, s), 2.12-2.38 (4H, m), 2.94-3.11 (2H, m), 3.38-3.52 (2H, m), 3.85 (2H, d), 3.91-4.10 (3H, m), 5.06 (1H, br s), 6.92 (2H, s), 7.00 (1H, br s), 7.13-7.22 (2H, m), 7.22-7.39 (6H, m).

Example 30

Synthesis of t-butyl 3-({2-[4-(5H-dibenzo[a,d][7]annulen-5-ylidene)-1-piperidinyl]-2-oxoethyl}amino)-3-oxopropylcarbamate 35.0 mg (0.095 mmol) of 2-[4-(5H-dibenzo[a,d][7]annulen-5-ylidene)-1-piperidinyl]-2-oxoethanamine hydrochloride, 21.5 mg (0.114 mmol) of N-t-butoxycarbonylalanine, 27.2 mg (0.142 mmol) of 1-ethyl-3-(3'-dimethylaminopropyl)carbodiimide hydrochloride and 1 mg (0.01 mmol) of 4-dimethylaminopyridine were dissolved in 1 ml of dichloromethane. 19.2 mg (0.190 mmol) of triethylamine was added to the obtained solution, and they were stirred for 1 hour. The product was purified by the silica gel chromatography (hexane:ethyl acetate=7:3 to 3:7) to obtain the title compound.

Yield: 32.5 mg (0.065 mmol), 68%

MS (ESI, m/z) 502 (M+H)$^+$ $^1$H-NMR (CDCl$_3$): 1.42 (9H, s), 2.12-2.38 (4H, m), 2.45 (2H, t), 3.04 (2H, m), 3.32-3.51 (3H, m), 3.87-4.10 (3H, m), 5.14 (1H, br s), 6.59 (1H, br s), 6.92 (2H, s), 7.13-7.40 (8H, m).

Example 31

Synthesis of t-butyl 3-[4-(5H-dibenzo[a,d][7]annulen-5-ylidene)-1-piperidinyl]-3-oxopropyl(neopentyl)carbamate 872 mg (10.0 mmol) of 2,2-dimethylpropylamine was dissolved in 10 ml of ethanol. 34.0 mg (0.50 mmol) of sodium ethoxide and 1.00 g (10.0 mmol) of ethylacrylic acid were added to the obtained solution, and they were stirred overnight. 1 ml of water was added to the reaction mixture and the organic solvent was evaporated under reduced pressure. 2.62 g (12.0 mmol) of di(t-butyl) dicarbonate and 25 ml of 1 N aqueous sodium hydroxide solution were added to the residue, and they were stirred for 3.5 hours. After extracting with dichloromethane twice, the aqueous layer was neutralized with 1 N aqueous hydrochloric acid solution. After extracting with dichloromethane 3 times, the extract was dried over anhydrous sodium sulfate and then the solvent was evaporated under reduced pressure. The obtained product was dissolved in 2 ml of dichloromethane. 145 mg (0.531 mmol) of 4-(5H-dibenzo[a,d][7]annulen-5-ylidene)-1-piperidine, 122 mg (0.637 mmol) of 1-ethyl-3-(3'-dimethylaminopropyl)carbodiimide hydrochloride and 6 mg (0.05 mmol) of 4-dimethylaminopyridine were added to the obtained solution. 107.5 mg (1.06 mmol) of triethylamine was further added to the reaction mixture, and they were stirred for 2 hour. The product was purified by the silica gel chromatography (hexane:ethyl acetate=89:11 to 4:1) to obtain the title compound.

Yield: 233 mg (0.452 mmol), 85%

MS (ESI, m/z) 515 (M+H)$^+$ $^1$H-NMR (CDCl$_3$): 0.91 (9H, s), 1.43 (9H, s), 2.10-2.40 (4H, m), 2.48-2.71 (2H, m), 2.94-3.21 (4H, m), 3.49 (2H, t), 3.62 (1H, m), 3.85-3.98 (1H, m), 6.92 (2H, s), 7.14-7.23 (2H, m), 7.23-7.38 (6H, m).

Example 32

Synthesis of t-butyl 2-[4-(10,11-dihydro-5H-dibenzo[b,f]azepin-5-yl)-1-pipperidinyl]-2-oxoethylcarbamate 60.0 mg (0.216 mmol) of 5-(4-piperidinyl)-10,11-dihydro-5H-dibenzo-[b,f]azepine, 50.0 mg (0.258 mmol) of N-t-butoxycarbonylglycine, 62.1 mg (0.324 mmol) of 1-ethyl-3-(3'-dimethylaminopropyl)carbodiimide hydrochloride and 3 mg (0.03 mmol) of 4-dimethylaminopyridine were dissolved in 1 ml of dichloromethane. 43.7 mg (0.432 mmol) of triethylamine was added to the obtained solution, and they were stirred for 1 hour. The product was purified by the silica gel chromatography (hexane:ethyl acetate=89:11 to 65:35) to obtain the title compound.

Yield: 81.1 mg (0.186 mmol), 86%

MS (ESI, m/z) 436 (M+H)$^+$ $^1$H-NMR (CDCl$_3$): 1.43 (9H, s), 1.60-1.77 (2H, m), 1.98-2.10 (2H, m), 2.77 (2H, br s), 3.15 (1H, m), 3.28 (1H, m), 3.38-3.60 (3H, m), 3.80-4.02 (3H, m), 4.20 (1H, m), 5.50 (1H, br s), 6.93-7.00 (2H, m), 7.05-7.15 (6H, m).

Example 33

Synthesis of t-butyl (1S)-1-{[4-(5H-dibenzo[a,d][7]annulen-5-ylidene)-1-piperidinyl]carbonyl}-3-methylbutyl(methyl)carbamate 389 mg (1.59 mmol) of t-butoxycarbonyl-N-methyl-L-leucine, 311 mg (1.62 mmol) of 1-ethyl-3-(3'-dimethylaminopropyl)carbodiimide hydrochloride, 416 mg (1.52 mmol) of 4-(5H-dibenzo[a,d][7]annulen-5-ylidene)-1-piperidine and 0.22 ml (1.59 mmol) of triethylamine were stirred at room temperature overnight. Saturated aqueous sodium hydrogencarbonate solution was added to the reaction mixture. After extracting with dichloromethane, the organic layer was dried over anhydrous sodium sulfate and then concentrated under reduced pressure. The residue was purified by the silica gel chromatography (hexane:ethyl acetate=3:1) to obtain the title compound.
Yield: 368 mg (0.74 mmol), 48%
MS (ESI, m/z) 501 (M+H)$^+$
$^1$H-NMR (CDCl$_3$): 0.86-0.98 (6H, dd), 1.34-1.65 (10H, m), 2.03-2.38 (4H, m), 2.64-2.84 (3H, m), 2.88-4.18 (6H, m), 4.78-5.12 (1H, m), 6.90-6.94 (2H, m), 7.11-7.38 (8H, m).

Example 34

Synthesis of N-((1S)-1-{[4-(5H-dibenzo[a,d][7]annulen-5-ylidene)-1-piperidinyl]carbonyl}-3-methylbutyl)-N-methylamine hydrochloride 344 mg (0.69 mmol) of t-butyl (1S)-1-{[4-(5H-dibenzo[a,d][7]annulen-5-ylidene)-1-piperidinyl]carbonyl}-3-methylbutyl(methyl)carbamate was dissolved in 2 ml of 1,4-dioxane. 4 ml of 4 N hydrochloric acid/1,4-dioxane solution was added to the obtained solution, and they were stirred at room temperature for 5 hours and then concentrated under reduced pressure to obtain the title compound.
Yield: 301 mg (0.69 mmol), 100%
MS (ESI, m/z) 401 (M+H)$^+$
$^1$H-NMR (CDCl$_3$): 0.86-1.04 (6H, m), 1.66-2.01 (5H, m), 2.16-2.56 (4H, m), 2.72 (3H, d), 2.94-3.26 (2H, m), 3.54-3.72 (1H, m), 3.94-4.08 (1H, m), 4.24-4.35 (1H, m), 6.89-6.93 (2H, m), 7.14-7.20 (2H, m), 7.22-7.38 (6H, m).

Example 35

Synthesis of t-butyl 2-[[3-(5H-dibenzo[a,d][7]annulen-5-yl)propyl](methyl)-amino]-2-oxoethylcarbamate 134 mg (0.70 mmol) of 1-ethyl-3-(3'-dimethylaminopropyl)carbodiimide hydrochloride, 176 mg (0.59 mmol) of protriptyline hydrochloride and 0.176 ml (1.26 mmol) of triethylamine were added to 129 mg (0.74 mmol) of t-butoxycarbonylglydine in 5 ml of dichloromethane, and they were stirred at room temperature overnight. Saturated aqueous sodium hydrogencarbonate solution was added to the reaction mixture. After extracting with dichloromethane, the organic layer was dried over anhydrous sodium sulfate and then concentrated under reduced pressure. The residue was purified by the silica gel chromatography (hexane:ethyl acetate=3:1) to obtain the title compound.
Yield: 228 mg (0.54 mmol), 92%
MS (ESI, m/z) 421 (M+H)$^+$
$^1$H-NMR (CDCl$_3$): 1.13-1.30 (2H, m), 1.44 (9H, s), 1.64-1.76 (2H, m), 2.73 (3H, d), 3.27-3.42 (1H, m), 4.36 (1H, s), 5.31 (1H, s), 5.98 (1H, s), 6.49 (2H, s), 7.29-7.50 (8H, m).

Example 36

Synthesis of t-butyl 2-[[3-(5H-dibenzo[a,d][7]annulen-5-ylidene)propyl]-(methyl)amino]-2-oxoethylcarbamate Step 1

Synthesis of 3-(5H-dibenzo[a,d][7]annulen-5-ylidene)-N-methyl-1-propanamine 20 ml of saturated aqueous sodium hydrogencarbonate solution was added to 2.467 g (7.91 mmol) of cyclobenzaprine hydrochloride in 20 ml of chloroform, and they were stirred at room temperature for 10 minutes. After extracting with chloroform, the organic layer was dried over anhydrous sodium sulfate and then concentrated under reduced pressure. 15 ml of toluene was added to the residue, and they were heated at 80° C. 4.0 ml (41.8 mmol) of ethyl chloroformate was added thereto, and they were stirred at 80° C. overnight. 4.0 ml (41.8 mmol) of ethyl chloroformate was added to the reaction mixture, and they were stirred under heating for 2 days. Water was added to the reaction mixture. After extracting with ethyl acetate, the organic layer was dried over anhydrous sodium sulfate and then concentrated under reduced pressure. The residue was purified by the silica gel chromatography (hexane:ethyl acetate=1:1). 11.4 ml of 1-butanol and 1.97 g (35.1 mmol) of powdery potassium hydroxide were added to the obtained product, and they were stirred under heating at 120° C. for 4 hours. The reaction mixture was poured in water at room temperature. After the extraction with chloroform, the organic layer was dried over anhydrous sodium sulfate and then concentrated under reduce pressure to obtain the title compound.
Yield: 1.725 g (6.60 mmol), 83%
MS (ESI, m/z) 262 (M+H)$^+$
$^1$H-NMR (CDCl$_3$): 2.26-2.35 (2H, m), 2.30 (3H, s), 2.53-2.66 (2H, m), 5.53 (1H, t), 6.86 (2H, d), 7.21-7.37 (8H, m).

Step 2

Synthesis of t-butyl 2-[[3-(5H-dibenzo[a,d][7]annulen-5-ylidene)propyl]-(methyl)amino]-2-oxoethylcarbamate 105 mg (0.60 mmol) of t-butoxycarbonylglycine, 111 mg (0.58 mmol) of 1-ethyl-3-(3'-dimethylaminopropyl)carbodiimide hydrochloride, 133 mg (0.51 mmol) of 3-(5H-dibenzo[a,d][7]annulen-5-ylidene)-N-methyl-1-propanamine and 0.08 ml (0.57 mmol) of triethylamine were stirred in 5 ml of dichloromethane at room temperature overnight. Saturated aqueous sodium hydrogencarbonate solution was added to the reaction mixture. After extracting with dichloromethane, the organic layer was dried over anhydrous sodium sulfate and then concentrated under reduced pressure. The residue was purified by the silica gel chromatography (hexane:ethyl acetate=2:1) to obtain the title compound.
Yield: 130 mg (0.31 mmol), 61%
MS (ESI, m/z) 419 (M+H)$^+$
$^1$H-NMR (CDCl$_3$): 1.45 (9H, d), 2.23-2.52 (2H, m), 2.68 (3H, d), 3.10-3.58 (2H, m), 3.72-3.88 (2H, m), 5.40-5.53 (2H, m), 6.84-6.88 (2H, m), 7.15-7.40 (8H, m).

Example 37

Synthesis of t-butyl (1S)-1-{[[3-(5H-dibenzo[a,d][7]annulen-5-ylidene)propyl]-(methyl)amino]carbonyl}-3-methylbutyl(methyl)carbamate 280 mg (1.14 mmol) of t-butoxycarbonyl-N-methyl-L-leucine, 204 mg (1.06 mmol) of 1-ethyl-3-(3'-dimethylaminopropyl)carbodiimide hydrochloride, 271 mg (1.04 mmol) of 3-(5H-dibenzo[a,d][7]annulen-5-ylidene)-N-methyl-1-propanamine and 0.15 ml (1.08 mmol) of triethylamine were stirred in 10 ml of dichloromethane at room temperature overnight. Saturated aqueous sodium hydrogencarbonate solution was added to the reaction mixture. After extracting with dichloromethane, the organic layer was dried over anhydrous sodium sulfate and then concentrated under reduced pressure. The residue was purified by the silica gel chromatography (hexane:ethyl acetate=82:18) to obtain the title compound.

Yield: 178 mg (0.37 mmol), 35%
MS (ESI, m/z) 489 (M+H)$^+$
$^1$H-NMR (CDCl$_3$): 0.63-0.96 (6H, m), 1.24-1.62 (11H, m), 2.22-2.91 (9H, m), 3.10-3.70 (2H, m), 4.66-5.08 (1H, m), 5.41-5.58 (1H, m), 6.79-6.91 (2H, m), 7.16-7.38 (8H, m).

Example 38

Synthesis of (2S)—N-[3-(5H-dibenzo[a,d][7]annulen-5-ylidene)propyl]-N,4-dimethyl-2-(methylamino)pentanamide hydrochloride 5 ml of dichloromethane and 2.5 ml of trifluoroacetic acid were added to 169 mg (0.35 mmol) of t-butyl (1S)-1-{[[3-(5H-dibenzo[a,d][7]annulen-5-ylidene)propyl] (methyl) amino]carbonyl}-3-methylbutyl(methyl)carbamate, and they were stirred at room temperature for 2 hours. The reaction mixture was concentrated under reduced pressure. 1 N aqueous sodium hydroxide solution was added thereto to make it basic. After extracting with ethyl acetate, the organic layer was dried over anhydrous sodium sulfate and then concentrated under reduced pressure. The residue was dissolved in 5 ml of 1,4-dioxane. 4 N hydrochloric acid/1,4-dioxane solution was added to the obtained solution. The resultant mixture was concentrated under reduced pressure to obtain the title compound.

Yield: 145 mg (0.34 mmol) 99%
MS (ESI, m/z) 389 (M+H)$^+$
$^1$H-NMR (CDCl$_3$): 0.74-0.94 (6H, m), 1.40-1.75 (2H, m), 2.06-2.83 (9H, m), 3.08-3.60 (2H, m), 3.75-4.11 (1H, m), 5.40-5.51 (1H, m), 6.77-6.92 (2H, m), 7.16-7.41 (8H, m).

Example 39

Synthesis of t-butyl 2-[[3-(10,11-dihydro-5H-dibenzo[a,d][7]annulen-5-ylidene)propyl] (methyl) amino]-2-oxoethylcarbamate 281 mg (1.47 mmol) of 1-ethyl-3-(3'-dimethylaminopropyl)carbodiimide hydrochloride, 281 mg (1.47 mmol) of nortriptyline hydrochloride and 0.40 ml (2.87 mmol) of triethylamine were added to 251 mg (1.44 mmol) of t-butoxycarbonylglycine in 10 ml of dichloromethane, and they were stirred at room temperature overnight. Saturated aqueous sodium hydrogencarbonate solution was added to the reaction mixture. After extracting with dichloromethane, the organic layer was dried over anhydrous sodium sulfate and then concentrated under reduced pressure. The residue was purified by the silica gel chromatography (hexane:ethyl acetate=4:1) to obtain the title compound.

Yield: 203 mg (0.48 mmol), 33%
MS (ESI, m/z) 421 (M+H)$^+$
$^1$H-NMR (CDCl$_3$): 1.44 (9H, s), 1.64-1.76 (2H, m), 2.30-2.48 (2H, m), 2.77 (3H, d), 2.85-3.56 (6H, m), 3.83-3.95 (2H, m), 5.43-5.75 (1H, brd), 5.79 (1H, dt), 7.00-7.28 (8H, m).

Example 40

Synthesis of t-butyl 2-[(5H-dibenzo[a,d][7]annulen-5-ylidenacetyl)amino]-ethylcarbamate Step 1

Synthesis of 5H-dibenzo[a,d][7]annulen-5-ylidenacetic acid 890 mg (22.3 mmol) of sodium hydride (60% oily) was added to 4.99 g (22.3 mmol) of ethyl diethylphosphonoacetate in 55 ml of dimethyl sulfoxide, and they were stirred at room temperature overnight. 4.58 g (22.2 mmol) of 5H-dibenzo[a,d]-5-cycloheptenone was added to the reaction mixture, and they were stirred at room temperature for 1 hour 15 minutes and then stirred under heating at 100° C. for 2 days. Dimethyl sulfoxide was evaporated under reduced pressure. 20 ml of ethanol and 20 ml of 6 N aqueous sodium hydroxide solution were added to the residue, and they were stirred under heating at 100° C. for 3 days. The reaction mixture was concentrated under reduced pressure and then acidified with 1 N hydrochloric acid. After extracting with ethyl acetate, the organic layer was dried over anhydrous sodium sulfate and then concentrated under reduced pressure. The residue was purified by the silica gel chromatography (hexane:ethyl acetate=1:1) to obtain the title compound.

Yield: 1.552 g (6.25 mmol), 28%
MS (ESI, m/z) 247 (M−H)$^-$
$^1$H-NMR (CDCl$_3$): 5.90 (1H, s), 6.94 (2H, q), 7.30-7.46 (8H, m).

Step 2

Synthesis of t-butyl 2-[(5H-dibenzo[a,d][7]annulen-5-ylidenacetyl)amino]-ethylcarbamate 173 mg (0.70 mmol) of 5H-dibenzo[a,d][7]annulen-5-ylidenacetic acid, 124 mg (0.77 mmol) of t-butyl N-(2-aminoethyl)carbamate, 143 mg (0.75 mmol) of 1-ethyl-3-(3'-dimethylaminopropyl)carbodiimide hydrochloride and 0.11 ml (0.79 mmol) of triethylamine were stirred in 5 ml of dichloromethane at room temperature overnight. The reaction mixture was washed with saturated aqueous sodium hydrogencarbonate solution and the organic layer was dried over anhydrous sodium sulfate and then concentrated under reduced pressure. The residue was purified by the silica gel chromatography (hexane:ethyl acetate=7:3) to obtain the title compound.

Yield: 185 mg (0.47 mmol), 68%
MS (ESI, m/z) 391 (M+H)$^+$
$^1$H-NMR (CDCl$_3$): 1.44 (9H, s), 2.78-3.08 (3H, m), 3.27-3.42 (1H, m), 4.36 (1H, s), 5.31 (1H, s), 5.98 (1H, s), 6.49 (2H, s), 7.29-7.50 (8H, m).

Example 41

Synthesis of t-butyl 3-[(5H-dibenzo[a,d][7]annulen-5-ylidenacetyl)amino]-propylcarbamate 173 mg (0.70 mmol) of 5H-dibenzo[a,d][7]annulen-5-ylidenacetic acid, 130 mg (0.75 mmol) of t-butyl N-(3-aminopropyl)carbamate, 149 mg (0.78 mmol) of 1-ethyl-3-(3'-dimethylaminopropyl)carbodiimide hydrochloride and 0.11 ml (0.79 mmol) of triethylamine were stirred in 5 ml of dichloromethane at room temperature overnight. The reaction mixture was washed with 0.5 N aqueous sodium hydroxide solution and the organic layer was dried over anhydrous sodium sulfate and then concentrated under reduced pressure. The residue was purified by the silica gel chromatography (hexane:ethyl acetate=7:3) to obtain the title compound.

Yield: 232 mg (0.57 mmol), 82%
MS (ESI, m/z) 403 (M−H)−
1H-NMR (CDCl3): 1.24-1.37 (2H, m), 1.42 (9H, s), 2.82 (2H, q), 2.90-3.04 (1H, m), 3.15-3.30 (1H, m), 4.77 (1H, s), 5.48 (1H, s), 5.98 (1H, s), 6.93 (2H, d), 7.29-7.50 (8H, m).

Example 42

Synthesis of t-butyl 4-(5H-dibenzo[a,d][7]annulen-5-ylidenacetyl)-1-piperazine carboxylate 172 mg (0.69 mmol) of 5H-dibenzo[a,d][7]annulen-5-ylideneacetic acid, 144 mg (0.78 mmol) of t-butyl 1-piperazinecarboxylate, 148 mg (0.77 mmol) of 1-ethyl-3-(3'-dimethylaminopropyl)carbodiimide hydrochloride and 0.11 ml (0.79 mmol) of triethylamine were stirred in 5 ml of dichloromethane at room temperature overnight. The reaction mixture was washed with 0.5 N aqueous sodium hydroxide solution and the organic layer was dried over anhydrous sodium sulfate and then concentrated under reduced pressure. The residue was purified by the silica gel chromatography (hexane:ethyl acetate=2:1) to obtain the title compound.

Yield: 273 mg (0.66 mmol), 95%
MS (ESI, m/z) 417 (M+H)+
1H-NMR (CDCl3): 1.42 (9H, s), 2.01-2.12 (1H, m), 2.71-2.84 (1H, m), 2.96-3.10 (2H, m), 3.11-3.26 (2H, m), 3.35-3.49 (1H, m), 3.55-3.69 (1H, m), 5.94 (1H, s), 6.83-6.96 (2H, m), 7.28-7.57 (8H, m).

Example 43

Synthesis of 1-ethyl-1-methylpropyl 2-[4-[(5H-dibenzo[a,d][7]annulen-5-ylidene)-1-piperidinyl]-2-oxoethylcarbamate Step 1

Synthesis of ethyl {[(1-ethyl-1-methylpropoxy)carbonyl]amino}acetate 0.500 ml (4.01 mmol) of ethyl isocyanatoacetate was dissolved in dichloromethane. 0.05 ml of 4 N hydrochloric acid/1,4-dioxane solution was added to the obtained solution, and they were stirred at room temperature for 5 minutes. 0.547 ml (4.41 mmol) of 3-methyl-3-pentanol was added to the reaction mixture, and they were stirred overnight. After the concentration under reduced pressure, ethyl acetate was added to the reaction mixture, and they were washed with saturated aqueous sodium hydrogencarbonate solution, dried over anhydrous sodium sulfate and then concentrated under reduced pressure. The residue was washed with diethyl ether. The filtrate was concentrated under reduced pressure to obtain the title compound.

Yield: 622 mg (2.69 mmol), 67%
1H-NMR (CDCl3): 0.85 (6H, t), 1.26 (3H, t), 1.35 (3H, s), 1.66-1.91 (4H, m), 3.87 (2H, d), 4.19 (2H, q), 5.04 (1H, br s).
Step 2

Synthesis of {[(1-ethyl-1-methylpropoxy)carbonyl]amino}acetic acid 300 mg (1.30 mmol) of ethyl {[(1-ethyl-1-methylpropoxy)carbonyl]-amino}acetate was dissolved in 2.5 ml of a solvent mixture of methanol:water (2.3:1). 1.56 ml of 1 N aqueous lithium hydroxide solution was added to the obtained solution. After stirring at room temperature for 2 hours, "DOWEX" (50W-X2 100 to 200 mesh H form) (an exchange resin of The Dow Chemical Company) was added to the reaction mixture under gentle stirring until pH of the mixture had become 5. The resin was obtained by the filtration under suction and then the filtrate was concentrated under reduced pressure and then dried to obtain the title compound.

Yield: 284 mg (1.40 mmol), 100%
MS (ESI, m/z) 202 (M−H)−
1H-NMR (CDCl3): 0.82 (6H, br t), 1.33 (3H, s), 1.67-1.84 (4H, m), 3.69 (2H, br s), 5.86 (1H, br s).
Step 3

Synthesis of 1-ethyl-1-methylpropyl 2-[4-(5H-dibenzo[a,d][7]annulen-5-ylidene)-1-piperidinyl]-2-oxoethylcarbamate 284 mg (1.40 mmol) of {[(1-ethyl-1-methylpropoxy)carbonyl]-amino}-acetic acid, 320 mg (1.17 mmol) of 4-(5H-dibenzo[a,d][7]annulen-5-ylidene)-piperidine and 322 mg (1.68 mmol) of 1-ethyl-3-(3'-dimethylaminopropyl)carbodiimide hydrochloride were dissolved in a mixed solvent of 15 ml of dichloromethane and 5 ml of dimethylformamide. 0.23 ml (1.68 mmol) of triethylamine and 14.7 mg (0.12 mmol) of dimethylaminopyridine were added to the obtained solution, and they were stirred at room temperature overnight. After the concentration under reduced pressure, ethyl acetate was added to the reaction mixture. The resultant mixture was washed with saturated aqueous sodium chloride solution. The organic layer was dried over anhydrous magnesium sulfate and then concentrated under reduced pressure. The obtained residue was purified by the silica gel chromatography (hexane:dichloromethane=95:5 to 2:3) to obtain the title compound.

Yield: 204 mg (0.445 mmol) (38%)
MS (ESI, m/z) 459 (M+H)+
1H-NMR (CDCl3): 0.85 (6H, t), 1.35 (3H, s), 1.66-1.91 (4H, m), 2.14-2.33 (4H, m), 2.97-3.06 (2H, m), 3.39-3.46 (1H, m), 3.84-4.00 (3H, m), 5.54 (1H, br s), 6.92 (2H, s), 7.15-7.18 (2H, m), 7.23-7.28 (2H, m), 7.31-7.37 (4H, m).

Example 44

Synthesis of N-(t-butyl)-4-[4-(10,11-dihydro-5H-dibenzo[b,f]azepin-5-yl)-1-piperidinyl]-4-oxobutanamide Step 1

Synthesis of 4-(t-butylamino)-4-oxobutanoic acid 3.07 g (30.6 mmol) of succinic anhydride was suspended in 30 ml of dichloromethane. 4.1 ml (34.5 mmol) of t-butylamine was dropped into the suspension, and the resultant mixture was stirred at room temperature for 1 hour. White crystals thus formed were washed with ethyl acetate and then dissolved in 40 ml of 1 N aqueous sodium hydroxide solution. The resultant solution was stirred at room temperature for 2 hours and then acidified with 1 N aqueous hydrochloric acid solution under cooling with ice. After extracting with ethyl acetate, the organic layer was dried over anhydrous sodium sulfate and then concentrated under reduced pressure to obtain the title compound.

Yield: 2.75 g (15.9 mmol), 52%
MS (ESI, m/z) 172 (M−H)−
1H-NMR (DMSO-d6): 1.20 (9H, s), 2.21-2.26 (2H, m), 2.32-2.37 (2H, m), 7.39 (1H, br s).

Step 2

Synthesis of N-(t-butyl)-4-[4-(10,11-dihydro-5H-dibenzo[b,f]azepin-5-yl)-1-piperidinyl]-4-oxobutanamide 83.2 mg (0.299 mmol) of 5-(4-piperidinyl)-10,11-dihydro-5H-dibenzo[b,f]azepine, 62.2 mg (0.359 mmol) of 4-(t-butylamino)-4-oxobutanoic acid and 82.6 mg (0.431 mmol) of 1-ethyl-3-(3'-dimethylaminopropyl)carbodiimide hydrochloride were dissolved in 5 ml of dichloromethane. 0.06 ml (0.431 mmol) of triethylamine and 3.67 mg (0.03 mmol) of 4-dimethylaminopyridine were added to the obtained solution, and they were stirred at room temperature overnight. The reaction mixture was concentrated under reduced pressure. Ethyl acetate was added thereto. After washing with 1 N aqueous hydrochloric acid solution, the organic layer was dried over anhydrous magnesium sulfate and then concentrated under reduced pressure. The residue was purified by the silica gel chromatography (dichloromethane:methanol=9:1) to obtain the title compound.

Yield: 102 mg (0.236 mmol), 79%
MS (ESI, m/z) 434 (M+H)$^+$
$^1$H-NMR (CDCl$_3$): 1.31 (9H, s), 1.58-1.70 (2H, m), 1.96-2.11 (2H, m), 2.37-2.42 (2H, m), 2.50-2.82 (4H, m), 3.14-3.26 (2H, m), 3.49 (2H, br s), 3.62-3.69 (1H, m), 3.92-4.00 (1H, m), 4.14-4.21 (1H, m), 5.78 (1H, br s), 6.92-6.99 (2H, m), 7.08-7.10 (6H, m).

Example 45

Synthesis of N-{2-[4-(5H-dibenzo[a,d][7]annulen-5-ylidene)-1-piperidinyl]-2-oxoethyl}-N,N-dimethylurea 200 mg (0.545 mmol) of 2-[4-(5H-dibenzo[a,d][7]annulen-5-ylidene)-1-piperidinyl]-2-oxoethanamine hydrochloride was suspended in 2 ml of dichloromethane. 0.19 ml of triethylamine was added to the obtained suspension. A solution of 70.3 mg (0.654 mmol) of N,N-dimethylcarbamoyl chloride in 3 ml of dichloromethane was added dropwise to the resultant mixture under cooling with ice, and they were stirred at room temperature for 30 minutes. Dichloromethane was concentrated under reduced pressure. Ethyl acetate was added to the residue. The resultant mixture was washed with saturated aqueous sodium hydrogencarbonate solution. White crystals precipitated in the organic layer was taken by the filtration to obtain the title compound.

Yield: 158 mg (0.394 mmol), 72%
MS (ESI, m/z) 430 (M+H)$^+$
$^1$H-NMR (CDCl$_3$): 2.20-2.33 (4H, m), 2.93 (6H, s), 3.01-3.10 (2H, m), 3.44-3.54 (1H, m), 3.92-4.05 (3H, m), 5.51 (1H, br s), 6.92 (2H, s), 7.15-7.19 (2H, m), 7.23-7.28 (2H, m), 7.32-7.36 (4H, m).

Example 46

Synthesis of N-{2-[4-(5H-dibenzo[a,d][7]annulen-5-ylidene)-1-piperidinyl]-2-oxoethyl}-1-piperidinecarboxamide 200 mg (0.545 mmol) of 2-[4-(5H-dibenzo[a,d][7]annulen-5-ylidene)-1-piperidinyl]-2-oxoethanamine hydrochloride was suspended in 2 ml of dichloromethane. 0.19 ml of triethylamine was added to the obtained suspension. A solution of 96.5 mg (0.654 mmol) of 1-piperidinecarbonyl chloride in 3 ml of dichloromethane was added dropwise to the resultant mixture under cooling with ice, and they were stirred at room temperature for 30 minutes. Dichloromethane was concentrated under reduced pressure. Ethyl acetate was added to the residue. The resultant mixture was washed with saturated aqueous sodium hydrogencarbonate solution. The organic layer was dried over anhydrous magnesium sulfate and then concentrated under reduced pressure. The residue was purified by the basic silica gel chromatography (hexane:ethyl acetate=4:1 to 1:4) to obtain the title compound.

Yield: 201 mg (0.455 mmol), 84%
MS (ESI, m/z) 442 (M+H)$^+$
$^1$H-NMR (CDCl$_3$): 1.49-1.62 (6H, m), 2.15-2.33 (4H, m), 3.02-3.08 (2H, m), 3.34-3.37 (4H, m), 3.45-3.51 (1H, m), 3.90-4.11 (3H, m), 5.58 (1H, br s), 6.92 (2H, s), 7.16-7.18 (2H, m), 7.28-7.35 (6H, m).

Example 47

Synthesis of N-[2-(t-butylamino)-2-oxoethyl]-4-(5H-dibenzo[a,d][7]annulen-5-ylidene)-1-piperidinecarboxamide Step 1

Synthesis of t-butyl ({[4-(5H-dibenzo[a,d][7]annulen-5-ylidene)-1-piperidinyl]-carbonyl}amino)acetate 475 mg (2.93 mmol) of N,N'-carbonyldiimidazole was dissolved in 10 ml of anhydrous tetrahydrofuran. 0.45 ml (3.29 mmol) of triethylamine was added to the obtained solution, and they were stirred at room temperature for 10 minutes. The reaction mixture was cooled with ice, and 460 mg (2.74 mmol) of t-butyl aminoacetate hydrochloride was added dropwise to the mixture during a period of about 10 minutes, and they were stirred at room temperature for 1 hour. After cooling with ice, 500 mg (1.83 mmol) of 4-(5H-dibenzo[a,d][7]annulen-5-ylidene)piperidine was added to the resultant mixture, and they were stirred at room temperature overnight. Water was added to the reaction mixture. After extracting with ethyl acetate followed by drying over anhydrous magnesium sulfate, the product was concentrated under reduced pressure. The residue thus obtained was purified by the silica gel chromatography (dichloromethane:methanol=95:5 to 2:3) to obtain the title compound.

Yield: 752 mg (1.75 mmol), 95%
MS (ESI, m/z) 431 (M+H)$^+$
$^1$H-NMR (CDCl$_3$): 1.46 (9H, s), 2.12-2.20 (2H, m), 2.28-2.33 (2H, m), 3.01-3.09 (2H, m), 3.52-3.59 (2H, m), 3.90 (2H, d), 4.91 (1H, br t).

Step 2

Synthesis of ({[4-(5H-dibenzo[a,d][7]annulen-5-ylidene)-1-piperidinyl]-carbonyl}amino)acetic acid 752 mg (1.75 mmol) of t-butyl({[4-(5H-dibenzo[a,d][7]annulen-5-ylidene)-1-pipieidinyl]carbonyl}amino)acetate was dissolved in 8 ml of dichloromethane. 2 ml of trifluoroacetic acid was added to the obtained solution under cooling with ice, and they were stirred at room temperature for 1 hour. After the concentration under reduced pressure, the reaction mixture was dissolved in ethyl acetate. Water was added thereto and white crystals thus precipitated were taken by the filtration to obtain the title compound.

Yield: 498 mg (1.33 mmol), 76%
MS (ESI, m/z) 373 (M−H)$^−$ $^1$H-NMR (DMSO-d$_6$): 1.85-1.93 (2H, m), 2.16-2.25 (2H, m), 3.03-3.11 (2H, m), 3.39-3.47 (2H, m), 3.62 (2H, d), 6.82 (1H, br t), 6.96 (2H, s), 7.19-7.30 (4H, m), 7.35-7.40 (4H, m), 12.28 (1H, br s).

Step 3

Synthesis of N-[2-(t-butylamino)-2-oxoethyl]-4-(5H-dibenzo[a,d][7]annulen-5-ylidene)-1-piperidinecarboxamide 300 mg (0.801 mmol) of ({[4-(5H-dibenzo[a,d][7]annulen-5-ylidene)-1-piperidinyl]carbonyl}amino)acetic acid, 1.0 ml (0.961 mmol) of t-butylamine and 230 mg (1.20 mmol) of 1-ethyl-3-(3'-dimethylaminopropyl)carbodiimide hydrochloride were dissolved in 10 ml of dichloromethane. The obtained solution was stirred at room temperature for 1 hour. Water was added to the reaction mixture. After extracting with dichloromethane, the dichloromethane layer was dried over anhydrous magnesium sulfate and then concentrated under reduced pressure. The residue thus obtained was purified by the silica gel chromatography (dichloromethane:methanol=4:1 to 1:9) to obtain the title compound.

Yield: 198 mg (0.476 mmol), 60%
MS (ESI, m/z) 430 (M+H)$^+$
$^1$H-NMR (CDCl$_3$): 1.34 (9H, s), 2.11-2.18 (2H, m), 2.27-2.36 (2H, m), 3.00-3.09 (2H, m), 3.52-3.59 (2H, m), 3.79 (2H, d), 5.28 (1H, br s), 6.01 (1H, br s), 6.91 (2H, s), 7.15-7.18 (2H, m), 7.22-7.27 (2H, m), 7.30-7.35 (4H, m).

Example 48

Synthesis of N-[2-[4-(5H-dibenzo[a,d][7]annulen-5-ylidene)-1-piperidinyl]-1-(hydroxymethyl)-2-oxoethyl]-1-piperidinecarboxamide Step 1

Synthesis of Methyl 3-hydroxy-2-[(1-piperidinylcarbonyl)amino]propionate 1.00 g (6.43 mmol) of methyl 2-amino-3-hydroxypropionate hydrochloride and 960 mg (14.1 mmol) of imidazole were dissolved in 10 ml of dichloromethane. 10 ml of a solution of 1.07 g (7.07 mmol) of t-butyldimethylchlorosilane in dichloromethane was added dropwise to the obtained solution under cooling with ice, and they were stirred at room temperature for 1 hour. After concentrating under reduced pressure, ethyl acetate was added to the residue. The reaction mixture was washed with saturated aqueous ammonium chloride solution, then dried over anhydrous magnesium sulfate and concentrated under reduced pressure. The residue was dissolved in 10 ml of dichloromethane. 1.35 ml (9.65 mmol) of triethylamine and 0.97 ml (7.72 mmol) of 1-piperidinecarbonyl chloride were added dropwise to the obtained solution under cooling with ice, and they were stirred at room temperature overnight. 20 ml of chloroform was added to the reaction mixture, and they were stirred at 50° C. for 3 hours and then concentrated under reduced pressure. The residue was dissolved in 15 ml of methanol. 10 ml of 2 N hydrochloric acid was added dropwise to the obtained solution under cooling with ice, and they were stirred at room temperature for 2 hours. After the concentration under reduced pressure, ethyl acetate was added to the residue. The product was washed with 1 N aqueous hydrochloric acid solution, dried over anhydrous magnesium sulfate and concentrated under reduced pressure. The residue thus obtained was purified by the silica gel chromatography (dichloromethane:methanol=1:0 to 9:1) to obtain the title compound.

Yield: 428 mg (1.86 mmol), 29%
MS (ESI, m/z) 231 (M+H)$^+$
$^1$H-NMR (CDCl$_3$): 1.57-1.59 (6H, m), 2.98 (1H, br s), 3.36-3.39 (4H, m), 3.79 (3H, s), 3.87-3.99 (2H, m), 4.58-4.63 (1H, m), 5.43 (1H, br d).

Step 2

Synthesis of 3-hydroxy-2-[(1-piperidinylcarbonyl)amino]propionic acid 200 mg (0.869 mmol) of methyl 3-hydroxy-2-[(1-piperidinylcarbonyl)-amino]propionate was dissolved in 6 ml of a solvent mixture of methanol:tetrahydrofuran (1:1). 1.04 ml (1.04 mmol) of 1 N aqueous lithium hydroxide solution was added to the obtained solution, and they were stirred at room temperature for 30 minutes. The reaction mixture was concentrated under reduced pressure, and the concentrate was acidified with 1 N aqueous hydrochloric acid solution. After extracting with ethyl acetate, the organic layer was dried over anhydrous magnesium sulfate and then concentrated under reduced pressure to obtain the title compound.

Yield: 64 mg (0.296 mmol) (34%)
MS (ESI, m/z) 215 (M−H)$^-$
$^1$H-NMR (CD$_3$OD): 1.51-1.69 (6H, m), 3.17-3.20 (1H, m), 3.38-3.42 (4H, m), 3.80-3.94 (2H, m), 4.36 (1H, t).

Step 3

Synthesis of N-[2-[4-(5H-dibenzo[a,d][7]annulen-5-ylidene)-1-piperidinyl]-1-(hydroxymethyl)-2-oxoethyl]-1-piperidinecarboxamide 64.0 mg (0.296 mmol) of 3-hydroxy-2-[(1-piperidinylcarbonyl)amino]propionic acid, 80.9 mg (0.296 mmol) of 4-(5H-dibenzo[a,d][7]annulen-5-ylidene)piperidine and 85.1 mg (0.444 mmol) of 1-ethyl-3-(3'-dimethylaminopropyl)carbodiimide hydrochloride were dissolved in 10 ml of dichloromethane. 0.091 ml (0.651 mmol) of triethylamine was added to the obtained solution, and they were stirred at room temperature overnight. The reaction mixture was concentrated under reduced pressure. Ethyl acetate was added to the residue. After washing with saturated aqueous sodium chloride solution, the reaction product was dried over anhydrous magnesium sulfate and then concentrated under reduced pressure. The resultant product was purified by the silica gel chromatography (dichloromethane:methanol=9:1) to obtain the title compound.

Yield: 100 mg (0.213 mmol) (72%)
MS (ESI, m/z) 472 (M+H)$^+$
$^1$H-NMR (CDCl$_3$): 1.49-1.62 (6H, m), 2.26-2.35 (4H, m), 2.92-3.37 (6H, m), 3.65-3.76 (3H, m), 3.83-4.01 (1H, m), 4.08-4.31 (1H, m), 4.76-4.82 (1H, m), 5.87-5.92 (1H, m), 6.92 (2H, d), 7.14-7.18 (2H, m), 7.23-7.28 (2H, m), 7.32-7.37 (4H, m).

Example 49

Synthesis of N-[2-(t-butylamino)-1-(hydroxymethyl)-2-oxoethyl]-4-(5H-dibenzo[a,d][7]annulen-5-ylidene)-1-piperidinecarboxamide Step 1

Synthesis of 2-{[(benzyloxy)carbonyl]amino}-3-{[t-butyl(dimethyl)silyl]oxy}-propionic acid 1.50 g (6.27 mmol) of N-[(benzyloxy)carbonyl]-(DL)-serine was dissolved in 10 ml of N,N-dimethylformamide.

885 mg (13.2 mmol) of imidazole and 1.98 g (13.2 mmol) of t-butyldimethylchlorosilane were added to the obtained solution at 0° C., and they were stirred overnight. Water was added to the reaction mixture and they were stirred for 10 minutes. After extracting with ethyl acetate 3 times followed by the drying over anhydrous sodium sulfate, the solvent was evaporated under reduced pressure to obtain the title compound.

Yield: 2.21 g (6.27 mmol), 100%

$^1$H-NMR (CDCl$_3$): −0.01-0.10 (6H, m), 0.62-0.94 (9H, m), 3.60-3.80 (1H, m), 4.05-4.15 (1H, m), 4.32-4.48 (1H, m), 5.05-5.20 (2H, m), 5.59 (1H, s), 7.28-7.40 (5H, m).

Step 2

Synthesis of 2-{[(benzyloxy)carbonyl]amino}-N-(t-butyl)-3-{[t-butyl(dimethyl)-silyl]oxy}propylamide:

2.21 g (6.27 mmol) of 2-{[(benzyloxy)carbonyl]amino}-3-{[t-butyl (dimethyl)silyl]oxy}propionic acid, 1.44 g (7.52 mmol) of 1-ethyl-3-(3'-dimethylaminopropyl)carbodiimide hydrochloride, 79.0 mg (0.63 mmol) of 4-dimethylaminopyridine and 952 mg (9.41 mmol) of triethylamine were dissolved in 10 ml of dichloromethane. 504 mg (6.90 mmol) of t-butylamine was added to the obtained solution, and they were stirred overnight. Saturated aqueous ammonium chloride solution was added to the reaction mixture. After extracting with ethyl acetate 3 times followed by the drying over anhydrous sodium sulfate, the solvent was evaporated under reduced pressure. The residue was purified by the silica gel chromatography (hexane:ethyl acetate=97:3 to 88:12) to obtain the title compound.

Yield: 1.07 g (2.62 mmol), 42%

$^1$H-NMR (CDCl$_3$): 0.10 (6H, m), 0.90 (9H, s), 1.33 (9H, s), 3.56 (1H, t), 3.94-4.09 (2H, m), 5.12 (2H, m), 5.67 (1H, s), 6.30 (1H, s), 7.28-7.39 (5H, m).

Step 3

Synthesis of 2-amino-N-(t-butyl)-3-{[t-butyl(dimethyl)silyl]oxy}propylamide 500 mg of palladium carbon (10% w/v) in 5 ml of ethanol was added to 990 mg (2.42 mmol) of 2-{[(benzyloxy)carbonyl]amino}-N-(t-butyl)-3-{[t-butyl-(dimethyl)silyl]oxy}propylamide, and they were stirred in hydrogen gas atmosphere overnight. The reaction mixture was filtered, and the solvent was evaporated under reduced pressure to obtain the title compound. After drying on anhydrous sodium sulfate, the solvent was evaporated under reduced pressure to obtain the title compound.

Yield: 620 mg (2.26 mmol), 93%

$^1$H-NMR (CDCl$_3$): 0.06 (6H, s), 0.89 (9H, s), 1.24 (9H, s), 1.63 (2H, s), 3.30 (1H, t), 3.76 (2H, d), 7.10 (1H, br s).

Step 4

Synthesis of N-[2-(t-butylamino)-1-({[t-butyl(dimethyl)silyl]oxy}methyl)-2-oxoethyl]-4-(5H-dibenzo[a,d][7]annulen-5-ylidene)-1-piperidinecarboxamide 59.1 mg (0.364 mmol) of 1,1'-carbonylbis-1H-imidazole and 36.9 mg (0.364 mmol) of triethylamine were dissolved in 4 ml of dichloromethane. A solution of 100 mg (0.364 mmol) of 2-amino-N-(t-butyl)-3-{[t-butyl(dimethyl)-silyl]oxy}propylamide in 2 ml of dichloromethane was slowly added to the obtained solution. After stirring for 2 hours, a solution of 99.6 mg (0.364 mmol) of 2-[4-(5H-dibenzo[a,d][7]annulen-5-ylidene)-1-piperidinyl]ethylamine and 36.9 mg (0.364 mmol) of triethylamine in 2 ml of dichloromethane was slowly added to the reaction mixture. After stirring them overnight, the solvent was evaporated under reduced pressure and the residue was purified by the silica gel chromatography (hexane:ethyl acetate=9:1 to 7:3) to obtain the title compound.

Yield: 113 mg (0.197 mmol), 54%

$^1$H-NMR (CDCl$_3$): 0.11 (6H, d), 0.90 (9H, s), 1.24 (9H, s), 2.10-2.20 (2H, m), 2.25-2.40 (2H, m), 3.30-3.12 (2H, m), 3.46 (1H, t), 3.50-3.61 (2H, m), 3.97 (1H, dd), 4.10-4.18 (1H, m), 5.57 (1H, d), 6.60 (1H, s), 6.91 (2H, s), 7.13-7.36 (8H, m).

Step 5

Synthesis of N-[2-(t-butylamino)-1-(hydroxymethyl)-2-oxoethyl]-4-(5H-dibenzo[a,d][7]annulen-5-ylidene)-1-piperidinecarboxamide 113 mg (0.197 mmol) of N-[2-(t-butylamino)-1-({[t-butyl(dimethyl)-silyl]oxy}methyl)-2-oxoethyl]-4-(5H-dibenzo[a,d][7]annulen-5-ylidene)-1-piperidinecarboxamide was dissolved in 3 ml of tetrahydrofuran. 0.22 ml of 1 M tetrabutylammonium fluoride/tetrahydrofuran solution was added to the obtained solution, and they were stirred for 30 minutes. After the purification by the silica gel chromatography (hexane:ethyl acetate=9:1 to 3:2), the title compound was obtained.

Yield: 66.9 mg (0.146 mmol), 74%

MS (ESI, m/z) 460 (M+H)$^+$ $^1$H-NMR (CDCl$_3$): 1.35 (9H, s), 2.13-2.26 (2H, m), 2.28-2.42 (2H, m), 3.01-3.15 (2H, m), 3.50-3.64 (3H, m), 4.03-4.26 (2H, m), 5.64 (1H, d), 6.77 (1H, br s), 6.94 (2H, s), 7.16-7.40 (8H, m).

Example 50

Synthesis of N-[3-[4-(5H-dibenzo[a,d][7]annulen-5-ylidene)-1-piperidinyl]-1-(hydroxymethyl)-3-oxo-propyl]-2,2-dimethylpropanamide Step 1

Synthesis of 3-[(t-butoxycarbonyl)amino]-4-methoxy-4-oxobutanoic acid 2.0 g (6.18 mmol) of 4-(benzyloxy)-2-[(t-butoxycarbonyl)amino]-4-oxobutanoic acid was dissolved in a solvent mixture of 6 ml of methanol and 12 ml of toluene. 3.7 ml of 2 M trimethylsilyldiazomethane/hexane solution was added to the obtained solution and they were stirred for 3 hours. Additional 0.5 ml of 2 M trimethylsilyldiazomethane/hexane solution was added to the reaction mixture and they were stirred for 1 hour. The solvent was evaporated under reduced pressure. The residue was dissolved in 20 ml of ethanol. 2.0 g of palladium carbon (10% w/v) was added to the obtained solution, and they were stirred in hydrogen gas atmosphere for 19 hours. After the filtration, the solvent was evaporated under reduced pressure to obtain the title compound.

Yield: 1.50 g (6.07 mmol), 98%

$^1$H-NMR (DMSO-d$_6$): 1.38 (9H, s), 2.49-2.70 (2H, m), 3.62 (3H, s), 4.32 (1H, m), 7.23 (1H, d).

Step 2

Synthesis of methyl 2-[(t-butoxycarbonyl)amino]-4-[4-(5H-dibenzo[a,d][7]-annulen-5-ylidene)-1-piperidinyl]-4-oxobutanoate 1.10 g (4.04 mmol) of 4-(5H-dibenzo[a,d][7]annulen-5-ylidene)-1-piperidine, 1.00 g (4.04 mmol) of 3-[(t-butoxycarbonyl)amino]-4-methoxy-4-oxobutanoic acid, 930 mg (4.85 mmol) of 1-ethyl-3-(3'-dimethylaminopropyl)-carbodiimide hydrochloride and 48.9 mg (0.40 mmol) of 4-dimethylaminopyridine were dissolved in 10 ml of dichloromethane. 532 mg (5.25 mmol) of triethylamine was added to the obtained solution, and they were stirred overnight. Saturated aqueous ammonium chloride solution was added to the reaction mixture. After extracting with ethyl acetate 3 times, the organic layer was washed with saturated sodium hydrogencarbonate solution and then dried over anhydrous sodium sulfate. The solvent was evaporated under reduced pressure, and the residue was purified by the silica gel chromatography (hexane:ethyl acetate=89:11) to obtain the title compound.

Yield: 1.17 g (2.32 mmol), 58%

MS (ESI, m/z) 503 (M+H)$^+$ $^1$H-NMR (CDCl$_3$): 1.43 (9H, d), 2.10-2.38 (4H, m), 2.73 (1H, m), 2.90-3.18 (3H, m), 3.48-3.54 (1H, m), 3.73 (3H, d), 3.83-3.95 (1H, m), 4.49-4.58 (1H, m), 5.77 (1H, t), 6.91 (2H, s), 7.16-7.36 (8H, m).

Step 3

Synthesis of methyl 4-[4-(5H-dibenzo[a,d][7]annulen-5-ylidene)-1-piperidinyl]-2-[(2,2-dimethylpropanoyl)amino]-4-oxobutanoate 600 mg (1.19 mmol) of methyl 2-[(t-butoxycarbonyl)amino]-4-[4-(5H-dibenzo[a,d][7]annulen-5-ylidene)-1-piperidinyl]-4-oxobutanoate was dissolved in 5 ml of ethyl acetate. 0.5 ml of 4 N hydrochloric acid/ethyl acetate solution was added to the obtained solution, and they were stirred at 0° C. for 3 hours. After stirring at room temperature overnight, the solvent was evaporated under reduced pressure. The residue was dissolved in 10 ml of dichloromethane. 602 mg (5.95 mmol) of triethylamine and 158 mg (1.31 mmol) of pivaloyl chloride were added to the obtained solution, and they were stirred for 10 minutes. Saturated aqueous sodium hydrogencarbonate solution and water were added to the reaction mixture. After extracting with ethyl acetate 3 times followed by the drying over anhydrous sodium sulfate, the solvent was evaporated under reduced pressure, and the residue was purified by the silica gel chromatography (hexane:ethyl acetate=89:11 to 65:35) to obtain the title compound.

Yield: 468 mg (0.962 mmol), 81%

MS (ESI, m/z) 487 (M+H)$^+$ $^1$H-NMR (CDCl$_3$): 1.20 (9H, d), 2.10-2.38 (4H, m), 2.60-2.81 (1H, m), 2.85-3.20 (3H, m), 3.42-3.57 (1H, m), 3.74 (3H, d), 3.80-3.98 (1H, m), 4.85 (1H, m), 6.92 (2H, s), 7.03 (1H, d), 7.11-7.38 (8H, m).

Step 4

Synthesis of N-[3-[4-(5H-dibenzo[a,d][7]annulen-5-ylidene)-1-piperidinyl]-1-(hydroxymethyl)-3-oxopropyl]-2,2-dimethylpropanamide 106 mg (0.218 mmol) of methyl 4-[4-(5H-dibenzo[a,d][7]annulen-5-ylidene)-1-piperidinyl]-2-[(2,2-dimethylpropanoyl)amino]-4-oxobutanoate was dissolved in 3 ml of tetrahydrofuran. 5.7 mg (0.261 mmol) of lithium borohydride was added to the obtained solution at 0° C. The reaction mixture was stirred for 1.5 hours and then saturated aqueous ammonium chloride solution was added thereto. After extracting with ethyl acetate 3 times, the extract was dried over anhydrous sodium sulfate. The solvent was evaporated under reduced pressure to obtain the title compound.

Yield: 72.3 mg (0.158 mmol), 72%

MS (ESI, m/z) 459 (M+H)$^+$ $^1$H-NMR (CDCl$_3$): 1.18 (9H, d), 2.11-2.35 (4H, m), 2.58-2.71 (2H, m), 2.88-3.21 (2H, m), 3.56-3.79 (3H, m), 3.85-4.15 (3H, m), 6.95-7.00 (3H, m), 7.11-7.33 (8H, m).

Example 51

Synthesis of cyclohexyl 2-[4-(5H-dibenzo[a,d][7]annulen-5-ylidene)-1-piperidinyl]-2-oxoethylcarbamate Step 1

Synthesis of {[(cyclohexyloxy)carbonyl]amino}acetic acid 620 mg (4.80 mmol) of ethyl isocyanatoacetate was dissolved in 5 ml of dichloromethane. 10 ml of a solution of 0.56 ml (5.28 mmol) of cyclohexanol in 10 ml of dichloromethane was added to the obtained solution under cooling with ice, and they were stirred at room temperature for 15 minutes. The reaction mixture was concentrated under reduced pressure. 5.8 ml of 1 N aqueous lithium hydroxide solution was added to the concentrate, and the obtained mixture was stirred in a solvent mixture of methanol:water=2:1 at room temperature for 2 hours. The reaction mixture was concentrated under reduced pressure. Water was added to the concentrate and the resultant aqueous layer was washed with ethyl acetate. 0.1 N aqueous hydrochloric acid solution was added to the aqueous layer to control pH at 2 to 3. After extracting with ethyl acetate, the organic layer was dried over anhydrous magnesium sulfate and then concentrated under reduced pressure to obtain the title compound.

Yield: 86.1 mg (0.428 mmol), 8.9%

MS (ESI, m/z) 200 (M−H)$^−$ $^1$H-NMR (CDCl$_3$): 1.22-1.56 (6H, m), 1.65-1.76 (2H, m), 1.80-1.92 (2H, m), 3.95-4.02 (2H, m), 4.65 (1H, br s), 5.15 (1H, br s).

Step 2

Synthesis of cyclohexyl 2-[4-(5H-dibenzo[a,d][7]annulen-5-ylidene)-1-piperidinyl]-2-oxoethylcarbamate 86.1 mg (0.428 mmol) of {[(cyclohexyloxy)carbonyl]amino}acetic acid, 176 mg (0.642 mmol) of 4-(5H-dibenzo[a,d][7]annulen-5-ylidene)piperidine and 98.5 mg (0.514 mmol) of 1-ethyl-3-(3'-dimethylaminopropyl)carbodiimide hydrochloride were suspended in 10 ml of dichloromethane. 0.086 ml (0.617 mmol) of triethylamine was added to the obtained suspension, and they were stirred at room temperature for 3 hours. The resultant mixture was concentrated under reduced pressure and then ethyl acetate was added to the residue. The resultant mixture was washed with saturated aqueous sodium hydrogencarbonate solution, dried over anhydrous magnesium sulfate and then concentrated under reduced pressure. The obtained residue was purified by the silica gel chromatography (hexane:ethyl acetate=95:5 to 1:4) to obtain the title compound.

Yield: 82.9 mg (0.182 mmol), 43%

MS (ESI, m/z) 457 (M+H)$^+$ $^1$H-NMR (CDCl$_3$): 1.32-1.42 (4H, m), 1.45-1.57 (3H, m), 1.64-1.75 (2H, m), 1.80-1.90 (2H, m), 2.15-2.34 (4H, m), 2.99-3.08 (2H, m), 3.41-3.47 (1H, m), 3.88-3.99 (2H, m), 4.58-4.67 (1H, m), 5.62 (1H, br s), 6.92 (2H, s), 7.15-7.18 (2H, m), 7.23-7.24 (1H, m), 7.28-7.29 (1H, m), 7.32-7.37 (4H, m).

Example 52

Synthesis of 1-methylcyclopentyl 2-[4-(5H-dibenzo[a,d][7]annulen-5-ylidene)-1-piperidinyl]-2-oxoethylcarbamate Step 1

Synthesis of ({[(1-methylcyclopentyl)oxy]carbonyl}amino)acetic acid 500 mg (3.87 mmol) of ethyl isocyanatoacetate was dissolved in 5 ml of dichloromethane. 0.05 ml of 4 N hydrochloric acid/1,4-dioxane solution was added to the obtained solution. 465 mg (4.64 mmol) of 1-methylcyclopentanol was added to the resultant mixture, and they were stirred for 3 hours 30 minutes. 10 ml of methanol and 12 ml of 1 N aqueous sodium hydroxide solution were added thereto and they were stirred for 15 minutes. The organic solvent was evaporated under reduced pressure. After extracting with dichloromethane twice, the aqueous layer was neutralized with 1 N aqueous hydrochloric acid solution. The product was extracted with dichloromethane 3 times and then dried over anhydrous sodium sulfate. The solvent was evaporated under reduced pressure to obtain the title compound. The product was subjected to the next reaction without any purification.

Yield: 43.0 mg (0.214 mmol), 5.5%

$^1$H-NMR (CDCl$_3$): (Only the main peaks are shown because the product contained impurities) 1.56 (3H, s), 5.22 (1H, d).

Step 2

Synthesis of 1-methylcyclopentyl 2-[4-(5H-dibenzo[a,d][7]annulen-5-ylidene)-1-piperidinyl]-2-oxoethylcarbamate 70.2 mg (0.257 mmol) of 4-(5H-dibenzo[a,d][7]annulen-5-ylidene)-1-piperidine, 43.0 mg (0.214 mmol) of ({[(1-methylcyclopentyl)oxy]carbonyl}amino)acetic acid, 49.3 mg (0.257 mmol) of 1-ethyl-3-(3'-dimethylaminopropyl)carbodiimide hydrochloride and 3.6 mg (0.03 mmol) of 4-dimethylaminopyridine were dissolved in 1 ml of dichloromethane. 26.0 mg (0.257 mmol) of triethylamine was added to the obtained solution, and they were stirred overnight. After the purification by the silica gel chromatography (hexane:ethyl acetate=9:1 to 3:2), the title compound was obtained.

Yield: 56.7 mg (0.124 mmol), 58%

MS (ESI, m/z) 457 (M+H)$^+$ $^1$H-NMR (CDCl$_3$): 1.48-1.76 (9H, m), 2.00-2.36 (6H, m), 3.02 (2H, m), 3.37-3.50 (1H, m), 3.80-4.05 (3H, m), 5.53 (1H, s), 6.92 (2H, s), 7.13-7.20 (2H, m), 7.22-7.37 (6H, m).

Example 53

Synthesis of tetrahydro-2H-pyran-4-yl 2-[4-(5H-dibenzo[a,d][7]annulen-5-ylidene)-1-piperidinyl]-2-oxoethylcarbamate Step 1

Synthesis of Ethyl {[(tetrahydro-2H-pyran-4-yloxy)carbonyl]amino}acetate 0.600 ml (4.80 mmol) of ethyl isocyanatoacetate was dissolved in dichloromethane. 0.06 ml of 4 N hydrochloric acid/1,4-dioxane solution was added to the obtained solution, and they were stirred at room temperature for 5 minutes. 0.503 ml (5.28 mmol) of tetrahydro-4H-4-pyranol was added to the reaction mixture, and they were stirred at room temperature overnight. After concentrating the reaction mixture under reduced pressure, the residue was purified by the silica gel chromatography (hexane:ethyl acetate=9:1 to 1:4), the title compound was obtained.

Yield: 584 mg (2.53 mmol), 53%

$^1$H-NMR (CDCl$_3$): 1.29 (3H, t), 1.61-1.73 (2H, m), 1.89-1.97 (2H, m), 3.49-3.56 (2H, m), 3.87-3.96 (4H, m), 4.22 (2H, q), 4.81-4.90 (1H, m), 5.13-5.20 (1H, br s).

Step 2

Synthesis of {[(tetrahydro-2H-pyran-4-yloxy)carbonyl]amino}acetic acid

The title compound was obtained from 287 mg (1.24 mmol) of ethyl {[(tetrahydro-2H-pyran-4-yloxy)carbonyl]amino}acetate and 1.49 ml of 1 N aqueous lithium hydroxide solution in the same manner as that in Step 2 in Example 43.

Yield: 269 mg (1.32 mmol), 100%

MS (ESI, m/z) 202 (M−H)$^-$ $^1$H-NMR (DMSO-d$_6$): 1.40-1.52 (2H, m), 1.77-1.83 (2H, m), 3.28-3.43 (4H, m), 3.73-3.80 (2H, m), 4.63 (1H, sept), 6.31 (1H, br s).

Step 3

Synthesis of tetrahydro-2H-pyran-4-yl 2-[4-(5H-dibenzo[a,d][7]annulen-5-ylidene)-1-piperidinyl]-2-oxoethylcarbamate Tetrahydro-2H-pyran-4-yloxy)carbonyl]amino}acetic acid, 563 mg (2.06 mmol) of 4-(5H-dibenzo[a,d][7]annulen-5-ylidene) piperide and 563 mg (1.65 mmol) of 1-ethyl-3-(3'-dimethylaminopropyl)carbodiimide hydrochloride were suspended in 10 ml of dichloromethane. 0.23 ml (1.65 mmol) of triethylamine was added to the obtained suspension, and they were stirred at room temperature overnight. 20 ml of dimethylformamide was added to the reaction mixture, and they were stirred at 50° C. for 3 hours. 263 mg (1.37 mmol) of 1-ethyl-3-(3'-dimethylaminopropyl)carbodiimide hydrochloride, 50 mg (0.41 mmol) of 4-dimethylaminopyridine and 0.19 ml (1.37 mmol) of triethylamine were added to the reaction mixture, and they were stirred at 50° C. overnight. The resultant mixture was concentrated under reduced pressure and then ethyl acetate was added to the residue. The resultant mixture was washed with saturated aqueous sodium hydrogencarbonate solution and saturated aqueous sodium chloride solution. The organic layer was dried over anhydrous magnesium sulfate and then concentrated under reduced pressure. The obtained residue was purified by the silica gel chromatography (hexane:ethyl acetate=3:1 to 1:2) to obtain the title compound.

Yield: 32.1 mg (0.0700 mmol), 5.1%

MS (ESI, m/z) 459 (M+H)$^+$ $^1$H-NMR (CDCl$_3$): 1.62-1.72 (2H, m), 1.87-1.96 (2H, m), 2.15-2.33 (4H, m), 2.99-3.08 (2H, m), 3.42-3.56 (3H, m), 3.86-4.13 (5 H, m), 4.81-4.86 (1H, m), 5.70 (1H, br t), 6.92 (2H, s), 7.15-7.18 (2H, m), 7.23-7.29 (2H, m), 7.32-7.37 (4H, m).

Example 54

Synthesis of methyl 4-[4-(5H-dibenzo[a,d][7]annulen-5-ylidene)-1-piperidinyl]-2-[(2,2-dimethylpropanoyl)amino]-4-oxobutanoate The compound synthesized in Step 3 in Example 50

Example 55

Synthesis of methyl 2-[(t-butoxycarbonyl)amino]-4-[4-(5H-dibenzo[a,d][7]-annulen-5-ylidene)-1-piperidinyl]-4-oxobutanoate The compound synthesized in Step 2 in Example 50.

Example 56

Synthesis of 2-[(t-butoxycarbonyl)amino]-4-[4-(5H-dibenzo[a,d][7]annulen-5-ylidene)-1-piperidinyl]-4-oxobutanoic acid 150 mg (0.298 mmol) of the compound of Example 55 was dissolved in 2 ml of a solvent mixture of methanol:tetrahydrofuran=1:1. 0.36 ml of 1 N aqueous lithium hydroxide solution was added to the obtained solution at room temperature. After stirring for 3.5 hours, the solvent was evaporated under reduced pressure. Saturated aqueous sodium hydrogencarbonate solution was added to the residue, and the obtained mixture was washed with diethyl ether. The aqueous layer was adjusted to pH 4 with 1 N hydrochloric acid. After extracting with ethyl acetate, the organic layer was dried over anhydrous magnesium sulfate. The solvent was evaporated under reduced pressure to obtain the title compound.

Yield: 150 mg (0.307 mmol), quantitative.
MS (ESI, m/z) 172 (M+H)$^+$
$^1$H-NMR (CDCl$_3$): 1.43 (9H, d), 2.16-2.44 (4H, m), 2.58-2.71 (1H, m), 2.93-3.24 (3H, m), 3.52-3.58 (1H, m), 3.91-4.04 (1H, m), 4.46-4.54 (1H, m), 5.78 (1H, br d), 6.92 (2H, d), 7.14-7.19 (2H, m), 7.23-7.29 (2H, m), 7.30-7.37 (4H, m).

Example 57

Synthesis of 4-[4-(5H-dibenzo[a,d][7]annulen-5-ylidene)-1-piperidinyl]-2-[(2,2-dimethylpropanoyl)amino]-4-oxobutanoic acid The title compound was obtained from the compound synthesized in Example 54 in the same manner as that of Example 56.

Yield: 133 mg (0.281 mmol), quantitative.
MS (ESI, m/z) 471 (M−H)$^-$
$^1$H-NMR (CDCl$_3$): 1.20 (9H, d), 2.21-2.34 (3H, m), 2.42-2.61 (2H, m), 2.98-3.30 (3H, m), 3.54-3.63 (1H, m), 3.97-4.13 (1H, m), 4.59-4.67 (1H, m), 6.92 (2H, d), 7.07 (1H, br d), 7.13-7.19 (2H, m), 7.23-7.30 (2H, m), 7.32-7.37 (4H, m).

Example 58

Synthesis of (S)—N-[3-[4-(5H-dibenzo[a,d][7]annulen-5-ylidene)-1-piperidinyl]-1-(hydroxymethyl)-3-oxopropyl]-2,2-dimethylpropanamide The title compound was obtained from (S)-4-(benzyloxy)-2-[(t-butoxycarbonyl)amino]-4-oxobutanoic acid in the same manner as that of Example 50.

MS (ESI, m/z) 459 (M+H)$^+$
$^1$H-NMR (CDCl$_3$): 1.18 (9H, d), 2.11-2.37 (4H, m), 2.57-2.82 (2H, m), 2.89-3.22 (2H, m), 3.58-3.80 (3H, m), 3.87-4.13 (3H, m), 6.92 (2H, s), 6.89-6.99 (1H, m), 7.13-7.20 (2H, m), 7.23-7.38 (6H, m).

Example 59

Synthesis of (R)—N-[3-[4-(5H-dibenzo[a,d][7]annulen-5-ylidene)-1-piperidinyl]-1-(hydroxymethyl)-3-oxopropyl]-2,2-dimethylpropanamide The title compound was obtained from (R)-4-(benzyloxy)-2-[(t-butoxycarbonyl)amino]-4-oxobutanoic acid in the same manner as that in Example 50.

MS (ESI, m/z) 459 (M+H)$^+$
$^1$H-NMR (CDCl$_3$): 1.18 (9H, d), 2.12-2.37 (4H, m), 2.59-2.82 (2H, m), 2.91-3.22 (2H, m), 3.57-3.82 (3H, m), 3.86-4.13 (3H, m), 6.92 (2H, s), 6.89-6.97 (1H, m), 7.14-7.19 (2H, m), 7.22-7.37 (6H, m).

Example 60

Synthesis of t-butyl 3-[4-(5H-dibenzo[a,d][7]annulen-5-ylidene)-1-piperidinyl]-1-(hydroxymethyl)-3-oxopropylcarbamate The title compound was obtained from the compound in step 2 in Example 50 in the same manner as that in Step 4 in Example 50.

Yield: 56.3 mg (0.119 mmol), 55%
MS (ESI, m/z) 475 (M+H)$^+$
$^1$H-NMR (CDCl$_3$): 1.42 (9H, d), 2.16-2.35 (4H, m), 2.62-2.80 (2H, m), 2.93-3.02 (1H, m), 3.07-3.16 (1H, m), 3.58-3.75 (4H, m), 3.88-3.98 (2H, m), 5.49 (1, br s), 6.92 (2H, s), 7.14-7.19 (2H, m), 7.23-7.28 (2H, m), 7.31-7.37 (4H, m).

Example 61

Synthesis of t-butyl 3-[4-(5H-dibenzo[a,d][7]annulen-5-yl)-1-piperazinyl]-3-oxopropylcarbamate Step 1

Synthesis of 5H-dibenzo[a,d][7]annulen-5-ol 4 ml of water, 0.45 ml of 1 N aqueous sodium hydroxide solution and 20 ml of a suspension of 1.50 g (7.27 mmol) of dibenzosuberenone in methanol were added to 200 mg (5.29 mmol) of sodium borohydride, and they were stirred overnight. Crystals thus precipitated were taken by the filtration, washed with water and dissolved in ethyl acetate. After drying over anhydrous magnesium sulfate, the solvent was evaporated under reduced pressure to obtain the title compound.

Yield: 1.48 g (7.11 mmol), 98%
$^1$H-NMR (CDCl$_3$): 2.41 (1H, d), 5.43 (1H, d), 7.11 (2H, s), 7.25-7.31 (2H, m), 7.36-7.44 (4H, m), 7.66 (2H, d).

Step 2

Synthesis of t-butyl 4-(5H-dibenzo[a,d][7]annulen-5-yl)-1-piperazine carboxylate 750 mg (3.60 mmol) of the compound obtained in step 1 described above was dissolved in 8 ml of benzene. 0.02 ml of pyridine was added to the obtained solution, and 3.5 ml (48.2 mmol) of thionyl chloride was added to the obtained mixture under cooling with ice. After stirring the reaction mixture at 0° C. for 1 hour and then at room temperature for 2 hours, the solvent was evaporated under reduced pressure. 10 ml of tetrahydrofuran was added to the residue. 2.5 ml (18 mmol) of triethylamine and 805 mg (4.32 mmol) of t-butyl piperazinecarboxylate were added to reaction mixture under cooling with ice. The temperature of the mixture was slowly elevated to room temperature, and it was stirred overnight. The solvent was evaporated under reduced pressure. Dichloromethane was added to the residue. After washing with water and saturated aqueous sodium chloride solution, the organic layer was dried over anhydrous magnesium sulfate. The solvent was evaporated under reduce pressure, and the residue was purified by the basic silica gel chromatography (hexane:dichloromethane=9:1) to obtain the title compound.

Yield: 1.25 g (3.31 mmol), 92%
MS (ESI, m/z) 377 (M+H)$^+$
$^1$H-NMR (CDCl$_3$): 1.39 (9H, s), 1.92 (4H, br t), 3.13 (4H, br t), 4.26 (1H, s), 6.96 (2H, s), 7.27-7.39 (8H, m).

Step 3

Synthesis of t-butyl 3-[4-(5H-dibenzo[a,d][7]annulen-5-yl)-1-piperazinyl]-3-oxopropylcarbamate 300 mg (0.797 mmol) of the compound obtained in the above-described step 2 was dissolved in 5 ml of 1,4-dioxane. 1 ml of 4 N hydrochloric acid/1,4-dioxane was added to the obtained solution under cooling with ice, and they were stirred at room temperature for 7.5 hours. The solvent was evaporated under reduced pressure. Ethyl acetate was added to the residue. After washing with 1 N aqueous sodium hydroxide solution, the organic layer was dried over anhydrous sodium sulfate. The solvent was evaporated under reduced pressure. 175 mg (0.925 mmol) of 3-[(t-butoxycarbonyl)amino]propanoic acid and 191 mg (0.925 mmol) of 1-ethyl-3-(3'-dimethylaminopropyl)carbodiimide hydrochloride were added to the residue, and the resultant mixture was dissolved in 15 ml of dichloromethane. Then 0.13 ml (0.925 mmol) of triethylamine and 10 mg (0.08 mmol) of dimethylaminopyridine were added to the obtained solution, and they were stirred at room temperature overnight. The solvent was evaporated under reduced pressure. Ethyl acetate was added to the residue. After washing with saturated aqueous sodium hydrogencarbonate solution and saturated aqueous sodium chloride solution, the organic layer was dried over anhydrous magnesium sulfate. The solvent was evaporated under reduced pressure. The residue was purified by the silica gel chromatography (hexane:ethyl acetate=19:1 to 1:4) to obtain the title compound.

Yield: 181 mg (0.404 mmol), 52%
MS (ESI, m/z) 448 (M+H)$^+$
$^1$H-NMR (CDCl$_3$): 1.41 (9H, s), 1.95 (4H, br t), 2.38 (2H, br t), 3.13 (2H, br t), 3.30-3.38 (4H, m), 4.27 (1H, s), 5.26 (1H, br s), 6.96 (2H, s), 7.28-7.40 (8H, m).

Example 62

Synthesis of (S)—N-{2-amino-3-[4-(5H-dibenzo[a,d][7]annulen-5-ylidene)-1-piperidinyl]-3-oxopropyl}-2,2-dimethylpropanamide hydrochloride Step 1

Synthesis of t-butyl(S)-2-[4-(5H-dibenzo[a,d][7]annulen-5-ylidene)-1-piperidinyl]-1-{[(2,2-dimethylpropanoyl)amino]methyl}-2-oxoethylcarbamate 1.70 g (8.09 mmol) of (S)-3-amino-2-[(t-butoxycarbonyl)amino]-propanoic acid 0.3 hydrate was dissolved in 40 ml of dichloromethane. 2.74 ml (19.6 mmol) of triethylamine and 1.20 ml (9.71 mmol) of pivaloyl chloride were added to the obtained solution under cooling with ice, and they were stirred for 4 hours while the temperature was elevated to room temperature. An aqueous ammonium chloride solution was added to the reaction mixture under cooling with ice, and the solvent was evaporated under reduced pressure. Ethyl acetate was added to the residue. After washing with 0.1 N hydrochloric acid, the organic layer was dried over anhydrous magnesium sulfate and then the solvent was evaporated under reduced pressure. 2.03 g (10.6 mmol) of 1-ethyl-3-(3'-dimethylaminopropyl)carbodiimide hydrochloride was added to the residue, and the resultant mixture was dissolved in 70 ml of dichloromethane. 1.48 ml (10.6 mmol) of triethylamine, 2.00 g (7.33 mmol) of 4-(5H-dibenzo[a,d][7]annulen-5-ylidene)-1-piperidine and 86 mg (0.7 mmol) of dimethylaminopyridine were added to the obtained solution under cooling with ice, and they were stirred at room temperature overnight. The solvent was evaporated under reduced pressure, and ethyl acetate was added to the residue. After washing with saturated sodium hydrogencarbonate solution, the organic layer was dried over anhydrous magnesium sulfate. The solvent was evaporated under reduced pressure, and the residue was purified by the silica gel chromatography (hexane:ethyl acetate=9:1 to 1:3) to obtain the title compound.

Yield: 1.40 g (2.57 mmol), 32%
MS (ESI, m/z) 544 (M+H)$^+$
$^1$H-NMR (CDCl$_3$): 1.17 (9H, d), 1.42 (9H, d), 2.15-2.46 (4H, m), 2.90-3.25 (3H, m), 3.52-4.00 (3H, m), 4.68-4.78 (1H, m), 5.72 (1H, br t), 6.38 (1H, br d), 6.91 (2H, s), 7.13-7.19 (2H, m), 7.23-7.28 (2H, m), 7.32-7.37 (4H, m).

Step 2

Synthesis of (S)—N-{2-amino-3-[4-(5H-dibenzo[a,d][7]annulen-5-ylidene)-1-piperidinyl]-3-oxopropyl}-2,2-dimethylpropanamide hydrochloride 1.40 g (2.57 mmol) of the compound obtained in step 1 described above was dissolved in 12 ml of ethyl acetate. 10 ml of 4 N hydrochloric acid/ethyl acetate was added to the obtained solution under cooling with ice. The temperature was gradually elevated to room temperature. After stirring for 3.5 hours, the solvent was evaporated under reduced pressure to obtain the title compound.

Yield: 1.08 g (2.26 mmol), 88%
MS (ESI, m/z) 444 (M+H)$^+$
$^1$H-NMR (CDCl$_3$): 1.14 (9H, d), 2.04-2.46 (4H, m), 2.81-3.02 (1H, m), 3.20-3.43 (2H, m), 3.58-3.89 (3H, m), 4.41 (1H, br s), 6.88 (2H, d), 7.07-7.16 (2H, m), 7.22-7.34 (6H, m), 7.70 (1H, br s), 8.42 (2H, br s).

Example 63

Synthesis of (R)—N-{2-amino-3-[4-(5H-dibenzo[a,d][7]annulen-5-ylidene)-1-piperidinyl]-3-oxopropyl}-2,2-dimethylpropanamide hydrochloride The title compound was obtained in the same manner as that in Example 62.

MS (ESI, m/z) 444 (M+H)$^+$
$^1$H-NMR (CDCl$_3$): 1.14 (9H, d), 1.82-2.50 (4H, m), 2.80-3.04 (1H, m), 3.16-3.94 (5H, m), 4.41 (1H, br s), 6.88 (2H, d), 7.05-7.17 (2H, m), 7.21-7.36 (6H, m), 7.72 (1H, br s), 8.40 (2H, br s).

Example 64

Synthesis of N-[3-[4-(5H-dibenzo[a,d][7]annulen-5-yl)-1-piperazinyl]-1-(hydroxymethyl)-3-oxopropyl]-2,2-dimethylpropanamide hydrochloride Step 1

Synthesis of methyl 2-[(t-butoxycarbonyl)amino]-4-[4-(5H-dibenzo[a,d][7]-annulen-5-yl)-1-piperazinyl]-4-oxobutanoate 442 mg (1.17 mmol) of the compound obtained in Step 2 in Example 61 was dissolved in 10 ml of 1,4-dioxane. 1.5 ml of 4 N hydrochloric acid/1,4-dioxane was added to the obtained solution under cooling with ice, and they were stirred at room temperature overnight. 0.1 ml of 4 N hydrochloric acid/1,4-dioxane was added to the resultant mixture under cooling with ice, and they were stirred at room temperature for 3 hours. The solvent was evaporated under reduced pressure. Ethyl acetate was added to the residue. After washing with 1 N aqueous sodium hydroxide solution, the organic layer was dried over anhydrous sodium sulfate and then the solvent was evaporated under reduced pressure. 347 mg (1.40 mmol) of 3-[(t-butoxycarbonyl)amino]-4-methoxy-4-butanoic acid and 314 mg (1.64 mmol) of 1-ethyl-3-(3'-dimethylaminopropyl)carbodiimide hydrochloride were added to the residue, and the resultant mixture was dissolved in 10 ml of dichloromethane. 0.20 ml (1.64 mmol) of triethylamine and 17 mg (0.12 mmol) of dimethylaminopyridine were added to the obtained solution, and they were stirred at room temperature overnight. The solvent was evaporated under reduced pressure, and ethyl acetate was added to the residue. After washing with saturated sodium hydrogencarbonate solution, the organic layer was dried over anhydrous magnesium sulfate. The solvent was evaporated under reduced pressure, and the residue was purified by the silica gel column chromatography (hexane:ethyl acetate=100:1 to 65:35) to obtain the title compound.

Yield: 524 mg (1.04 mmol), 89%
MS (ESI, m/z) 506 (M+H)+
1H-NMR (CDCl3): 1.43 (9H, s), 1.93-1.98 (4H, m), 2.64 (1H, dd), 3.00 (1H, dd), 3.12 (2H, br t), 3.28 (2H, br t), 3.71 (3H, s), 4.27 (1H, s), 4.50 (1H, dt), 5.73 (1H, d), 6.95 (2H, s), 7.27-7.40 (8H, m).

Step 2

Synthesis of Methyl 4-[4-(5H-dibenzo[a,d][7]annulen-5-yl)-1-piperazinyl]-2-[(2,2-dimethylpropanoyl)amino]-4-oxobutanoate The title compound was obtained from 522 mg (1.32 mmol) of the compound obtained in step 1 described above in the same manner as that in Step 3 in Example 50.

Yield: 406 mg (0.829 mmol), 63%
MS (ESI, m/z) 490 (M+H)+
1H-NMR (CDCl3): 1.19 (9H, s), 1.92-1.99 (4H, m), 2.62 (1H, dd), 3.02 (1H, dd), 3.13 (2H, br t), 3.28 (2H, br t), 3.71 (3H, s), 4.27 (1H, s), 4.80 (1H, dt), 6.95 (2H, s), 6.99 (1H, br d), 7.28-7.40 (8H, m).

Step 3

Synthesis of N-[3-[4-(5H-dibenzo[a,d][7]annulen-5-yl)-1-piperazinyl]-1-(hydroxymethyl)-3-oxopropyl]-2,2-dimethylpropanamide hydrochloride The title compound was obtained from 405 mg (0.827 mmol) of the compound obtained in step 2 described above by the same method as that in Step 4 in Example 50 and then converting the product into its hydrochloride.

Yield: 307 mg (0.665 mmol), 81%
MS (ESI, m/z) 462 (M+H)+
1H-NMR (CDCl3): 1.16 (9H, s), 1.93-2.00 (4H, m), 2.61 (2H, qd), 3.23-3.40 (4H, m), 3.58-3.74 (2H, m), 3.93-4.03 (2H, m), 4.27 (1H, s), 6.88 (1H, dd), 6.95 (2H, s), 7.28-7.40 (8H, m). (free)

Example 65

Synthesis of (R)—N-{2-[4-(5H-dibenzo[a,d][7]annulen-5-ylidene)-1-piperidinyl]-2-oxoethyl}-2-pyrrolidinecarboxamide hydrochloride Step 1

Synthesis of t-butyl 2-[({2-[4-(5H-dibenzo[a,d][7]annulen-5-ylidene)-1-piperidinyl]-2-oxoethyl}amino)carbonyl]-1-pyrrolidinecarboxylate 700 mg (1.91 mmol) of the compound of Example 2, 493 mg (2.29 mmol) of (R)-1-(t-butoxycarbonyl)-2-pyrrolidinecarboxylic acid and 512 mg (2.67 mmol) of 1-ethyl-3-(3'-dimethylaminopropyl)carbodiimide hydrochloride were dissolved in 20 ml of dichloromethane. 0.77 ml (5.59 mmol) of triethylamine and 24 mg (0.2 mmol) of dimethylaminopyridine were added to the obtained solution under cooling with ice, and they were stirred at room temperature overnight. The solvent was evaporated under reduced pressure. Ethyl acetate was added to the residue, and they were washed with water. The organic layer was dried over anhydrous magnesium sulfate. The solvent was evaporated under reduced pressure, and the residue was purified by the silica gel chromatography (hexane:ethyl acetate=9:1 to 1:4) to obtain the title compound.

Yield: 856 mg (1.62 mmol), 85%
MS (ESI, m/z) 528 (M+H)+
1H-NMR (CDCl3): 1.45 (9H, br s), 1.57-1.92 (3H, m), 2.04-2.33 (6H, m), 2.97-3.09 (2H, m), 3.14-3.54 (3H, m), 3.89-4.36 (4H, m), 6.92 (2H, s), 7.15-7.18 (2H, m), 7.24-7.29 (3H, m), 7.32-7.37 (3H, m).

Step 2

Synthesis of (R)—N-{2-[4-(5H-dibenzo[a,d][7]annulen-5-ylidene)-1-piperidinyl]-2-oxoethyl}-2-pyrrolidinecarboxamide hydrochloride 854 mg (1.62 mmol) of the compound obtained in step 1 described above was dissolved in 20 ml of 1,4-dioxane. 2 ml of 4 N hydrochloric acid/1,4-dioxane was added to the obtained solution under cooling with ice, and they were stirred at room temperature for 2.5 hours. The reaction mixture was cooled with ice, 5 ml of 4 N hydrochloric acid/1,4-dioxane was added thereto, and they were stirred at room temperature for 2 hours. 2.5 ml of 4 N hydrochloric acid/1,4-dioxane was added to the reaction mixture under cooling with ice. After stirring at room temperature for 1 hour, 7.5 ml of 4 N hydrochloric acid/1,4-dioxane was added to the reaction mixture, and they were stirred at room temperature for 2 hours. The solvent was concentrated under reduced pressure. Diethyl ether was added to the residue, and crystals thus formed were taken by the filtration to obtain the title compound.

Yield: 747 mg (1.61 mmol) 99%
MS (ESI, m/z) 428 (M+H)+

¹H-NMR (CDCl₃): 2.05 (4H, m), 2.18-2.27 (4H, m), 2.48 (1H, m), 3.04 (2H, m), 3.30-3.52 (3H, m), 3.81-3.95 (2H, m), 4.29 (1H, brd), 4.72 (1H, brd), 6.91 (2H, d), 7.15-7.18 (2H, m), 7.23-7.28 (2H, m), 7.32-7.34 (4H, m), 8.60 (1H, d).

Example 66

Synthesis of (S)—N-{2-[4-(5H-dibenzo[a,d][7]annulen-5-ylidene)-1-piperidinyl]-2-oxoethyl}-2-pyrrolidinecarboxamide hydrochloride The title compound was obtained from (S)-1-(t-butoxycarbonyl)-2-pyrrolidinecarboxylic acid in the same manner as that in Example 65.
MS (ESI, m/z) 428 (M+H)⁺
¹H-NMR (CDCl₃): 1.78-2.32 (8H, m), 2.33-2.51 (1H, m), 2.88-3.15 (2H, m), 3.28-3.55 (3H, m), 3.78-3.98 (2H, m), 4.36 (1H, dt), 4.70 (1H, brd), 6.91 (2H, d), 7.13-7.19 (2H, m), 7.22-7.37 (6H, m), 8.76 (1H, d).

Example 67

Synthesis of (S)-t-butyl 3-[4-(5H-dibenzo[a,d][7]annulen-5-ylidene)-1-piperidinyl]-1-(hydroxymethyl)-3-oxopropylcarbamate The title compound was obtained from (S)-4-(benzyloxy)-2-[(t-butoxycarbonyl)amino]-4-oxobutanoic acid in the same manner as that in Example 60.
MS (ESI, m/z) 475 (M+H)⁺
¹H-NMR (CDCl₃): 1.42 (9H, d), 2.15-2.38 (4H, m), 2.60-2.83 (2H, m), 2.93-3.04 (1H, m), 3.06-3.18 (1H, m), 3.53-3.82 (4H, m), 3.83-4.02 (2H, m), 5.50 (1H, br s), 6.92 (2H, s), 7.14-7.20 (2H, m), 7.23-7.38 (6H, m).

Example 68

Synthesis of (R)-t-butyl 3-[4-(5H-dibenzo[a,d][7]annulen-5-ylidene)-1-piperidinyl]-1-(hydroxymethyl)-3-oxopropylcarbamate The title compound was obtained from (R)-4-(benzyloxy)-2-[(t-butoxycarbonyl)amino]-4-oxobutanoic acid in the same manner as that in Example 60.
MS (ESI, m/z) 475 (M+H)⁺
¹H-NMR (CDCl₃): 1.42 (9H, d), 2.14-2.35 (4H, m), 2.62-2.80 (2H, m), 2.93-3.01 (1H, m), 3.09-3.16 (1H, m), 3.58-3.79 (4H, m), 3.86-3.99 (2H, m), 5.50 (1H, br s), 6.92 (2H, s), 7.14-7.19 (2H, m), 7.23-7.28 (2H, m), 7.31-7.37 (4H, m).

Example 69

Synthesis of (R)—N-[3-[4-(10,11-dihydro-5H-dibenzo[a,d][7]annulen-5-ylidene)-1-piperidinyl]-1-(hydroxymethyl)-3-oxopropyl]-2,2-dimethylpropanamide 745 mg (1.48 mmol) of methyl (R)-2-[(t-butoxycarbonyl)amino]-4-[4-(5H-dibenzo[a,d][7]annulen-5-ylidene)-1-piperidinyl]-4-oxobutanoate was dissolved in 70 ml of ethanol. 1.49 g of palladium carbon (10% w/v) was added to the obtained solution, and they were stirred at room temperature in hydrogen gas atmosphere under 4.4 atm. for 3.5 hours. The catalyst was filtered out, and the filtrate was concentrated under reduced pressure. The intended product was obtained from the resultant residue in the same manner as that in steps 3 and 4 in Example 50.
Yield: 567 mg (1.23 mmol), 83%
MS (ESI, m/z) 461 (M+H)⁺
¹H-NMR (CDCl₃): 1.19 (9H, d), 2.29-2.50 (4H, m), 2.65-2.90 (4H, m), 3.03-3.42 (4H, m), 3.68-3.80 (3H, m), 3.72-4.15 (3H, m), 6.95-6.99 (1H, m), 7.01-7.05 (2H, m), 7.08-7.19 (6H, m).

Example 70

Synthesis of (S)—N-[3-[4-(10,11-dihydro-5H-dibenzo[a,d][7]annulen-5-ylidene)-1-piperidinyl]-1-(hydroxymethyl)-3-oxopropyl]-2,2-dimethylpropanamide The title compound was obtained in the same manner as that in Example 69.
MS (ESI, m/z) 461 (M+H)⁺
¹H-NMR (CDCl₃): 1.19 (9H, d), 2.28-2.51 (4H, m), 2.63-2.90 (4H, m), 3.02-3.44 (4H, m), 3.64-3.83 (3H, m), 3.95-4.17 (3H, m), 6.94-7.07 (3H, m), 7.08-7.20 (6H, m).

Example 71

Synthesis of (S)—N-[4-[4-(5H-dibenzo[a,d][7]annulen-5-ylidene)-1-piperidinyl]-1-(hydroxylmethyl)-4-oxobutyl]-2,2-dimethylpropanamide Step 1

Synthesis of (S)-4-[(t-butoxycarbonyl)amino]-5-methoxy-5-oxopentanoic acid

The title compound was obtained from (S)-5-(benzyloxy)-2-[(t-butoxy-carbonyl)amino]-5-oxopentanoic acid in the same manner as that in Step 1 in Example 50.
Yield: 7.44 g (28.5 mmol), quantitative MS (ESI, m/z) 430 (M−H)⁻
¹H-NMR (CDCl₃): 1.44 (9H, s), 1.90-2.01 (1H, m), 2.15-2.25 (1H, m), 2.38-2.55 (2H, m), 3.75 (3H, s), 4.33-4.40 (1H, m), 5.16 (1H, br d).
Step 2

Synthesis of Methyl (S)-2-[(t-butoxycarbonyl)amino]-5-[4-(5H-dibenzo[a,d][7]-annulen-5-ylidene)-1-piperidinyl]-5-oxopentanoate The title compound was obtained from 5.20 g (17.5 mmol) of the compound obtained in step 1 described above in the same manner as that in step 2 in Example 50.
Yield: 8.35 g (16.2 mmol), 93%
MS (ESI, m/z) 517 (M+H)⁺
¹H-NMR (CDCl₃): 1.42 (9H, s), 1.92-2.04 (1H, m), 2.11-2.43 (7H, m), 2.96-3.11 (2H, m), 3.51 (1H, dt), 3.72 (3H, d), 3.89-3.98 (1H, m), 4.27 (1H, br s), 5.29 (1H, br d), 6.92 (2H, s), 7.14-7.19 (2H, m), 7.23-7.28 (2H, m), 7.30-7.35 (4H, m).
Step 3

Synthesis of methyl(S)-5-[4-(5H-dibenzo[a,d][7]annulen-5-ylidene)-1-piperidinyl]-2-[(2,2-dimethylpropanoyl)amino]-5-oxopentanoate The title compound was obtained from 850 mg (1.65 mmol) of the compound obtained in step 2 described above in the same manner as that in Step 3 in Example 50.
Yield: 840 mg (1.68 mmol), quantitative.
MS (ESI, m/z) 501 (M+H)⁺

¹H-NMR (CDCl₃): 1.18 (9H, d), 2.07-2.49 (8H, m), 2.96-3.12 (2H, m), 3.46-3.55 (1H, m), 3.71 (3H, d), 3.88-3.98 (1H, m), 4.38-4.46 (1H, m), 6.92 (2H, s), 7.06 (1H, br t), 7.16-7.18 (2H, m), 7.23-7.28 (2H, m), 7.32-7.36 (4H, m).

Step 4

Synthesis of (S)—N-[4-[4-(5H-dibenzo[a,d][7]annulen-5-ylidene)-1-piperidinyl]-1-(hydroxylmethyl)-4-oxobutyl]-2,2-dimethylpropanamide 840 mg (1.68 mmol) of the compound obtained in step 3 described above was dissolved in 15 ml of tetrahydrofuran. 0.83 ml of 2 M lithium borohydride/tetrahydrofuran solution was added to the obtained solution at 0° C. in argon atmosphere, and they were stirred at room temperature for 3 hours. Saturated aqueous ammonium chloride solution was added to the reaction mixture under cooling with ice and they were stirred for 10 minutes. The solvent was evaporated under reduced pressure. Ethyl acetate was added to the residue. The resultant mixture was washed with saturated aqueous sodium hydrogencarbonate solution. The organic layer was dried over anhydrous magnesium sulfate, and the solvent was evaporated under reduced pressure. The residue was purified by the silica gel chromatography (dichloromethane:methanol=100:1 to 20:1) to obtain the title compound.

Yield: 717 mg (1.52 mmol), 92%
MS (ESI, m/z) 473 (M+H)⁺
¹H-NMR (CDCl₃): 1.16 (9H, d), 1.87-1.96 (2H, m), 2.13-2.50 (6H, m), 2.98-3.12 (2H, m), 3.50-3.57 (3H, m), 3.76-3.92 (2H, m), 3.97 (1H, dt), 6.83-6.89 (1H, m), 6.92 (2H, s), 7.16-7.18 (2H, m), 7.24-7.28 (2H, m), 7.32-7.36 (4H, m).

Example 72

Synthesis of (R)—N-[4-[4-(5H-dibenzo[a,d][7]annulen-5-ylidene)-1-piperidinyl]-1-(hydroxylmethyl)-4-oxobutyl]-2,2-dimethylpropanamide The title compound was obtained from (R)-5-(benzyloxy)-2-[(t-butoxy-carbonyl)amino]-5-oxopentanoic acid in the same manner as that of Example 71.
MS (ESI, m/z) 473 (M+H)⁺
¹H-NMR (CDCl₃): 1.16 (9H, d), 1.88-1.96 (2H, m), 2.14-2.50 (6H, m), 2.98-3.12 (2H, m), 3.50-3.57 (3H, m), 3.81 (2H, br s), 3.96 (1H, dt), 6.84-6.90 (1H, m), 6.92 (2H, s), 7.15-7.19 (2H, m), 7.23-7.29 (2H, m), 7.31-7.36 (4H, m).

Example 73

Synthesis of (R)-ethyl 3-[4-(5H-dibenzo[a,d][7]annulen-5-ylidene)-1-piperidinyl]-1-(hydroxymethyl)-3-oxopropylcarbamate Step 1

Synthesis of methyl(R)-4-[4-[(5H-dibenzo[a,d][7]annulen-5-ylidene)-1-piperidinyl]-2-[(ethoxycarbonyl)amino]-4-oxobutanoate 2.13 mg (4.23 mmol) of methyl (R)-2-[(t-butoxycarbonyl)amino]-4-[4-(5H-dibenzo[a,d][7]annulen-5-ylidene)-1-piperidinyl]-4-oxobutanoate was dissolved in 30 ml of ethyl acetate. 30 ml of 4 N hydrochloric acid/ethyl acetate was added to the obtained solution under cooling with ice for the duration of 10 minutes, and they were stirred at room temperature for 6 hours. The solvent was evaporated under reduced pressure, and the residue was dissolved in 43 ml of dichloromethane. 0.94 ml (6.36 mmol) of diethyl pyrocarbonate and 1.19 ml (8.54 mmol) of triethylamine were added to the obtained solution under cooling with ice. The resultant mixture was stirred at room temperature for 2 hours. Aqueous ammonium chloride solution was added to the reaction mixture under cooling with ice. After extracting with dichloromethane, the organic layer was dried over anhydrous sodium sulfate. The solvent was evaporated under reduced pressure, and the residue was purified by the silica gel chromatography (hexane:ethyl acetate=3:1 to 1:1) to obtain the title compound.

Yield: 1.83 g (3.85 mmol) (91%)
MS (ESI, m/z) 475 (M+H)⁺
¹H-NMR (CDCl₃): 1.24 (3H, dt), 2.13-2.34 (4H, m), 2.75 (1H, td), 2.91-3.17 (3H, m), 3.45-3.54 (1H, m), 3.74 (3H, d), 3.89 (1H, dt), 4.06-4.13 (2H, m), 4.56-4.62 (1H, m), 5.92 (1H, br t), 6.92 (2H, s), 7.15-7.18 (2H, m), 7.23-7.28 (2H, m), 7.31-7.36 (4H, m).

Step 2

Synthesis of (R)-ethyl 3-[4-(5H-dibenzo[a,d][7]annulen-5-ylidene)-1-piperidinyl]-1-(hydroxymethyl)-3-oxopropylcarbamate The title compound was obtained from 1.82 g (3.84 mmol) of the compound obtained in step 1 described above in the same manner as that in Step 4 in Example 71.

Yield: 1.54 g (3.46 mmol), 90%
MS (ESI, m/z) 447 (M+H)⁺
¹H-NMR (CDCl₃): 1.19-1.28 (3H, m), 2.14-2.30 (4H, m), 2.70-2.75 (2H, m), 2.93-3.04 (1H, m), 3.07-3.16 (1H, m), 3.45 (1H, br s), 3.58-3.64 (1H, m), 3.69-3.79 (2H, m), 3.90-3.98 (2H, m), 4.04-4.13 (2H, m), 5.64 (1H, br s), 6.92 (2H, s), 7.14-7.19 (2H, m), 7.23-7.37 (6H, m).

Example 74

Synthesis of (S)-t-butyl 4-[(5H-dibenzo[a,d][7]annulen-5-ylidene)-1-piperidinyl]-1-(hydroxymethyl)-4-oxobutylcarbamate The title compound was obtained from 890 mg (1.72 mmol) of the compound obtained in step 2 in Example 71 in the same manner as that in Step 4 in Example 71.

Yield: 776 mg (1.59 mmol), 92%
MS (ESI, m/z) 489 (M+H)⁺
¹H-NMR (CDCl₃): 1.42 (9H, d), 1.73-1.86 (1H, m), 1.92-2.00 (1H, m), 2.13-2.47 (6H, m), 2.93-3.13 (2H, m), 3.29 (1H, br s), 3.51-3.56 (4H, m), 3.89-4.00 (1H, m), 5.09 (1H, br s), 6.92 (2H, s), 7.15-7.19 (2H, m), 7.23-7.28 (2H, m), 7.31-7.37 (4H, m).

Example 75

Synthesis of (R)-t-butyl 4-[(5H-dibenzo[a,d][7]annulen-5-ylidene)-1-piperidinyl]-1-(hydroxymethyl)-4-oxobutylcarbamate The title compound was obtained in the same manner as that in Example 74.
MS (ESI, m/z) 489 (M+H)⁺
¹H-NMR (CDCl₃): 1.43 (9H, d), 1.73-1.89 (1H, m), 1.90-2.01 (1H, m), 2.14-2.48 (6H, m), 2.93-3.13 (2H, m), 3.27 (1H, br s), 3.49-3.59 (4H, m), 3.89-4.01 (1H, m), 5.09 (1H, br s), 6.92 (2H, s), 7.14-7.19 (2H, m), 7.23-7.28 (2H, m), 7.31-7.36 (4H, m).

Example 76

Synthesis of tert-butyl (1R)-1-(hydroxymethyl)-3-oxo-3-[4-(9H-thioxanthen-9-ylidene)-1-piperidinyl]propylcarbamate:

Step 1

Synthesis of methyl (2R)-2-[(t-butoxycarbonyl)amino]-4-oxo-4-[4-(9H-thioxanthen-9-ylidene)-1-piperidinyl]butanoate 1.00 g (5.22 mmol) of 1-ethyl-3-(3'-dimethylaminopropyl)carbodiimide hydrochloride, 0.73 ml (5.24 mmol) of triethylamine and 1.351 g (4.84 mmol) of 4-(9H-thioxanthen-9-ylidene)piperidine were added to 1.290 g (5.22 mmol) of (S)-3-[(t-butoxycarbonyl)amino]-4-methoxy-4-oxobutanoic acid in 20 ml of dichloromethane in an ice bath, and they were stirred at room temperature overnight. Saturated aqueous ammonium chloride solution was added to the reaction mixture. After extracting with dichloromethane, the organic layer was dried over anhydrous sodium sulfate, and the solvent was evaporated under reduced pressure. The residue was purified by the silica gel chromatography (hexane:ethyl acetate=7:3 to 1:1) to obtain the title compound.

Yield: 1.645 g (3.23 mmol), 67%
MS (ESI, m/z) 509 (M+H)$^+$
$^1$H-NMR (CDCl$_3$): 1.45 (9H, d), 2.48-3.24 (8H, m), 3.58-4.20 (5H, m), 4.52-4.66 (1H, m), 5.80 (1H, t), 7.17-7.32 (6H, m), 7.51 (2H, d).

Step 2

Synthesis of tert-butyl (1R)-1-(hydroxymethyl)-3-oxo-3-[4-(9H-thioxanthen-9-ylidene)-1-piperidinyl]propylcarbamate The title compound was obtained from 714 mg (1.40 mmol) of the compound obtained in Step 1 described above in the same manner as that in Step 4 in Example 71.

Yield: 554 mg (1.15 mmol), 82%
MS (ESI, m/z) 481 (M+H)$^+$
$^1$H-NMR (CDCl$_3$): 1.44 (9H, d), 2.49-3.22 (8H, m), 3.48-3.98 (5H, m), 4.15-4.26 (1H, m), 5.52 (1H, m), 7.17-7.31 (6H, m), 7.51 (2H, d).

Example 77

Synthesis of N-{(1R)-1-(hydroxymethyl)-3-oxo-3-[4-(9H-thioxanthen-9-ylidene)-1-piperidinyl]propyl}-2,2-dimethylpropanamide Step 1

Synthesis of Methyl (2R)-2-[(2,2-dimethylpropanoyl)amino]-4-oxo-4-[4-(9H-thioxanthen-9-ylidene)-1-piperidinyl]butanoate The title compound was obtained from 821 mg (1.61 mmol) of the compound obtained in Step 1 in Example 76 in the same manner as that in Step 3 in Example 50.

MS (ESI, m/z) 493 (M+H)$^+$
$^1$H-NMR (CDCl$_3$): 1.22 (9H, d), 2.46-3.26 (8H, m), 3.58-4.20 (5H, m), 4.81-4.96 (1H, m), 7.04-7.10 (1H, m), 7.17-7.32 (6H, m), 7.51 (2H, d).

Step 2

Synthesis of N-{(1R)-1-(hydroxymethyl)-3-oxo-3-[4-(9H-thioxanthen-9-ylidene)-1-piperidinyl]propyl}-2,2-dimethylpropanamide The title compound was obtained from the whole amount of the compound obtained in Step 1 described above in the same manner as that in Step 4 in Example 71.

Yield: 574 mg (1.24 mmol), 77% (2 steps)
MS (ESI, m/z) 465 (M+H)$^+$
$^1$H-NMR (CDCl$_3$): 1.20 (9H, d), 2.47-3.25 (8H, m), 3.62-4.27 (6H, m), 6.91-7.02 (1H, m), 7.17-7.31 (6H, m), 7.51 (2H, d).

Example 78

Synthesis of (S)—N-[4-[4-(10, 11)-dihydro-5H-dibenzo[a,d][7]annulen-5-ylidene]-1-piperidinyl]-1-(hydroxymethyl)-4-oxobutyl]-2,2-dimethylpropanamide 1.91 g (4.04 mmol) of the compound obtained in Example 71 was dissolved in 100 ml of ethanol. 2.5 g of palladium carbon (10% w/v) was added to the obtained solution, and they were stirred at room temperature in hydrogen gas atmosphere under a pressure of 5 atm. for 3.5 hours. The catalyst was filtered out, and the filtrate was concentrated under reduced pressure. The residue was purified by the silica gel chromatography (dichloromethane:methanol=60:1 to 20:1) to obtain the title compound.

Yield: 1.77 g (3.73 mmol), 92%
MS (ESI, m/z) 475 (M+H)$^+$
$^1$H-NMR (CDCl$_3$): 1.18 (9H, d), 1.90-1.99 (2H, m), 2.27-2.48 (6H, m), 2.78-2.90 (2H, m), 3.10-3.25 (2H, m), 3.32-3.42 (2H, m), 3.53-3.64 (3H, m), 3.74-3.88 (2H, m), 4.06 (1H, dt), 6.89 (1H, dd), 7.02-7.04 (2H, m), 7.09-7.17 (6H, m).

Example 79

Synthesis of N-[(1S)-2-[4-(5H-dibenzo[a,d][7]annulen-5-ylidene)-1-piperidinyl]-1-(hydroxymethyl)-2-oxoethyl]-2,2-dimethylpropanamide Step 1

Synthesis of pivaloyl-L-serine 5.25 g (50.0 mmol) of L-serine was dissolved in 1 N aqueous sodium hydroxide solution. 50 ml of 1 N aqueous sodium hydroxide solution and a solution of 5 ml (40.6 mmol) of pivaloyl chloride in 12 ml of diethyl ether were simultaneously added dropwise to the obtained solution in ice bath. After stirring for 2.5 hours, 70 ml of 1 N hydrochloric acid was added to the reaction mixture to make it acidic. After extracting with ethyl acetate, the organic layer was dried over anhydrous sodium sulfate, and the solvent was evaporated under reduced pressure to obtain the title compound.

Yield: 3.95 g (20.9 mmol), 52%
$^1$H-NMR (DMSO): 1.12 (9H, s), 3.61-3.75 (2H, m), 4.19-4.26 (1H, m).

Step 2

Synthesis of N-[(1S)-2-[4-(5H-dibenzo[a,d][7]annulen-5-ylidene)-1-piperidinyl]-1-(hydroxymethyl)-2-oxoethyl]-2,2-dimethylpropanamide 880 mg (4.59 mmol) of 1-ethyl-3-(3'-dimethylaminopropyl)carbodiimide hydrochloride, 0.63 ml (4.52 mmol) of triethylamine and 860 mg (4.55 mmol) of pivaloyl-L-serine were added to 1.231 g (4.50 mmol) of 4-(5H-dibenzo[a,d][7]annulen-5-ylidene)piperidine in 20 ml of dichloromethane in ice bath, and they were stirred at room temperature overnight. 1 N hydrochloric acid was added to the reaction mixture. After extracting with dichloromethane, the organic layer was dried over anhydrous sodium sulfate. The solvent was evaporated under reduced pressure. The residue was purified by the silica gel chromatography (hexane:ethyl acetate=7:3 to 1:2) to obtain the title compound.

Yield: 1.032 g (2.32 mmol), 52%

MS (ESI, m/z) 445 (M+H)$^+$ $^1$H-NMR (CDCl$_3$): 1.22 (9H, d), 2.14-2.44 (4H, m), 2.90-3.27 (2H, m), 3.61-4.06 (5H, m), 4.80-4.89 (1H, m), 6.92 (2H, s), 7.01-7.38 (8H, m).

Example 80

Synthesis of N—[(1R)-2-[4-(5H-dibenzo[a,d][7]annulen-5-ylidene)-1-piperidinyl]-1-(hydroxymethyl)-2-oxoethyl]-2,2-dimethylpropanamide The title compound was obtained from D-serine in the same manner as that in Example 79.

MS (ESI, m/z) 445 (M+H)$^+$ $^1$H-NMR (CDCl$_3$): 1.22 (9H, d), 2.16-2.44 (4H, m), 2.90-3.26 (2H, m), 3.62-4.06 (5H, m), 4.79-4.89 (1H, m), 6.92 (2H, s), 7.01-7.38 (8H, m).

Example 81

Synthesis of N-{(1S)-1-(hydroxymethyl)-4-oxo-4-[4-(9H-thioxanthen-9-ylidene)-1-piperidinyl]butyl}-2,2-dimethylpropanamide Step 1

Synthesis of methyl (2S)-2-[(t-butoxycarbonyl)amino]-5-oxo-5-[4-(9H-thioxanthen-9-ylidene)-1-piperidinyl]pentanoate The title compound was obtained from 511 mg (1.96 mmol) of the compound obtained in Step 1 in Example 71 and 470 mg (1.68 mmol) of 4-(9H-thioxanthen-9-ylidene)piperidine in the same manner as that in Step 2 in Example 50.

Yield: 742 mg (1.42 mmol), 85%

MS (ESI, m/z) 523 (M+H)$^+$ $^1$H-NMR (CDCl$_3$): 1.44 (9H, d), 1.91-2.79 (8H, m), 2.88-3.18 (2H, m), 3.62-3.74 (1H, m), 3.75 (3H, d), 4.12-4.38 (2H, m), 5.26-5.37 (1H, m), 7.17-7.53 (8H, m).

Step 2

Synthesis of Methyl (2S)-2-[(2,2-dimethylpropanoyl)amino]-5-oxo-5-[4-(9H-thioxanthen-9-ylidene)-1-piperidinyl]pentanoate:

The title compound was obtained from 736 mg (1.41 mmol) of the compound obtained in Step 1 described above in the same manner as that in Step 3 in Example 50.

$^1$H-NMR (CDCl$_3$): 1.20 (9H, d), 2.04-2.80 (8H, m), 2.88-3.18 (2H, m), 3.60-3.78 (4H, m), 4.11-4.26 (1H, m), 4.41-4.52 (1H, m), 7.04 (1H, t), 7.17-7.33 (6H, m), 7.51 (2H, d).

Step 3

Synthesis of N-{(1S)-1-(hydroxymethyl)-4-oxo-4-[4-(9H-thioxanthen-9-ylidene)-1-piperidinyl]butyl}-2,2-dimethylpropanamide The title compound was obtained from the whole amount of the compound obtained in Step 2 described above in the same manner as that in Step 4 in Example 71.

Yield: 564 mg (1.18 mmol), 84% (step 2)

MS (ESI, m/z) 479 (M+H)$^+$ $^1$H-NMR (CDCl$_3$): 1.18 (9H, d), 1.86-2.02 (2H, m), 2.28-2.82 (6H, m), 2.92-3.18 (2H, m), 3.48-3.88 (5H, m), 4.14-4.26 (1H, m), 6.79-6.92 (1H, m), 7.17-7.31 (6H, m), 7.51 (2H, d).

Example 82

Synthesis of (S)-tert-butyl 1-{[4-(5H-dibenzo[a,d][7]annulen-5-ylidene)-1-piperidinyl]carbonyl}-3-hydroxypropylcarbamate Step 1

Synthesis of benzyl(S)-3-[(tert-butoxycarbonyl)amino]-4-[4-(5H-dibenzo-[a,d][7]-annulen-5-ylidene)-1-piperidinyl]-4-oxobutanoate 10 ml of methylene chloride, 306 mg (1.60 mmol) of 1-ethyl-3-(3'-dimethylaminopropyl)carbodiimide hydrochloride, 421 mg (1.54 mmol) of 4-(5H-dibenzo[a,d][7]annulen-5-ylidene)-1-piperidine, 212 mg (1.57 mmol) of 1-hydroxybenzotriazole and 0.23 ml (1.65 mmol) of triethylamine were added to 498 mg (1.54 mmol) of (S)-4-(benzyloxy)-2-[(t-butoxycarbonyl)amino]-4-oxobutanoic acid, and they were stirred at room temperature overnight. Saturated aqueous ammonium chloride solution was added to the reaction mixture. After extracting with methylene chloride, the organic layer was dried over anhydrous sodium sulfate, and the solvent was evaporated under reduced pressure. The residue was purified by the silica gel chromatography (hexane:ethyl acetate=7:3) to obtain the title compound.

Yield: 839 mg (1.45 mmol), 94%

$^1$H-NMR (CDCl$_3$): 1.50 (9H, d), 2.08-2.38 (4H, m), 2.54-3.28 (4H, m), 3.62-4.04 (2H, m), 4.92-5.03 (1H, m), 5.10 (2H, d), 7.13-7.39 (8H, m)

Step 2

Synthesis of (S)-tert-butyl 1-{[4-(5H-dibenzo[a,d][7]annulen-5-ylidene)-1-piperidinyl]carbonyl}-3-hydroxypropylcarbamate 797 mg (1.38 mmol) of benzyl (S)-3-[(tert-butoxycarbonyl)amino]-4-[4-(5H-dibenzo[a,d][7]annulen-5-ylidene)-1-piperidinyl]-4-oxobutanoate was dissolved in 15 ml of tetrahydrofuran. 1.45 ml of 2 M lithium borohydride/tetrahydrofuran solution was added to the obtained solution in argon atmosphere at 0° C., and they were stirred at room temperature overnight. Saturated aqueous ammonium chloride solution was added to the reaction mixture under cooling with ice. After extracting with ethyl acetate, the organic layer was dried over anhydrous sodium sulfate and then the solvent was evaporated under reduced pressure. The residue was purified by the silica gel chromatography (hexane:ethyl acetate=3:1 to 1:1) to obtain the title compound.

Yield: 180 mg (1.45 mmol), 28%

MS (ESI, m/z) 475 (M+H)$^+$

¹H-NMR (CDCl₃): 1.44 (9H, d), 1.20-1.99 (2H, m), 2.94-3.22 (2H, m), 3.54-4.03 (4H, m), 4.67-4.78 (1H, m), 5.77 (1H, d), 6.92 (2H, d), 7.18-7.38 (8H, m)

Example 83

Synthesis of (S)—N-[4-[4-(5H-dibenzo[a,d][7]annulen-5-ylidene)-1-piperidinyl]-1-(hydroxymethyl)-4-oxobutyl]acetamide Step 1

Synthesis of (S)-2-amino-5-[4-(5H-dibenzo[a,d][7]annulen-5-ylidene)-1-piperidinyl]-5-oxo-1-pentanol hydrochloride (S)-t-butyl 4-[(5H-dibenzo[a,d][7]annulen-5-ylidene)-1-piperidinyl]-1-(hydroxymethyl)-4-oxobutylcarbamate was dissolved in 5 ml of ethyl acetate. 10 ml of 4 N hydrochloric acid/ethyl acetate was added to the solution in ice bath, and they were stirred for 6.5 hours. The reaction solution was concentrated under reduced pressure to obtain the title compound.
Yield: 607 mg (1.43 mmol), 100%

Step 2

Synthesis of (S)—N-[4-[4-(5H-dibenzo[a,d][7]annulen-5-ylidene)-1-piperidinyl]-1-(hydroxymethyl)-4-oxobutyl]acetamide 2 ml of 1 N aqueous sodium hydroxide solution, 3 ml of diethyl ether and 2 ml of ethyl acetate were added to 151 mg (0.36 mmol) of (S)-2-amino-5-[4-(5H-dibenzo[a,d][7]annulen-5-ylidene)-1-piperidinyl]-5-oxo-1-pentanol hydrochloride. 0.04 ml (0.56 mmol) of acetyl chloride was added dropwise to the obtained solution under vigorous stirring, and they were stirred at room temperature for 2 hours. Water was added to the reaction mixture. After extracting with ethyl acetate, the organic layer was dried over anhydrous sodium sulfate and then concentrated under reduced pressure. The residue was purified by the silica gel chromatography (chloroform:methanol-200:1 to 50:1) to obtain the title compound.
Yield: 114 mg (0.27 mmol), 75%
MS (ESI, m/z) 431 (M+H)⁺
¹H-NMR (CDCl₃): 1.70-1.97 (2H, m), 1.96 (3H, s), 2.12-2.31 (4H, m), 2.34-2.43 (2H, m), 2.95-3.13 (2H, m), 3.48-3.59 (3H, m), 3.74-4.01 (3H, m), 6.67 (1H, t), 6.92 (2H, d), 7.15-7.37 (8H, m)

Example 84

Synthesis of (S)—N-[4-[4-(5H-dibenzo[a,d][7]annulen-5-ylidene)-1-piperidinyl]-1-(hydroxymethyl)-4-oxobutyl]-2-methylpropanamide The title compound was obtained by using isobutyryl chloride in the same manner as that in Step 2 in Example 83.
Yield: 108 mg (0.23 mmol), 72%
MS (ESI, m/z) 459 (M+H)⁺
¹H-NMR (CDCl₃): 1.07-1.20 (6H, m), 1.93 (2H, qua), 2.12-2.48 (7H, m), 2.94-3.13 (2H, m), 3.48-3.62 (3H, m), 3.76-4.02 (2H, m), 6.65-6.76 (1H, m), 6.92 (2H, m), 7.14-7.38 (8H, m)

Example 85

Synthesis of (S)—N-[4-[4-(5H-dibenzo[a,d][7]annulen-5-ylidene)-1-piperidinyl]-1-(hydroxymethyl)-4-oxobutyl]cyclohexanecarboxamide The title compound was obtained by using cyclohexanoyl chloride in the same manner as that in Step 2 in Example 83.
Yield: 87 mg (0.17 mmol), 68%.
MS (ESI, m/z) 499 (M+H)⁺
¹H-NMR (CDCl₃): 1.12-1.51 (6H, m), 1.58-2.48 (13H, m), 2.95-3.12 (2H, m), 3.46-3.60 (3H, m), 3.75-4.02 (3H, m), 6.55-6.65 (1H, m), 6.92 (2H, m), 7.14-7.38 (8H, m)

Example 86

Synthesis of (S)—N-[4-[4-(5H-dibenzo[a,d][7]annulen-5-ylidene)-1-piperidinyl]-1-(hydroxymethyl)-4-oxobutyl]-2-benzamide The title compound was obtained by using benzoyl chloride in the same manner as that in Step 2 in Example 83.
Yield: 95 mg (0.19 mmol), 75%.
MS (ESI, m/z) 493 (M+H)⁺
¹H-NMR (CDCl₃): 1.94-2.32 (6H, m), 2.35-2.58 (2H, m), 2.90-3.11 (2H, m), 3.47-3.59 (1H, m), 3.88-4.13 (2H, m), 6.90 (2H, d), 7.06-7.67 (12H, m), 7.78-7.89 (2H, m)

The structural formulae of the compounds obtained in Examples 1 to 86 are shown in Tables 1 to 11.

TABLE 1

| Ex. | Structural formula |
|---|---|
| 1 | |
| 2 | |
| 3 | |

TABLE 1-continued

| Ex. | Structural formula |
|---|---|
| 4 | |
| 5 | |
| 6 | |
| 8 | |
| 9 | |

TABLE 2

| Ex. | Structural formula |
|---|---|
| 10 | ClH |
| 11 | |
| 12 | |
| 13 | |
| 14 | ClH |

TABLE 2-continued

| Ex. | Structural formula |
|---|---|
| 15 | |
| 16 | |
| 17 | |

TABLE 3

| Ex. | Structural formula |
|---|---|
| 18 | |
| 19 | |

TABLE 3-continued

| Ex. | Structural formula |
|---|---|
| 20 | |
| 21 | |
| 22 | |
| 23 | |
| 24 | |

TABLE 3-continued

| Ex. | Structural formula |
|---|---|
| 25 | |

TABLE 4

| Ex. | Structural formula |
|---|---|
| 26 | |
| 27 | |
| 28 | |
| 29 | |

TABLE 4-continued

| Ex. | Structural formula |
|---|---|
| 30 | |
| 31 | |
| 32 | |
| 33 | |

TABLE 5

| Ex. | Structural formula |
|---|---|
| 34 | ClH |

TABLE 5-continued
| Ex. | Structural formula |
|---|---|
| 35 | 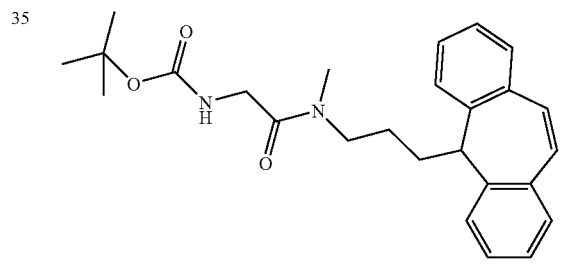 |
| 36 | 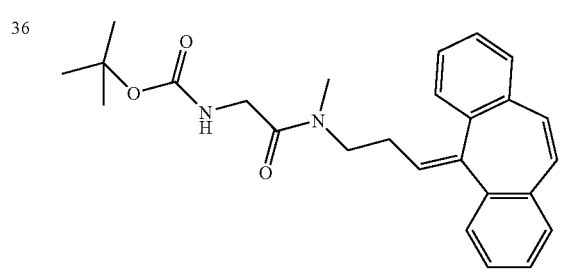 |
| 37 | 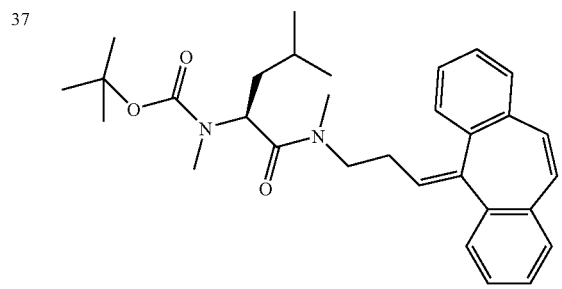 |
| 38 | 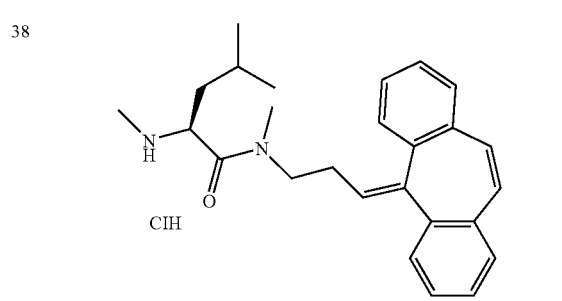 |
| 39 | 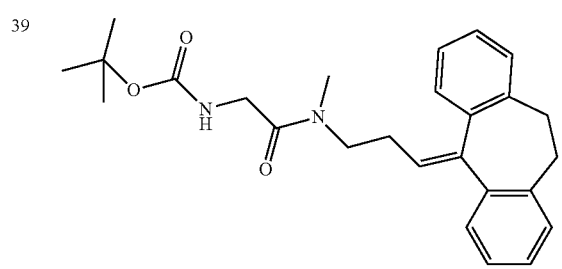 |
TABLE 5-continued
| Ex. | Structural formula |
|---|---|
| 40 | 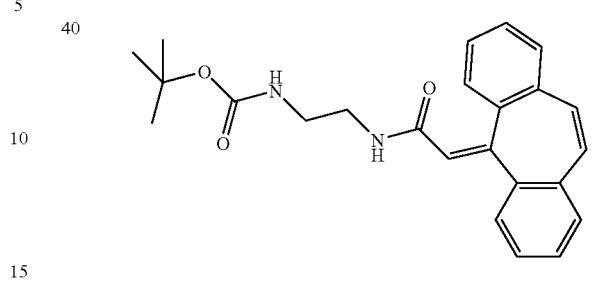 |
| 41 | 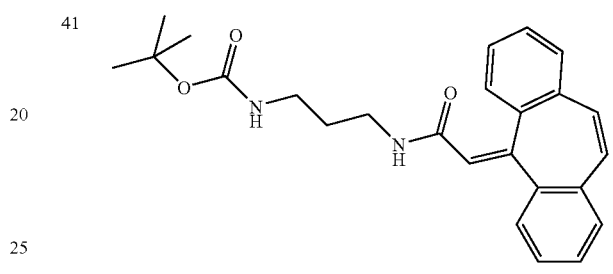 |
TABLE 6
| Ex. | Structural formula |
|---|---|
| 42 | 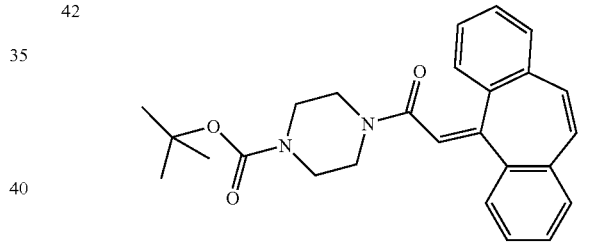 |
| 43 | 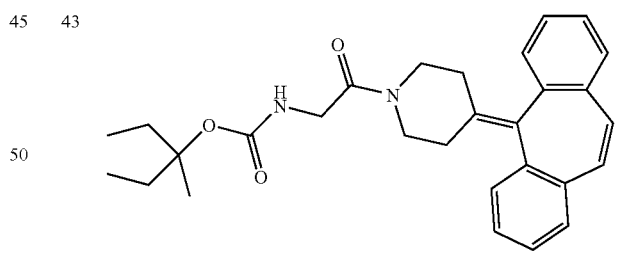 |
| 44 | 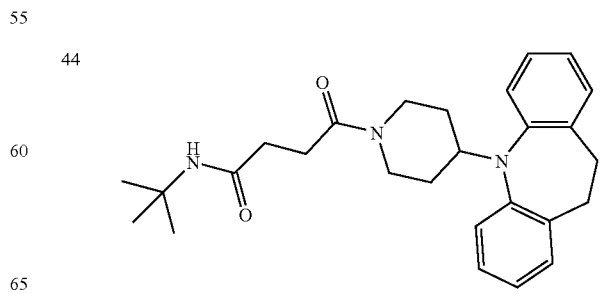 |

TABLE 6-continued

| Ex. | Structural formula |
|---|---|
| 45 | |
| 46 | |
| 47 | |
| 48 | |
| 49 | |

TABLE 7

| Ex. | Structural formula |
|---|---|
| 50 | |
| 51 | |
| 52 | |
| 53 | |
| 54 | |
| 55 | |

TABLE 7-continued

| Ex. | Structural formula |
|---|---|
| 56 | (structure) |
| 57 | (structure) |

TABLE 8

| Ex. | Structural formula |
|---|---|
| 58 | (structure) (S) |
| 59 | (structure) (R) |
| 60 | (structure) |

TABLE 8-continued

| Ex. | Structural formula |
|---|---|
| 61 | (structure) |
| 62 | (structure) (S) ClH |
| 63 | (structure) (R) ClH |
| 64 | (structure) ClH |
| 65 | (structure) (R) ClH |

TABLE 9

| Ex. | Structural formula |
|---|---|
| 66 | (S) |
| 67 | (S) |
| 68 | (R) |
| 69 | (R) |
| 70 | (S) |

TABLE 9-continued

| Ex. | Structural formula |
|---|---|
| 71 | (S) |
| 72 | (R) |
| 73 | (R) |

TABLE 10

| Ex. | Structural formula |
|---|---|
| 74 | (S) |
| 75 | (R) |

TABLE 10-continued

| Ex. | Structural formula |
|---|---|
| 76 | (R) |
| 77 | (R) |
| 78 | (S) |
| 79 | (S) |
| 80 | (R) |
| 81 | (S) |

TABLE 11

| Ex. | Structural formula |
|---|---|
| 82 | (S) |
| 83 | (S) |
| 84 | (S) |
| 85 | (S) |
| 86 | (S) |

Test Example 1

Antagonistic Activity on N-Type Calcium Channel (Fluorescence Dye Method)

Human neuroblastoma cells IMR-32 were obtained from ATCC (American Type Culture Collection). The medium used was a Phenol Red-free Eagle minimum essential medium containing earle's salts (GIBCO) supplemented with 2 mM of L-glutamine (GIBCO), 1 mM of sodium pyruvate (pH 6.5) (GIBCO), antibiotic/antimycotic mixture (GIBCO) and 10% fetal calf serum (Cell Culture Technologies). Three ml of $1\times10^5$ cells/ml IMR-32 cells were spread on the glass bottom of a dish (Iwaki Glass Co., Ltd.) having a diameter of 35 mm which had been treated with poly-L-lysin (SIGMA) and collagen (COLLAGEN VITROGEN 100; Collagen Co.). After the culture for 1 day, 1 mM (final concentration) of dibutyl cAMP and 2.5 μM (final concentration) of 5-bromodeoxyuridine (SIGMA) were added. After the culture for additional 10 to 14 days, the cells were subjected to the activity determination.

The medium for IMR-32 cells thus prepared was replaced with 1 ml of Phenol Red-free Eale minimum essential medium (GIBCO) containing 2.5 μM fura-2/AM (Dojin Kagaku, Co.) and earle's salts supplement, and the incubation was conducted at 37° C. for 30 minutes. Then the medium was replaced with a recording medium (20 mM of HEPES-KOH, 115 mM of NaCl, 5.4 mM of KCl, 0.8 mM of $MgCl_2$, 1.8 mM of $CaCl_2$ and 13.8 mM of D-glucose). Antagonistic activity on N-type calcium channel was determined and analyzed using a fluorescence microscope (Nikon Corporation) and an image analysis device ARGUS 50 (Hamamatsu Photonics). In particular, a recording medium (20 mM of HEPES-KOH, 115 mM of NaCl, 5.4 mM of KCl, 0.8 mM of $MgCl_2$, 1.8 mM of $CaCl_2$ and 13.8 mM of D-glucose) containing 1 μM of Nifedipine was given to the cells by reflux by a Y-tube method for 2 minutes. Then a stimulating agent containing 60 mM of potassium chloride was rapidly given by the Y-tube method. The calcium concentration change in the cells in this step was shown as the N-type calcium channel activity. Then stimulating agents containing 60 mM of potassium chloride and 0.1, 1 or 10 μM of the test compound were successively and rapidly given to the cells by the Y-tube method to determine the change in the intracellular calcium concentration. The antagonistic activity on N-type calcium channel was calculated from the inhibition rate (%) at a concentration of 10 μM.

Test Example 2

Antagonistic Activity on L-Type Calcium Channel

The antagonistic activity of the new diarylalkene derivatives and diarylalkane derivatives of the present invention to inhibit L-type calcium channel was determined by the following method in which the relaxation response against the KCl-induced contraction of isolated rat thoracic aorta was employed.

1) Method of Preparation of Rat Thoracic Aorta:

The slips of thoracic aorta isolated from a Wistar rat were used. The aorta was cut to obtain ring-shaped samples having a width of about 3 mm. The endothelial cells of the samples were mechanically removed. The samples were suspended in a strain gage in Tyrode's solution (158.3 mM of NaCl, 4.0 mM of KCl, 1.05 mM of $MgCl_2$, 0.42 mM of $NaH_2PO_4$, 10 mM of $NaHCO_3$, 2 mM of $CaCl_2$ and 5 mM of glucose) in which a gaseous mixture of $O_2$ (95%) and $CO_2$ (5%) was introduced. A static tension of 2 g was applied thereto. The tension of the blood vessel was amplified with a transducer and a tension amplifier (EF-601G; Nihon Koden Corporation) and recorded with a multi-pen recorder (Rikadenki Kogyo Co., Ltd.). The experiments were conducted at 37° C.

2) Measurement of Relaxation Response Against KCl-Induced Contraction:

After the tension had been stabilized, the nutrient solution in the sample tank was replaced with High $K^+$ Tyrode's solution (112.3 mM of NaCl, 50 mM of KCl, 1.05 mM of $MgCl_2$, 0.42 mM of $NaH_2PO_4$, 10 mM of $NaHCO_3$, 2 mM of $CaCl_2$ and 5 mM of glucose) to conduct the contraction reaction. Thirty minutes after, the solution in the sample tank was replaced with the normal Tyrode's solution. The solution in the sample tank was again replaced with the High $K^+$ Tyrode's solution and the contraction reaction was observed. After attaining the maximum contraction reaction, the test compound was cumulatively added at intervals of 90 minutes to attain concentrations of $10^{-9}$, $10^{-8}$, $10^{-7}$ and $10^{-6}$ M. The inhibitory rate of the test compound against the maximum contraction response was employed as the index of the antagonistic activity on L-type calcium channels.

Table 12 shows the results of the measurement of the antagonistic activities on N-type calcium channels (inhibition rate at 10 μM: %) and L-type calcium channel ($pIC_{50}$). The value of $pIC_{50}$ indicates the antagonistic activity of the test compound, i.e. the negative logarithm of the concentration of the test compound necessitated for the 50% inhibition.

TABLE 12

| Example | Antagonistic activity on N-type calcium channels at 10 μM inhibition rate (%) | Antagonistic action on L-type calcium channels $pIC_{50}$ |
|---|---|---|
| 1  | 67 | 6.0 |
| 9  | 83 | 6.3 |
| 11 | 77 | 6.4 |
| 16 | 75 | 5.9 |
| 24 | 78 | 6.0 |
| 41 | 76 | 5.9 |
| 68 | 82 | 6.4 |
| 71 | 74 | 5.9 |
| 72 | 81 | 6.1 |
| 73 | 75 | 5.7 |
| 76 | 85 | 6.1 |
| 78 | 84 | 5.6 |

Test Example 3

Analgesic Effects in the Formalin Test

<Method>

Four test groups each composed of 7 male Sprague-Dawley SD rats (9 weeks old) were used for the experiment. In the control group, 0.5% tragacanth solution was given to the rats. In other test groups, 0.3, 3 or 30 mg/kg of the compound obtained in Example 11 (compound A) was given to them. Compound A was used in the form of a suspension thereof in 0.5% tragacanth solution.

Five ml/kg of 0.5% tragacanth solution or compound A was orally administered to the rats. Three hours after, the rats were tranquilized with halothane, and 2.5% formalin solution (100 μl) was injected subcutaneously to dorsal surface of the left hindpaw. Immediately thereafter, the rats were awaken from the anesthesia. The action of the rats were observed for 60 minutes. The number of times of retracting action, i.e., flinching action of the hindpaw in which formalin had been injected, was counted for 1 minute at an interval of one minute until 5 minutes after the formalin injection, and for 1 minute at an interval of 5 minutes from 10 to 60 minutes after the injection. As reported in a literature (J. Pharmacol. Exp. Ther. 263: 136-146, 1992), the pain reaction by the stimulation with formalin appeared in two phases. The total number of times of the flinching action observed 10 to 60 minutes after the formalin injection (the second phase) was taken as the index of the pain action.
<Results>
FIG. 1 is a graph showing the average measurement standard error in each experiment group. The inhibiting ratios of flinches in the groups of 0.3, 3 and 30 mg/kg of compound A were 10, 42 and 37%, respectively, based on the average number of the flinches in the control group. Thus, a remarkable analgesic effect was confirmed.

Test Example 4

Analgesic Effects on a Neuropathic Pain Model

<Method>
The effect of compound A in improving mechanical allodynia was evaluated using the partial sciatic nerve ligation model (Seltzer model, Pain, 43: 205-218, 1990) which belongs to the neuropathic pain models. For detecting the mechanical allodynia, the sole of the right paw of each rat was stimulated with von Frey filaments, and the threshold of the reaction for the mechanical stimulation (50% threshold) was determined according to a method of Chaplan et al. (J. Neurosci. Methods, 53: 55-63, 1994). In this step, the stimulation of the sole of the paw with each filament was repeated 8 times at a rate of about twice a second.

Figure 2:
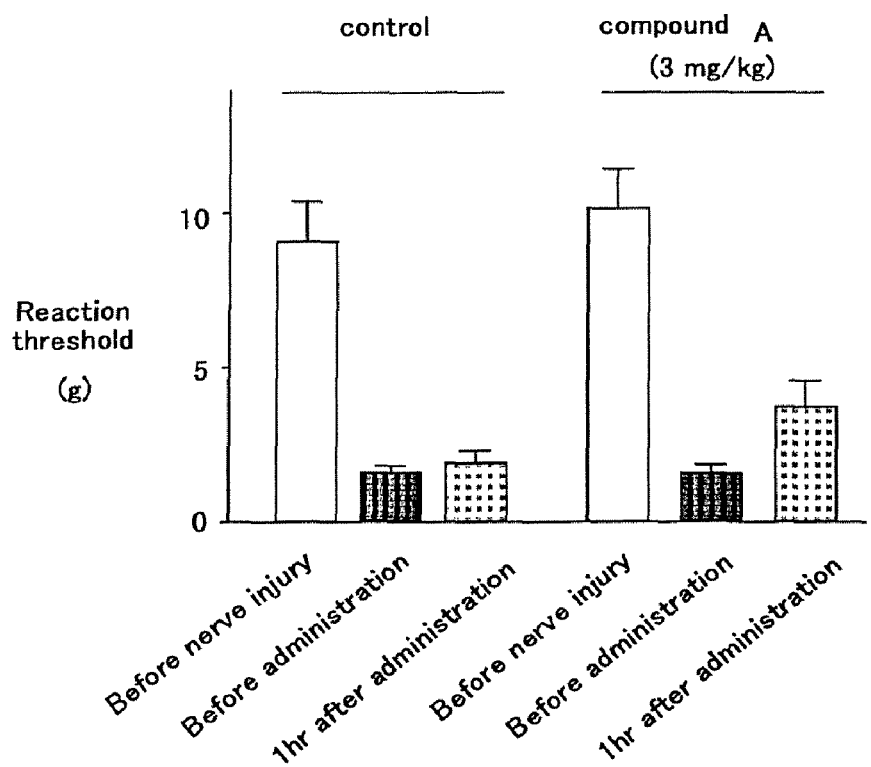
FIG. 2 shows the analgesic effect of compound A in the partial sciatic nerve ligation model.

About a half thickness of the right sciatic nerve of each 8 week-old male Sprague-Dawley (SD) rat, whose reaction threshold was determined before the nerve injury, was ligated with a surgical suture to partially injure the nerve according to a method of Seltzer et al. (Pain, 43: 205-218, 1990). Six days after the nerve injury, the reaction threshold of the right hindpaw was determined and compared with that determined before the nerve injury. Individuals having a threshold far lower than that determined before the nerve injury [i.e. rats showing mechanical allodynia] were selected for evaluating allodynia improving effect. Seven and 9 days after the nerve injury, the reaction threshold of the rats selected for the purpose of the evaluation was determined before compound administration. On the basis of the threshold, the test animals were divided into two groups [i.e. a control group to which 0.5% tragacanth solution would be given and a group to which 3 mg/kg of compound A would be given]. 5 ml/kg of 0.5% tragacanth solution or compound A was orally administered to the rats. One hour after the administration, the reaction threshold of each rat was determined.
<Results>
The results are shown in FIG. 2. In both groups, the reaction threshold of the paw before the administration was far lower than that determined before the nerve injury and, therefore, the development of the mechanical allodynia was confirmed.

In the control group (N=11), the reaction threshold after the administration was hardly changed. On the other hand, the reaction threshold was increased and a remarkable therapeutic effect on mechanical allodynia, one of the indicators of neuropathic pain, was recognized in the group to which 3 mg/kg of compound A had been given (N=13).

Test Example 5

Analgesic Effects in the Formalin Test

<Method>
The experiment was conducted in the same manner as that in above Test Example 3 except for the followings.

Five test groups each composed of 6 male Sprague-Dawley (SD) rats (9 weeks old) were used for the experiment. In the control group, polyethylene glycol 400 was given to the rats. In the other test groups, 3, 30, 100 or 300 mg/kg of the compound obtained in Example 71 (compound B) was given to them. Compound B was used in the form of a solution thereof in polyethylene glycol 400 (PEG).

Figure 3:
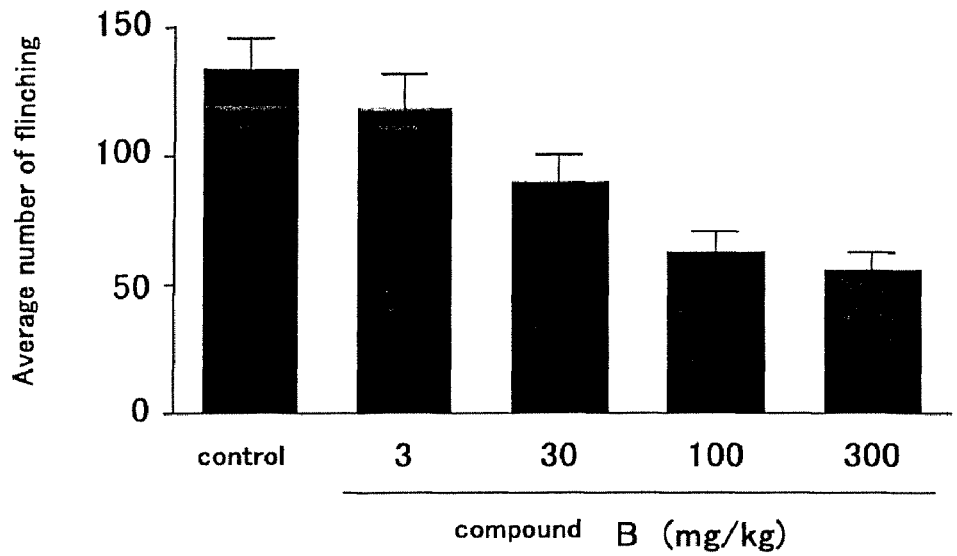
FIG. 3 shows the analgesic effect of compound B in the formalin test.

Three ml/kg of PEG or compound B was orally administered to the rats.
<Results>
FIG. 3 is a graph showing the average measurement±standard error in each experiment group. The inhibiting ratios of flinches in the groups of 3, 30, 100 and 300 mg/kg of compound B were 11, 33, 53 and 59%, respectively, based on the average number of the flinches in the control group. Thus, a remarkable analgesic effect was confirmed.

Test Example 6

Analgesic Effects on a Neuropathic Pain Model

Figure 4:
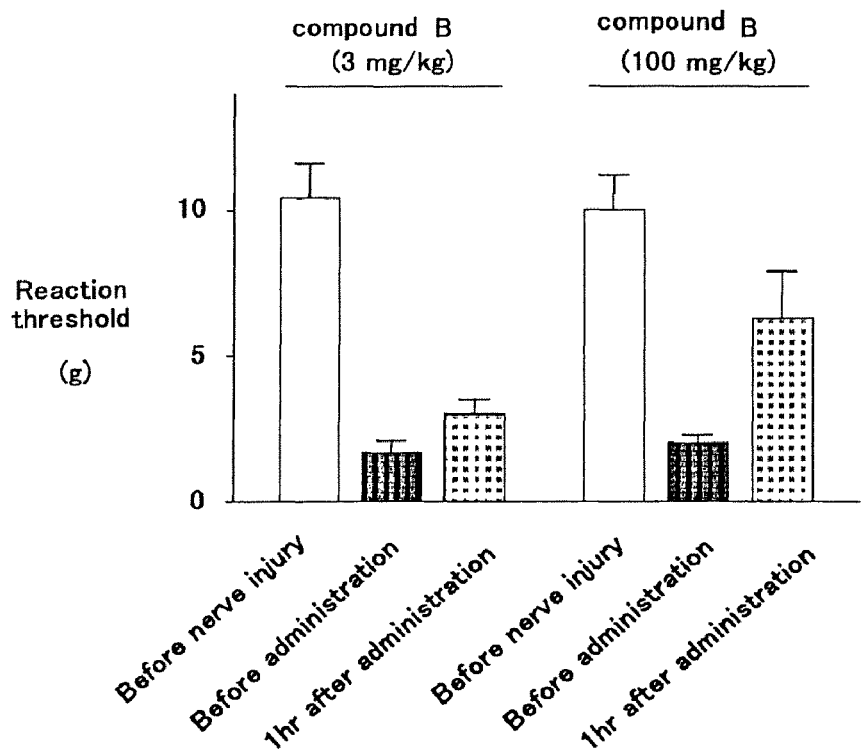
FIG. 4 shows the analgesic effect of compound B in the partial sciatic nerve ligation model.

<Method>
The effect of compound B in improving mechanical allodynia was evaluated using the partial sciatic nerve ligation model (Seltzer model, Pain, 43: 205-218, 1990) which belongs to the neuropathic pain models. The detection of the mechanical allodynia, method of injuring the right sciatic nerve and the experiment schedule were the same as those in Test Example 4. Six days after the nerve injury, the reaction threshold of the right hindpaw was determined and was compared with that determined before the nerve injury. Individuals having a threshold far lower than that determined before the nerve injury [i.e. rats showing mechanical allodynia] were selected for evaluating allodynia improving effect. Seven and 9 days after the nerve injury, the reaction threshold of the rats selected for the purpose of the evaluation was determined before compound administration. On the basis of the threshold, the test animals were divided into two groups [i.e. a group to which 3 mg/kg of compound B would be given and the other group to which 100 mg/kg of compound B would be given]. Compound B was dissolved in PEG and was orally administered at 3 ml/kg to the rats of 3 and 100 mg/kg groups. One hour after the administration, the reaction threshold of each rat was determined.
<Results>
The results are shown in FIG. 4. In both groups, the reaction threshold of the paw before compound administration was far lower than that determined before the nerve injury and, thus, the development of the mechanical allodynia was confirmed.

In the group (N=9) to which 3 mg/kg of compound B had been given, the reaction threshold after the administration was hardly changed. On the other hand, the reaction threshold was clearly increased and a remarkable therapeutic effect on mechanical allodynia, one of the indicators of neuropathic pain, was recognized in the group (N=7) to which 100 mg/kg of compound B had been administered.

From the results described above, it was confirmed that the new diarylalkene derivatives and diarylalkane derivatives have a high, selective antagonistic activity on N-type calcium channels and that they have a remarkable therapeutic effect on animal pain models. The effects of the conventional medicinal treatment, particularly for neuropathic pain, were insufficient. Patients having neuropathic pain are generally resistant to non-steroidal anti-inflammatory drugs and the treatment with opioids. Because the N-type calcium channel antagonists of the present invention exhibited a remarkable therapeutic effect on the neuropathic pain model, they are expected to have remarkable effects also in the clinical treatment of neuropathic pain patients. In addition, since the derivatives of the present invention exhibited remarkable therapeutic effect in the formalin test, a model of inflammatory pain, it was proved that they have a powerful effect also on pains other than the neuropathic pain. Thus, the derivatives of the present invention are useful as therapeutic agents for pains and also various diseases related to N-type calcium channels.

The new diarylalkene derivatives and diarylalkane derivatives of the present invention have the selective antagonistic activity on N-type calcium channels and they exhibited the therapeutic effects on the animal pain models. Thus, the new diarylalkene derivatives and diarylalkane derivatives of the present invention provide a method for treating various diseases, for example, pain [such as neuropathic pain (e.g. diabetic neuropathy, post-herpetic neuralgia, trigeminal neuralgia and complex regional pain syndrome), migraine, visceral pain, cancer pain, post-operative pain, back pain, HIV-related pain, arthritic pain and pain caused by spinal injury or diabetes]; for treating brain injury caused by ischemia at the acute stage after the onset of cerebral infarction, cerebral hemorrhage (including subarachnoidal hemorrhage) or the like; for treating progressive neurodegenerative diseases such as Alzheimer's disease, AIDS related dementia, Parkinson's disease, cerebrovascular dementia and ALS; for treating neuropathy caused by head injury; and for treating various diseases associated with psychogenic stress such as bronchial asthma, unstable angina and irritable colitis, emotional disorder and withdrawal symptoms after addiction to drugs such as ethanol addiction withdrawal symptoms.

What is claimed is:
1. A compound of formula (1), or a pharmaceutically acceptable salt thereof:

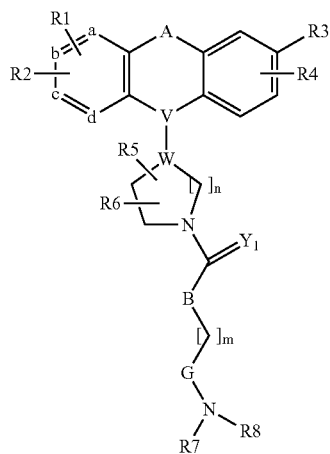

(1)

wherein A represents —CH=CH—;
a, b, c and d are each selected from the group consisting of $CR^1$ and $CR^2$;

$R^1$, $R^2$ and $R^4$ each independently represent H, a halogen, —$CF_3$, —$OR^{14}$, —$COR^{14}$, —$SR^{14}$, —$S(O)_tR^{15}$, —$N(R^{14})_2$, —$NO_2$, —$OC(O)R^{14}$, —$CO_2R^{14}$, —$OCO_2R^{14}$, —CN, —$NR^{14}COOR^{15}$, —$SR^{15}C(O)OR^{15}$ or —$SR^{15}N(R^{16})_2$ wherein $R^{14}$ represents H, a lower alkyl, an aryl or an aryl-lower alkyl group, $R^{15}$ represents a lower alkyl or an aryl group, $R^{16}$ is independently selected from the group consisting of H and —$C(O)OR^{15}$, and t represents 1 or 2;

$R^3$ represents H;
V—W represents C=C;
n represents 2 or 3;
$R^5$ and $R^6$ each independently represent H, a halogen, —$CF_3$, a lower alkyl or an aryl;
or $R^5$ and $R^6$ together form =O or =S;
$Y^1$ represents O or S;
B represents $NR^{17a}$, —$NR^{17a}(CH_2)_vCHR^{21}$—, —$(CH_2)_v CHR^{21}$— wherein v represents 0 to 3, $R^{17a}$ represents H, a lower alkyl or an aryl, $R^{21}$ represents H, a lower alkyl, an aryl, a hydroxyl-lower alkyl, —$CH_2SH$, —$CH_2CH_2SCH_3$, —$CH_2(CO)NH_2$, —$CH_2CH_2(CO)NH_2$, —$(CH_2)_w$—$COOR^{29}$, —$(CH_2)_w$—$NR^{29}R^{30}$ wherein $R^{29}$ and $R^{30}$ each independently represent hydrogen atom or a lower alkyl group, and w represents 0 to 4, —$(CH_2)_3NHC(NH_2)$=NH, benzyl, 4-hydroxybenzyl, 3-indoylmethyl or 5-imidazoylmethyl;
G represents —(CO)—, —(SO)—, —($SO_2$)— or a covalent bond;
m represents 0 to 6;
$R^7$ and $R^8$ each independently represent H, a lower alkyl, an aryl, —$(CO)R^{18a}$, —$(CS)R^{18a}$, —$(CO)NR^{18a}R^{19a}$, —$(CS)NR^{18a}R^{19a}$ wherein $R^{18a}$ represents H, a lower alkyl, an aryl or a cycloalkyl group which may have a hetero atom in the ring, $R^{19a}$ represents H, a lower alkyl or an aryl; or $R^{18a}$ and $R^{19a}$ together form a cycloalkyl which may have a halogen, —$CF_3$, a lower alkyl or an aryl as a substituent, —(CO)$OR^{20}$ or —(CS)$OR^{20}$ wherein $R^{20}$ represents an alkyl group having 1 to 12 carbon atoms, an aryl group or a cycloalkyl group which may have a hetero atom in the ring, or a group of formula (5):

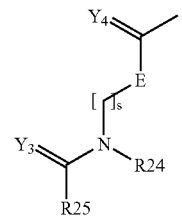

(5)

wherein $Y^4$ and $Y^3$ each represent O or S; s represents 0 to 6;
E represents $NR^{22}$ or $CHR^{23}$ wherein $R^{22}$ represents H, a lower alkyl or aryl; and $R^{23}$ represents H, a lower alkyl, an aryl, a hydroxyl-lower alkyl, —$CH_2SH$, —$CH_2CH_2SCH_3$, —$CH_2(CO)NH_2$, —$CH_2CH_2(CO)NH_2$, —$CH_2COOH$, —$CH_2CH_2COOH$, —$(CH_2)_4NH_2$, —$(CH_2)_3NHC(NH_2)$=NH, benzyl, 4-hydroxybenzyl, 3-indoylmethyl or 5-imidazoylmethyl;
$R^{24}$ represents H, a lower alkyl or an aryl;
$R^{25}$ represents H, a lower alkyl, an aryl, —$OR^{18a}$, —(CO)$R^{18a}$, —(CS)$R^{18a}$, —(CO)$NR^{18a}R^{19a}$, —(CS)

NR$^{18a}$R$^{19a}$, —(CO)OR$^{20}$ or —(CS)OR$^{20}$ wherein R$^{18a}$, R$^{19a}$ and R$^{20}$ are as defined above.

2. The compound or a pharmaceutically acceptable salt thereof according to claim 1, wherein in formula (1)

B represents NR$^{17a}$, CHR$^{21}$ and CH$_2$CHR$^{21}$ wherein R$^{17a}$ represents H, a lower alkyl or an aryl, R$^{21}$ represents H, a lower alkyl, an aryl, a hydroxyl-lower alkyl, —CH$_2$SH, —CH$_2$CH$_2$SCH$_3$, —CH$_2$(CO)NH$_2$, —CH$_2$CH$_2$(CO)NH$_2$, —CH$_2$COOH, —CH$_2$CH$_2$COOH, —(CH$_2$)$_4$NH$_2$, —(CH$_2$)$_3$NHC(NH$_2$)=NH, benzyl, 4—hydroxybenzyl, 3-indoylmethyl or 5-imidazoylmethyl; and R$^{18a}$ represents H, a lower alkyl or an aryl, and R$^{19a}$ represents H, a lower alkyl or aryl;

or R$^{18a}$ and R$^{19a}$ together form a cycloalkyl group which may have a halogen, —CF$_3$, a lower alkyl or an aryl as a substituent, and R$^{25}$ and R$^{27}$ each represent H, a lower alkyl, an aryl, —(CO)R$^{18a}$, —(CS)R$^{18a}$, —(CO)NR$^{18a}$R$^{19a}$, —(CS)NR$^{18a}$R$^{19a}$, —(CO)OR$^{20}$ or —(CS)OR$^{20}$.

3. The compound or a pharmaceutically acceptable salt thereof according to claim 2, wherein in formula (1)

a, b, c and d each represent CH;
R$^3$ and R$^4$ each represent hydrogen atom;
R$^5$ and R$^6$ each represent hydrogen atom;
or R$^5$ and R$^6$ together form =O;
n represents 1 or 2;
Y$^1$ represents O;
B represents NR$^{17a}$, CHR$^{21}$— or, CH$_2$CHR$^{21}$ wherein R$^{21}$ represents H, a lower alkyl, an aryl or —CH$_2$OH;
G represents —(CO)— or a covalent bond;
m represents 0 to 6;
R$^7$ and R$^8$ each independently represent H, a lower alkyl, an aryl, —(CO)R$^{18a}$ wherein R$^{18a}$ represents H, a lower alkyl or an aryl, —(CO)NR$^{18a}$R$^{19a}$ wherein R$^{19a}$ represents H, a lower alkyl or an aryl; or R$^{18a}$ and R$^{19a}$ together form a cycloalkyl which may have a halogen, —CF$_3$, a lower alkyl or an aryl as a substituent, —(CO)OR$^{20}$ wherein R$^{20}$ represents an alkyl group having 1 to 12 carbon atoms, an aryl group or a cycloalkyl group which may contain a hetero atom in the ring, or a group of formula (8):

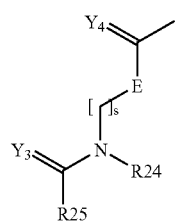

(8)

wherein Y$^4$ and Y$^3$ each represent O;
s represents 1 or 2;
E represents CHR$^{23}$ wherein R$^{23}$ represents H,
R$^{24}$ represents H;
R$^{25}$ represents —(CO)OR$^{20}$.

4. The compound or a pharmaceutically acceptable salt thereof according to claim 3, wherein in formula (1)
a, b, c and d each represent CH;
R$^1$ and R$^2$ each represent H;
R$^3$ and R$^4$ each represent H;
n represents 2;

R$^5$ and R$^6$ each represent H; and
Y$^1$ represents O.

5. The compound or a pharmaceutically acceptable salt according to claim 1, wherein in formula (1)

B represents —(CH$_2$)$_v$—CHR$^{21}$ wherein v represents 2 or 3, R$^{21}$ represents H, a lower alkyl, an aryl, a hydroxyl-lower alkyl, —CH$_2$SH, —CH$_2$CH$_2$SCH$_3$, —CH$_2$(CO)NH$_2$, —CH$_2$CH$_2$(CO)NH$_2$, benzyl, 4-hydroxybenzyl, 3-indoylmethyl or 5-imidazoylmethyl; and R$^{18a}$ represents H, a lower alkyl or an aryl, and R$^{19a}$ represents H, a lower alkyl or aryl; or R$^{18a}$ and R$^{19a}$ together form a cycloalkyl group which may have a halogen, —CF$_3$, a lower alkyl or an aryl as a substituent.

6. The compound or a pharmaceutically acceptable salt thereof according to claim 5, wherein in formula (1), a, b, c and d each represent CH;
R$^1$, R$^2$, R$^3$, R$^4$, R$^5$ and R$^6$ each represent H;
m represents 0 and n represents 2;
Y$^1$ represents O, G represents a covalent bond, and
R$^7$ and R$^8$ each independently represent H, a lower alkyl, —(CO)R$^{18a}$ wherein R$^{18a}$ represents H, a lower alkyl or an aryl, —(CO)OR$^{20}$ wherein R$^{20}$ represents an alkyl group having 1 to 12 carbon atoms or an aryl.

7. A compound represented by formula (11), or a pharmaceutically acceptable salt thereof:

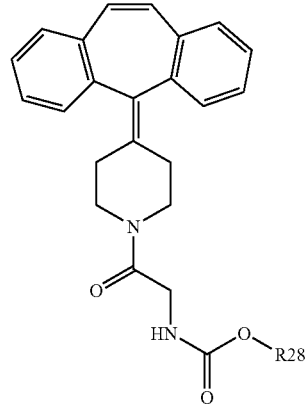

(11)

wherein R$^{28}$ represents an alkyl group having 1 to 12 carbon atoms, a cycloalkyl group having 3 to 12 carbon atoms or a cycloalkyl group which may have a hetero atom in the ring.

8. A compound of formula (1-A), or a pharmaceutically acceptable salt thereof:

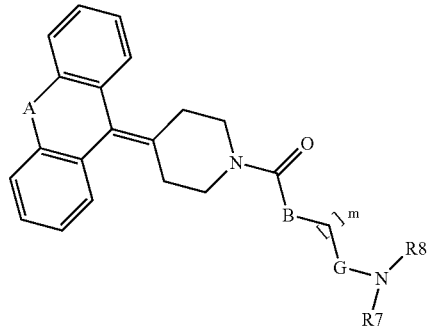

(1-A)

wherein A represents —CH=CH—;

B represents —(CH$_2$)$_v$—CHR$^{21}$ wherein v represents 0 to 3, R$^{21}$ represents H, a lower alkyl, an aryl, a hydroxyl-lower alkyl, —(CH$_2$)$_w$—COOR$^{29}$ or —(CH$_2$)$_w$—NR$^{29}$R$^{30}$ wherein R$^{29}$ and R$^{30}$ each independently represent hydrogen atom or a lower alkyl group and w represents 0 to 4;

G represents —(CO)— or a covalent bond;

m represents 0 to 6; and

R$^7$ and R$^8$ each independently represent H, a lower alkyl, an aryl, —(CO)R$^{18a}$ wherein R$^{18a}$ represents H, a lower alkyl, an aryl or a cycloalkyl group which may contain a hetero atom in the ring, or —(CO)OR$^{20}$ wherein R$^{20}$ represents an alkyl group having 1 to 12 carbon atoms, an aryl or a cycloalkyl group which may have a hetero atom in the ring.

9. A compound of the following formulae, or a pharmaceutically acceptable salt thereof:

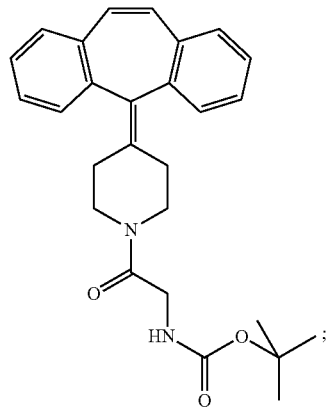

;

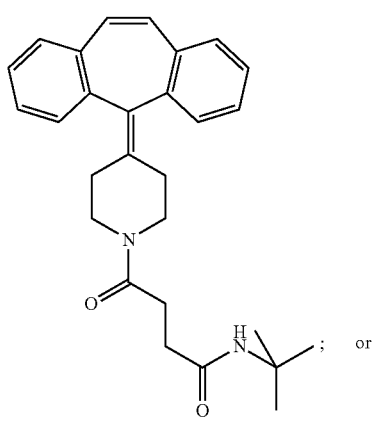

; or

-continued

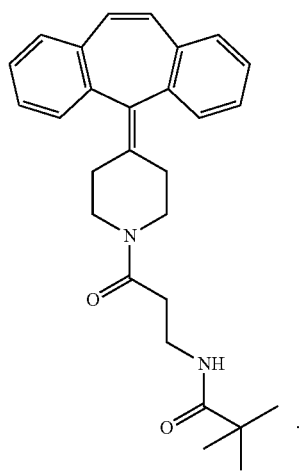

.

10. A compound of the following formulae, or a pharmaceutically acceptable salt thereof:

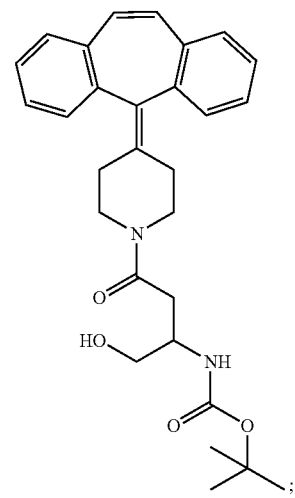

;

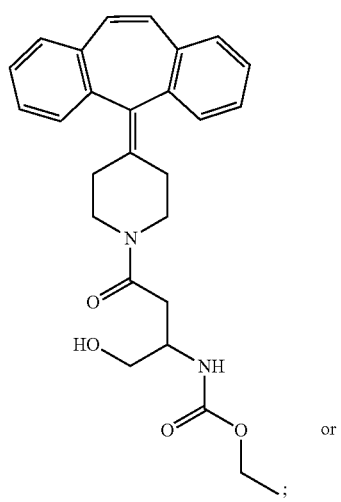

or

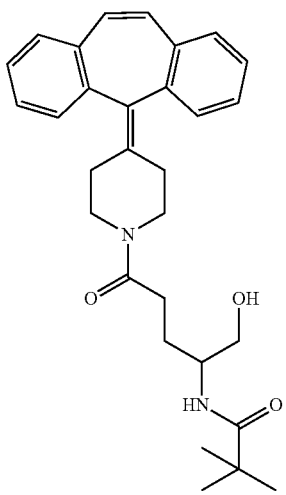

11. A pharmaceutical composition comprising at least one compound or pharmaceutically acceptable salt thereof according to claim 1 and at least one pharmaceutically acceptable adjuvant.

12. A pharmaceutical composition comprising at least one compound or pharmaceutically acceptable salt thereof according to claim 2 and at least one pharmaceutically acceptable adjuvant.

13. A pharmaceutical composition comprising at least one compound or pharmaceutically acceptable salt thereof according to claim 5 and at least one pharmaceutically acceptable adjuvant.

14. A pharmaceutical composition comprising at least one compound or pharmaceutically acceptable salt thereof according to claim 7 and at least one pharmaceutically acceptable adjuvant.

15. A pharmaceutical composition comprising at least one compound or pharmaceutically acceptable salt thereof according to claim 8 and at least one pharmaceutically acceptable adjuvant.

16. A pharmaceutical composition comprising at least one compound or pharmaceutically acceptable salt thereof according to claim 9 and at least one pharmaceutically acceptable adjuvant.

17. A pharmaceutical composition comprising at least one compound or pharmaceutically acceptable salt thereof according to claim 10 and at least one pharmaceutically acceptable adjuvant.

18. The compound of claim 9, or a pharmaceutically acceptable salt thereof, wherein said compound is:

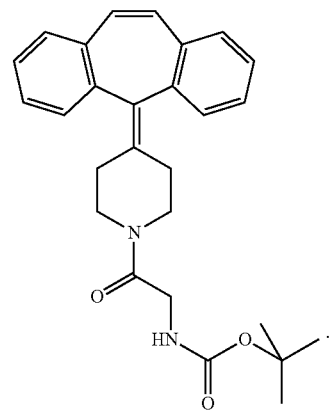

19. The compound of claim 9, or a pharmaceutically acceptable salt thereof, wherein said compound is:

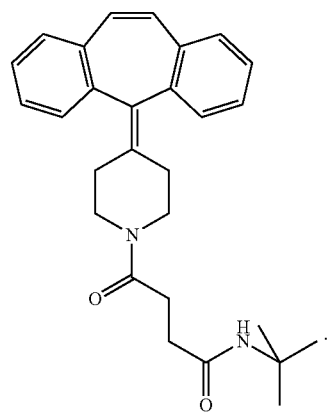

20. The compound of claim 9, or a pharmaceutically acceptable salt thereof, wherein said compound is:

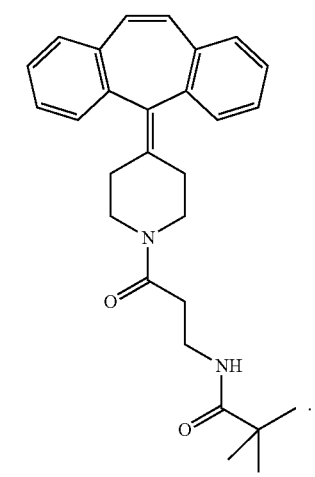

21. The compound of claim 10, or a pharmaceutically acceptable salt thereof, wherein said compound is:

22. The compound of claim 10, or a pharmaceutically acceptable salt thereof, wherein said compound is:
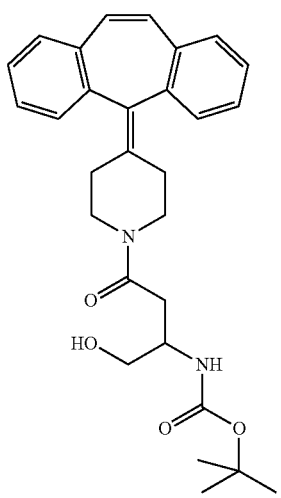
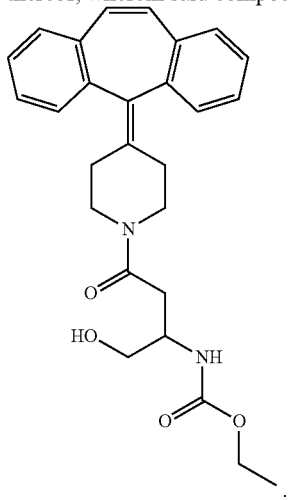
23. The compound of claim 10, or a pharmaceutically acceptable salt thereof, wherein said compound is:
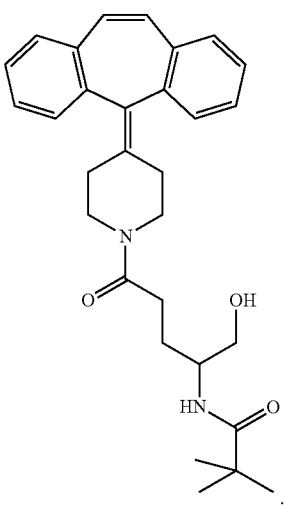
\* \* \* \* \*